(12) United States Patent
Mihara et al.

(10) Patent No.: US 7,188,999 B2
(45) Date of Patent: Mar. 13, 2007

(54) RADIATION TREATMENT APPARATUS

(75) Inventors: Kazumasa Mihara, Hiroshima-ken (JP); Kenji Hara, Hiroshima-ken (JP); Ichiro Yamashita, Hiroshima-ken (JP); Ikuo Wakamoto, Hiroshima-ken (JP); Yuichiro Kamino, Aichi-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 68 days.

(21) Appl. No.: 10/764,505

(22) Filed: Jan. 27, 2004

(65) Prior Publication Data

US 2004/0184579 A1   Sep. 23, 2004

Related U.S. Application Data

(63) Continuation of application No. PCT/JP02/08504, filed on Aug. 23, 2002.

(30) Foreign Application Priority Data

| Aug. 24, 2001 | (JP) | ............................. 2001-254891 |
| Aug. 24, 2001 | (JP) | ............................. 2001-254892 |
| Jan. 30, 2002 | (JP) | ............................. 2002-022253 |

(51) Int. Cl.
  *H05G 1/02*   (2006.01)
(52) U.S. Cl. ........................................ 378/197; 378/17
(58) Field of Classification Search ................ 378/65, 378/17, 62, 193, 196, 197
See application file for complete search history.

(56) References Cited

U.S. PATENT DOCUMENTS

| 2,781,454 A | 2/1957 | Green et al. ................... 378/65 |
| 2,890,349 A | 6/1959 | Huszar ......................... 378/65 |
| 3,466,439 A * | 9/1969 | Setala .......................... 378/65 |
| 4,230,129 A * | 10/1980 | LeVeen ....................... 607/154 |
| 5,207,223 A | 5/1993 | Adler .......................... 600/427 |
| 5,321,271 A | 6/1994 | Schonberg et al. ...... 250/492.3 |
| 5,612,989 A | 3/1997 | Van Der Ende ............ 378/197 |
| 6,260,999 B1 | 7/2001 | Wofford et al. ............. 378/205 |
| 6,307,914 B1 * | 10/2001 | Kunieda et al. ............... 378/65 |
| 6,385,286 B1 * | 5/2002 | Fitchard et al. ............... 378/65 |
| 6,575,624 B2 * | 6/2003 | Noegel et al. .............. 378/198 |

FOREIGN PATENT DOCUMENTS

DE   197 17 109 A1   4/1998

(Continued)

OTHER PUBLICATIONS

European Search Report dated Dec. 16, 2005.
EPO Communication with supplementary partial European search report dated Jan. 19, 2006.

*Primary Examiner*—Courtney Thomas
(74) *Attorney, Agent, or Firm*—Armstrong, Kratz, Quintos, Hanson & Brooks, LLP

(57) ABSTRACT

A radiation treatment apparatus includes a guide and a support member. The guide moves a radiation generating unit along an orbit with a predetermined radius such that an X-ray emitted from the radiation generating unit may cross an isocenter. The support member rotates the guide about a turning axis passing through the isocenter. The radiation generating unit is moved along a spherical plane by the guide and the support member and applies the X-ray toward the isocenter in multiple directions.

23 Claims, 40 Drawing Sheets

FOREIGN PATENT DOCUMENTS

| | | |
|---|---|---|
| EP | 0 702 982 A2 | 3/1996 |
| JP | 33-10100 | 11/1958 |
| JP | 52-18073 | 4/1977 |
| WO | WO 92/06644 A1 | 4/1992 |
| WO | WO 97/13552 A1 | 4/1997 |
| WO | WO 00/07669 A1 | 2/2000 |

* cited by examiner

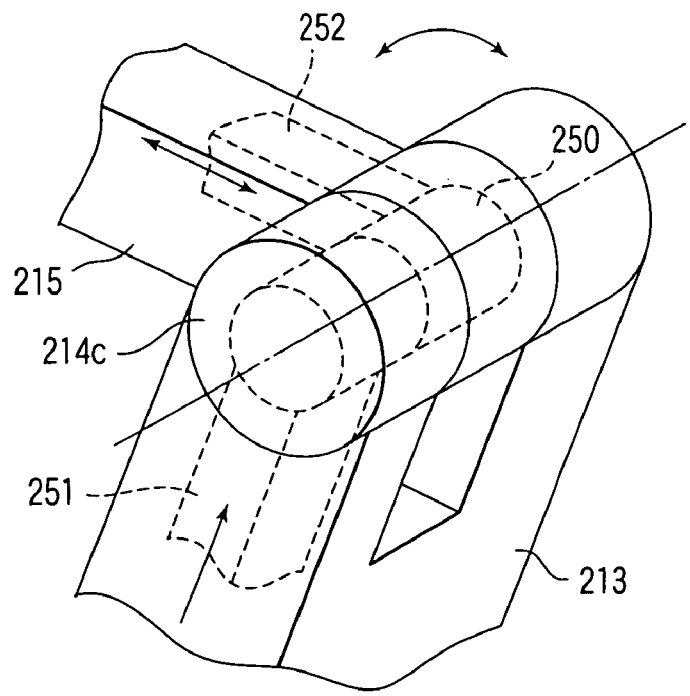
F I G. 22
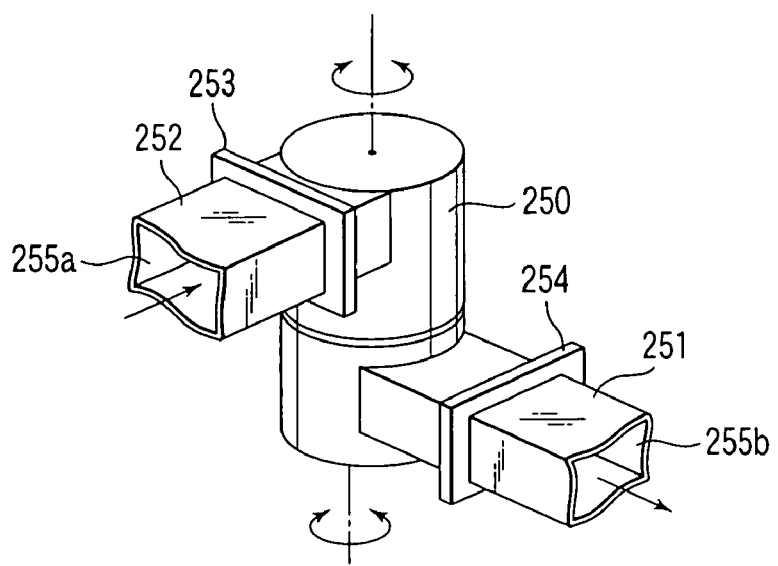
F I G. 23

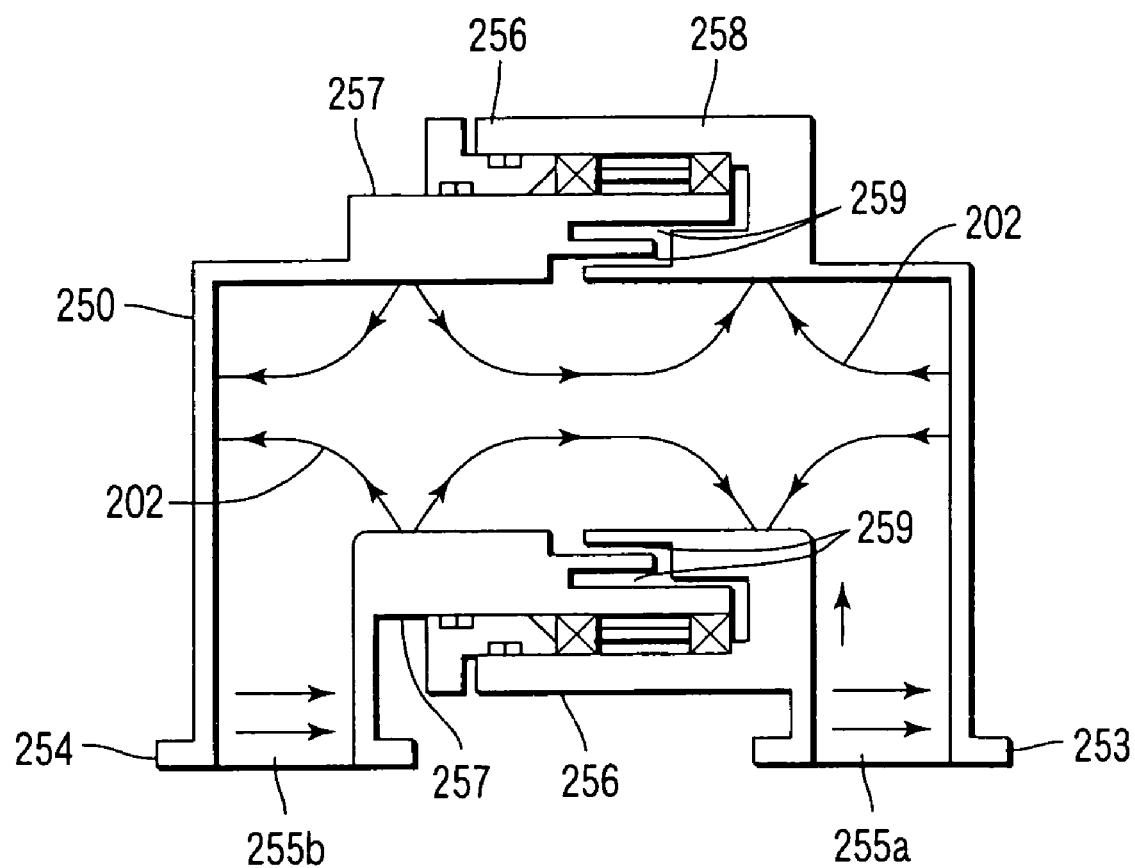
F I G. 24

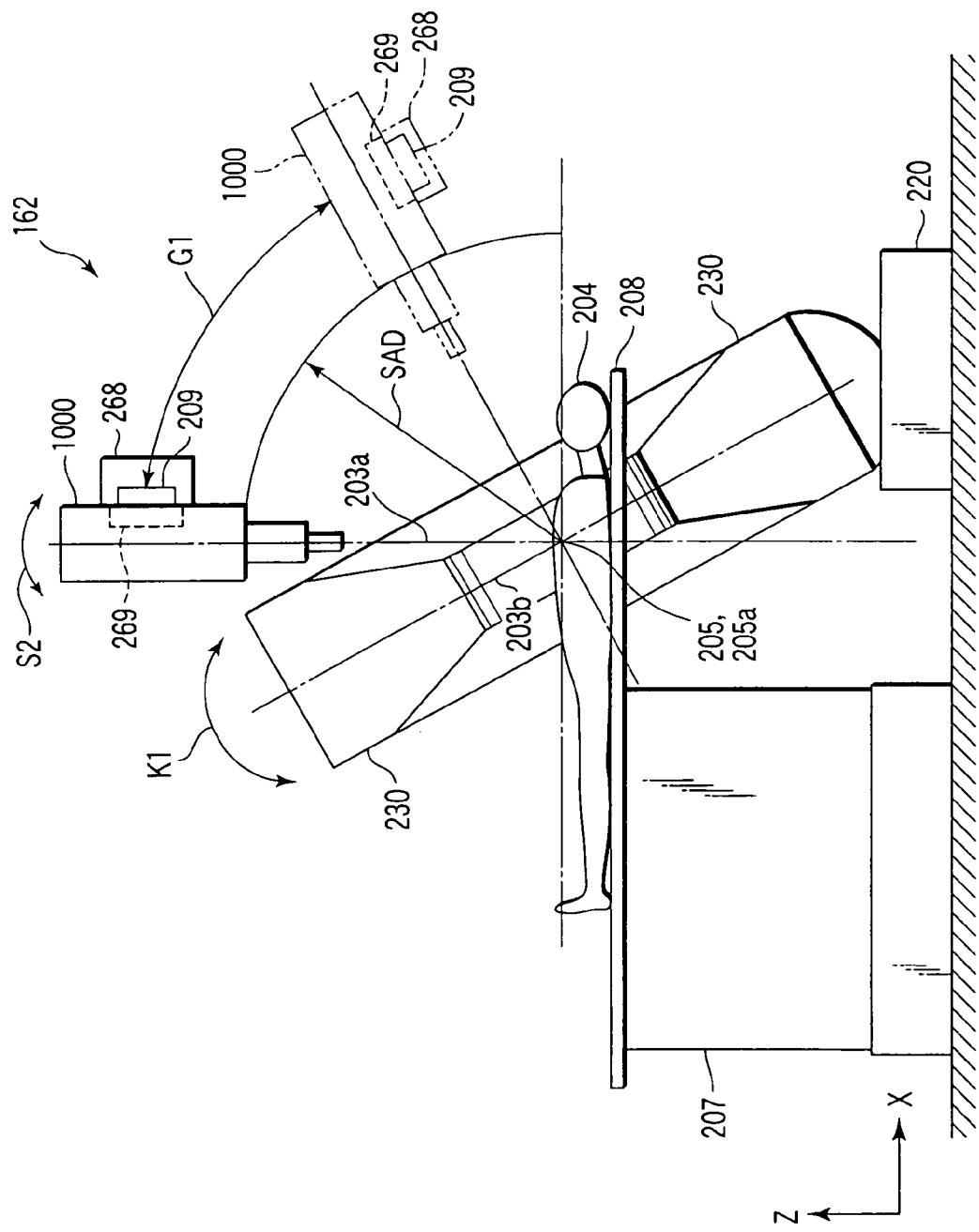
F I G. 27

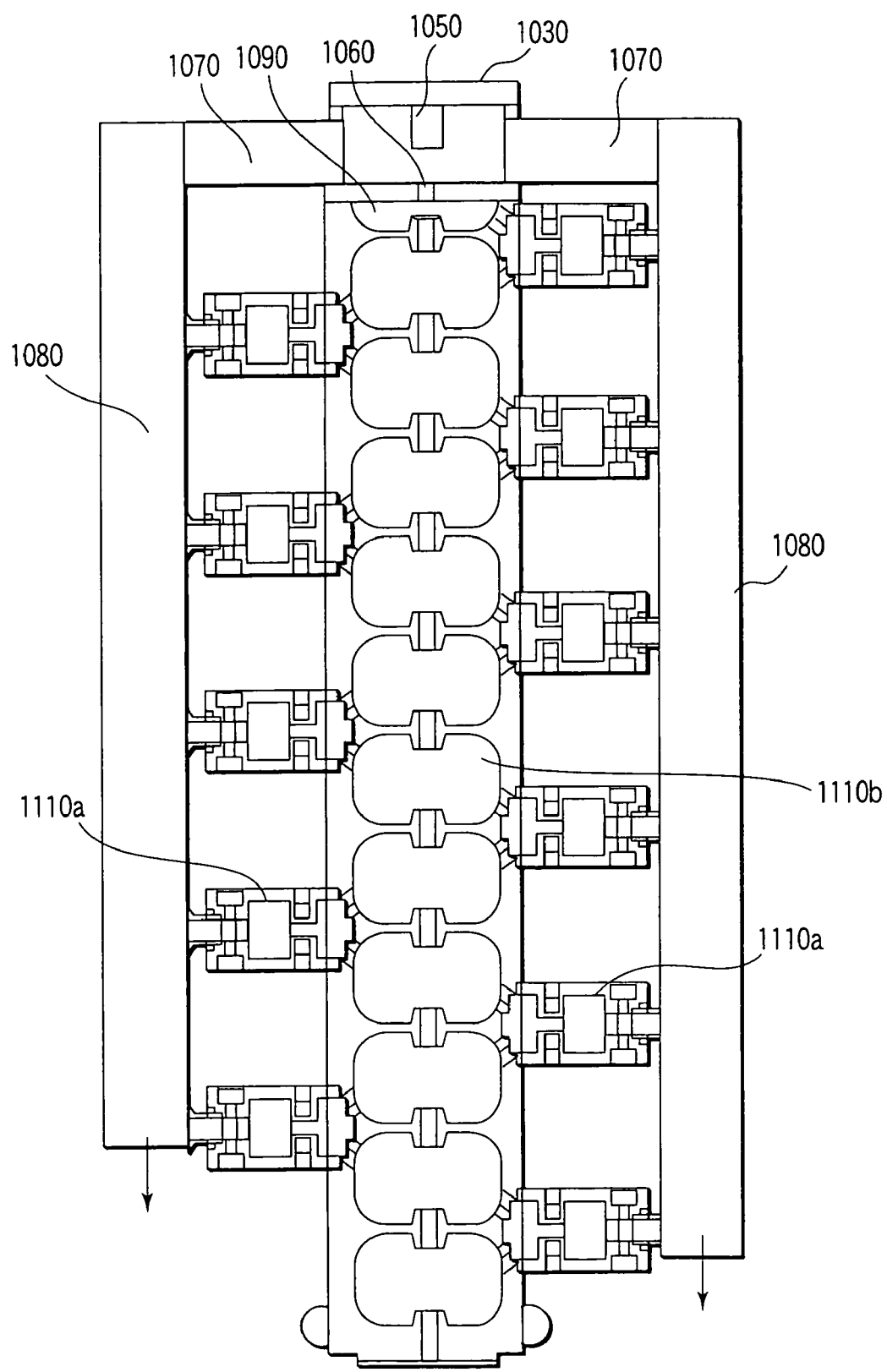
F I G. 31

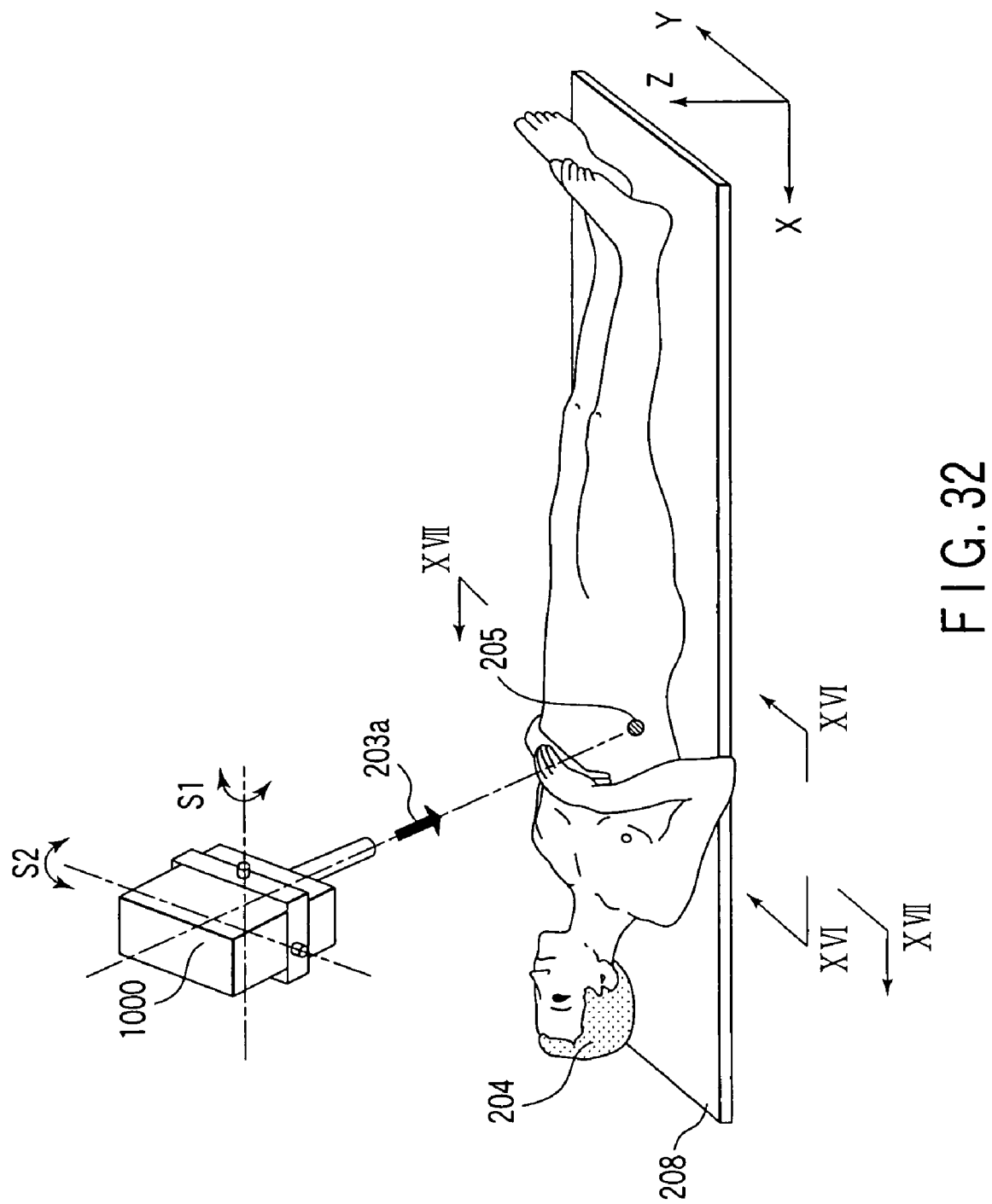
F I G. 32

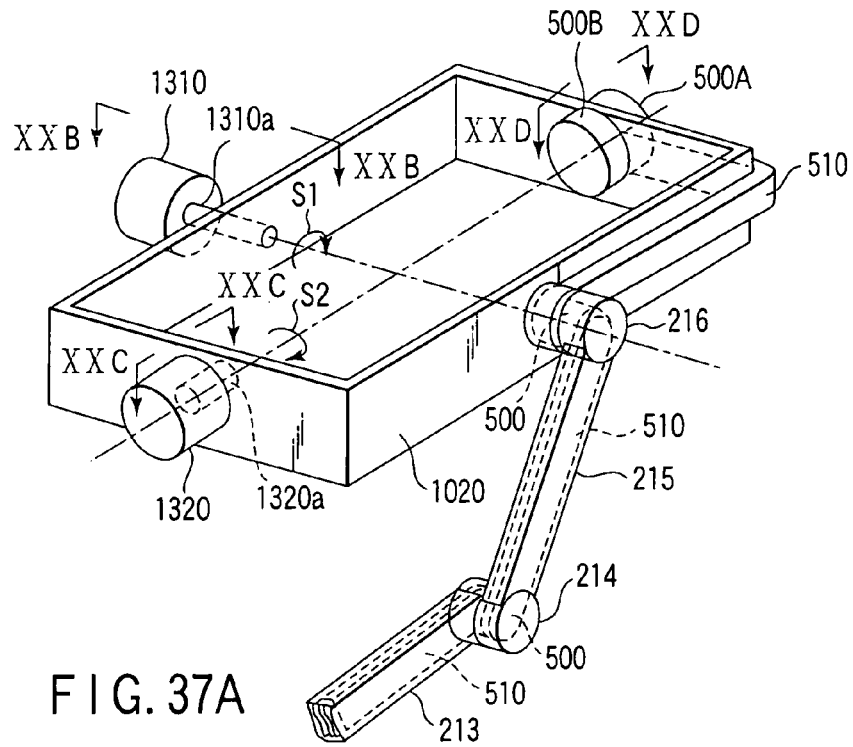
FIG. 37A
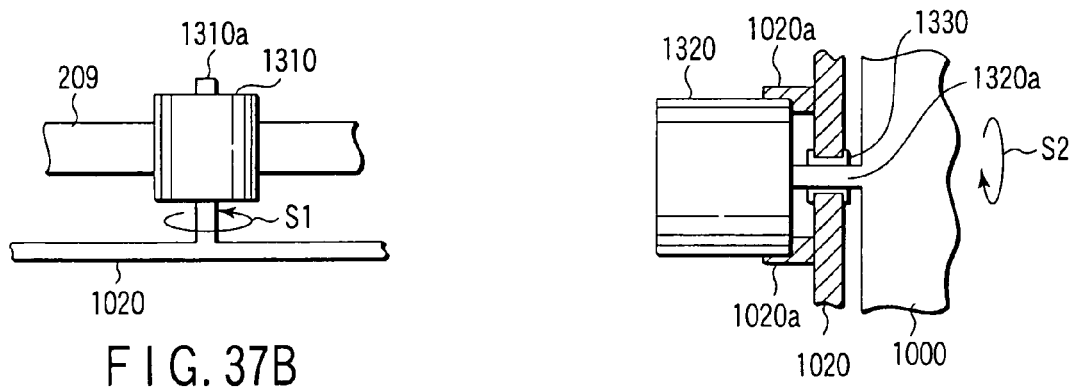
FIG. 37B
FIG. 37C
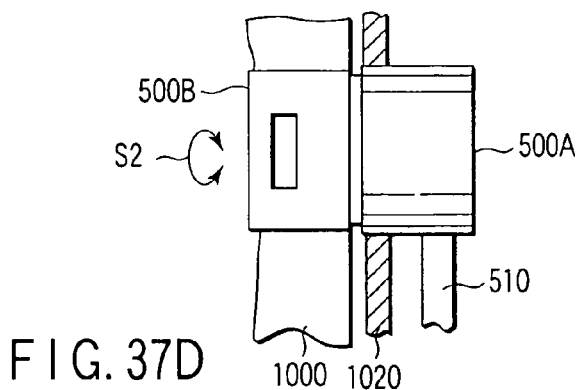
FIG. 37D

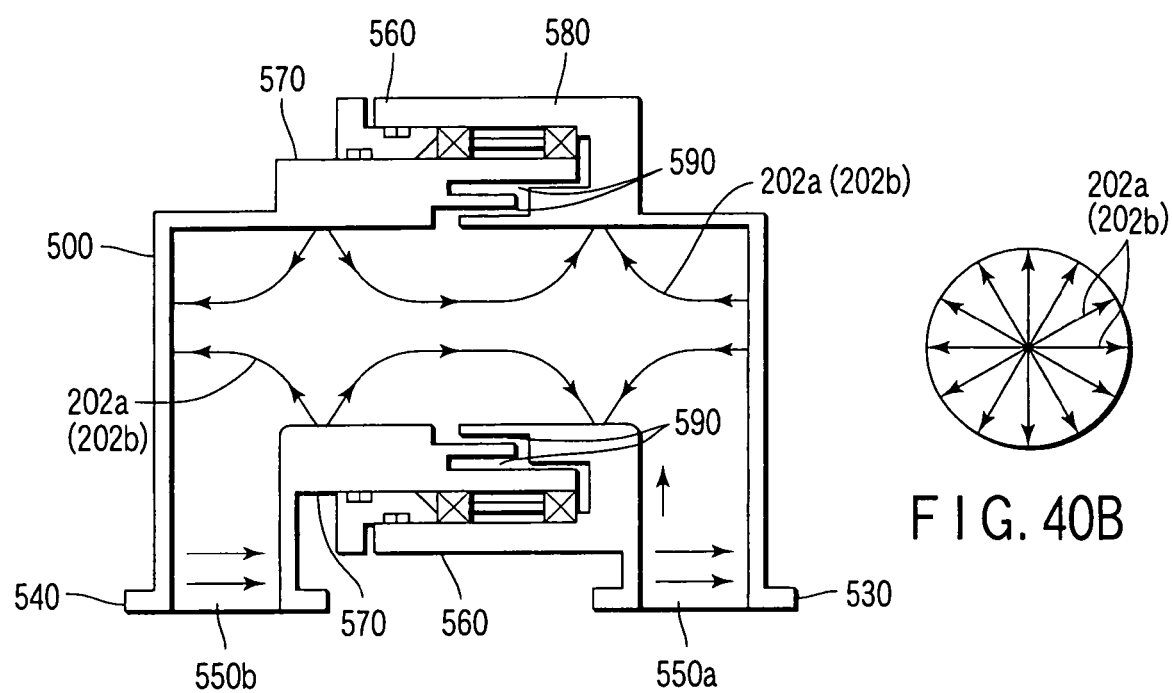
F I G. 40A
F I G. 40B

RADIATION TREATMENT APPARATUS

CROSS-REFERENCE TO RELATED APPLICATIONS

This is a Continuation Application of PCT Application No. PCT/JP02/08504, filed Aug. 23, 2002, which was not published under PCT Article 21(2) in English.

This application is based upon and claims the benefit of priority from the prior Japanese Patent Applications No. 2001-254891, filed Aug. 24, 2001; No. 2001-254892, filed Aug. 24, 2001; and No. 2002-022253, filed Jan. 30, 2002, the entire contents of all of which are incorporated herein by reference.

BACKGROUND OF THE INVENTION

1. Field of the Invention

The present invention relates to a radiation treatment apparatus having a radiation generating unit, which is movable around an object of radiation, and applying radiation to the object of radiation in multiple directions.

2. Description of the Related Art

For example, a radiation treatment apparatus for use in radiation treatment comprises a linear accelerator for generating radiation and a positioning device for passing the radiation, which is emitted from the linear accelerator, through an object of radiation in multiple directions.

There is a radiation treatment apparatus having as a positioning device a gantry that is rotatable about a horizontal axis. A linear accelerator is disposed within the gantry. Radiation is emitted from an end portion of the gantry toward the center of rotation. In this radiation treatment apparatus, when the gantry is rotated and radiation is emitted, radiation crosses at one point. Hence, this apparatus is called an isocentric type apparatus. An object of radiation is positioned at an isocenter.

In addition, there is a radiation treatment apparatus having a multi-axis manipulator as a positioning device. A linear accelerator is attached to the head of the multi-axis control manipulator. In this radiation treatment apparatus, when the manipulator is moved and radiation is emitted, radiation does not cross at a specified one point. Thus, this apparatus is called a non-isocentric type apparatus. An object of radiation is positioned within a range of movement of the manipulator.

In the radiation treatment apparatus having the gantry as the positioning device, the direction of application of radiation is varied only by the rotation of the gantry. Consequently, in order to apply radiation in a direction other than the direction of application of radiation that is varied by the rotation of the gantry, the object of radiation needs to be rotated about an axis at an angle different from the angle of the rotational axis of the gantry.

In particular, in radiation treatment, the object of radiation is within the body of a patient and thus the patient has to be rotated about the isocenter in order to rotate the object of radiation. In this case, the patient is inclined with respect to the isocenter, except the case where the patient is rotated about a vertical axis. As a result, the attitude of the patient or the shape of a diseased part may vary due to an external factor such as gravity.

In the radiation treatment apparatus having the multi-axis control manipulator as the positioning device, the direction of application of radiation can be set at a desired angle around the object of radiation by controlling each axis of the manipulator. Even when the direction of radiation is the same, the attitude of the manipulator is various and not singular. The bending of the manipulator and the load acting on each axis vary depending on the attitude. Consequently, it is difficult to precisely position the head that emits radiation. Moreover, the adjustment of position of the head is complex, and the reproducibility of the angle of application of radiation is low.

In these conventional radiation treatment apparatuses, the radiation cannot precisely be applied, and thus the amount of radiation on parts other than the object of radiation increases.

Under the circumstances, there is a demand for a radiation treatment apparatus that can apply radiation in multiple directions without inclining the object of application of radiation and has high reproducibility of the angle of application of radiation.

BRIEF SUMMARY OF THE INVENTION

A radiation treatment apparatus according to the present invention comprises a radiation generating unit, a guide and a support member. The radiation generating unit emits radiation. The guide moves the radiation generating unit along an orbit with a predetermined radius about an isocenter such that the emitted radiation crosses at one point. The support member rotates the guide about a turning axis passing through the isocenter.

In the radiation treatment apparatus according to the present invention, it is preferable that the turning axis be situated in parallel with a plane defined by the orbit, in order to maximize the range of movement of the radiation generating unit. In addition, it is preferable that the guide be supported by the support member at one portion on the turning axis, or at two portions on the turning axis on both sides of the isocenter.

In the radiation treatment apparatus according to the present invention, it is preferable that the guide be provided with a movable member that rotatably supports the radiation generating unit on two rotational axes crossing each other, thereby to apply radiation to an object of radiation apart from the isocenter. It is preferable that the movable member be disposed on at least a pair of rails provided on the guide in order to improve the reproducibility of the angle of application of radiation.

In the radiation treatment apparatus according to the present invention, it is preferable that the guide have a range of movement of the radiation generating unit, which is greater than a range that permits the radiation generating unit to emit the radiation to the isocenter in opposite directions.

In the radiation treatment apparatus according to the present invention, it is preferable that the guide be provided in an arcuate shape and supported by the support member on a turning axis horizontally or vertically extending through the isocenter. In addition, the guide may be provided in an annular shape and supported by the support member on a turning axis horizontally or vertically extending through the isocenter. The support member may be fixed to a position closer to the floor than to the isocenter, or fixed to a position closer to the ceiling than to the isocenter.

In the radiation treatment apparatus according to the present invention, it is preferable that the support member have a drive unit, which rotates the guide about the turning axis, at a location where the guide is rotatably supported. Where the guide is rotatably supported at two parts on the turning axis on both sides of the isocenter, the support member may have a drive unit, which rotates the guide about the turning axis, at least at one of locations where the guide is rotatably supported.

In the radiation treatment apparatus according to the present invention, the movable member has a drive unit that, for example, moves by holding a belt provided on an outer peripheral side of the guide.

In the radiation treatment apparatus according to the present invention, in order to vary the cross section of the emitted radiation, it is preferable that the radiation generating unit have a variable collimator having a window which is possible to change a shape for emission of radiation.

In the radiation treatment apparatus according to the present invention, in order to confirm the object of radiation positioned at the isocenter, it is preferable to further comprise a diagnosis imager that acquires information of a radiation transmission image.

In the radiation treatment apparatus according to the present invention, the imager includes a plurality of radiation sources and detectors paired with the radiation sources. The radiation sources may be disposed to acquire a three dimensional position and shape of the object of radiation such that emitted radiation crosses at the isocenter. The detectors may be disposed at such positions as to detect the radiation that has been emitted from the radiation sources and has passed through the isocenter.

In the radiation treatment apparatus according to the present invention, in order to direct the radiation emitted from the radiation generating unit to the object of radiation confirmed by the imager, it is preferable to further comprise a control unit which controls two axes of the movable member that rotatably supports the radiation generating unit, on the basis of the information acquired by the imager.

In the radiation treatment apparatus according to the present invention, in order to make the cross section of the radiation emitted from the radiation generating unit coincide with the shape of the object of radiation confirmed by the imager, it is preferable to further comprise a control unit that alters the shape of a window of a variable collimator, through which the radiation is emitted, on the basis of the information acquired by the imager.

In the radiation treatment apparatus according to the present invention, it is preferable that the imager be an X-ray CT scanner, in order to increase the amount of information of the acquired radiation transmission image.

In the radiation treatment apparatus according to the present invention, in order to reduce the weight of the radiation generating unit mounted on the guide, it is preferable to provide a microwave source positioned apart from the movable member and the guide, and to supply microwaves to the radiation generating unit via a waveguide.

In the radiation treatment apparatus according to the present invention, it is preferable to further comprise a movable table in order to position an object of radiation within a range including the isocenter. The movable table has a slide board on which the object of radiation is placed, and a drive mechanism that moves the slide board along three orthogonal axes.

A radiation treatment apparatus according to the present invention comprises: a radiation generating unit that emits treatment radiation; a movable member on which the radiation generating unit is mounted; a manipulator that positions the movable member in a desired direction; a variable collimator that alters a irradiation field of the treatment radiation emitted from the radiation generating unit; a diagnosis imager that detects a three-dimensional position and a three-dimensional shape of an object of radiation on which the treatment radiation is applied; a control unit that controls an emission port of the variable collimator, on the basis of the three-dimensional position and three-dimensional shape of the object of radiation detected by the diagnosis imager and an irradiation angle of the treatment radiation applied to the object of radiation, such that the irradiation field of the treatment radiation emitted from the emission port may vary in a tracking manner in accordance with the three-dimensional position and three-dimensional shape; and a 3-orthogonal-axis type positioning unit that positions the object of radiation at the irradiation field of the treatment radiation.

A radiation treatment apparatus according to the present invention comprises: a radiation generating unit that emits treatment radiation; a movable member on which the radiation generating unit is mounted; a gantry that rotates the movable member about a patient; a variable collimator that alters a irradiation field of the treatment radiation; a diagnosis imager that detects a three-dimensional position and a three-dimensional shape of an object of radiation on which the treatment radiation is applied; a control unit that controls an emission port of the variable collimator, on the basis of the three-dimensional position and three-dimensional shape of the object of radiation detected by the diagnosis imager and an irradiation angle of the treatment radiation applied to the object of radiation, such that the irradiation field of the treatment radiation emitted from the emission port may vary in a tracking manner in accordance with the three-dimensional position and three-dimensional shape; and a 3-orthogonal-axis type positioning unit that positions the object of radiation at the irradiation field of the treatment radiation.

A method of applying treatment radiation, according to the present invention, comprises: detecting, with use of a diagnosis imager, a three-dimensional position and a three-dimensional shape of an object of treatment of a patient positioned within a range of detection of the diagnosis imager; successively altering a position and a shape of an emission port of a variable collimator that permits passage of the treatment radiation, in accordance with a projection area of the object of treatment as viewed in a direction in which the treatment radiation is applied, on the basis of an irradiation angle of the treatment radiation and the three-dimensional position and three-dimensional shape of the object of treatment detected by the diagnosis imager; and successively adjusting a irradiation field of the treatment radiation in a tracking manner in accordance with the object of treatment.

A control method for a radiation treatment apparatus having a diagnosis imager, according to the present invention, comprises: detecting, with use of the diagnosis imager, a three-dimensional position and a three-dimensional shape of an object of treatment of a patient positioned within a range of detection of the diagnosis imager; and successively altering a position and a shape of an emission port of a variable collimator that permits passage of the treatment radiation in order to successively adjust a irradiation field of the treatment radiation in a tracking manner in accordance with the object of treatment, in accordance with a projection area of the object of treatment as viewed in a direction in which the treatment radiation is applied, on the basis of an irradiation angle of the treatment radiation and the three-dimensional position and three-dimensional shape of the object of treatment detected by the diagnosis imager.

BRIEF DESCRIPTION OF THE SEVERAL VIEWS OF THE DRAWING

FIG. 22 is a perspective view of a waveguide system and a rotary RF coupler in the radiation treatment apparatus according to the 14th embodiment;

FIG. 23 is a perspective view of the rotary RF coupler and waveguides in the radiation treatment apparatus according to the 14th embodiment;

FIG. 24 is a view for describing the rotary RF coupler in the radiation treatment apparatus according to the 14th embodiment;

FIG. 27 shows the structure of a radiation treatment apparatus according to a 15th embodiment of the invention, which is viewed in a direction perpendicular to the axis of the bed;

FIG. 31 shows the structure of a very-small-sized C-band accelerator provided in the radiation head in the radiation treatment apparatus of the 15th embodiment;

FIG. 32 is a perspective view showing a radiation head and a patient in a case of performing radiation treatment in a pseudo-non-isocentric manner using the radiation treatment apparatus of the 15th embodiment;

FIGS. 37A to 37D show a swinging mechanism in the 15th embodiment, FIG. 37A being a perspective view showing a waveguide, the swinging mechanism and a drive motor, FIG. 37B being a cross-sectional view taken along line XXB—XXB in FIG. 37A, FIG. 37C being a cross-sectional view taken along line XXC—XXC in FIG. 37A, and FIG. 37D being a cross-sectional view taken along line XXD—XXD in FIG. 37A;

FIGS. 40A and 40B are views for describing the rotary RF coupler in the radiation treatment apparatus according to the 15th embodiment;

DETAILED DESCRIPTION OF THE INVENTION

Figure 1:
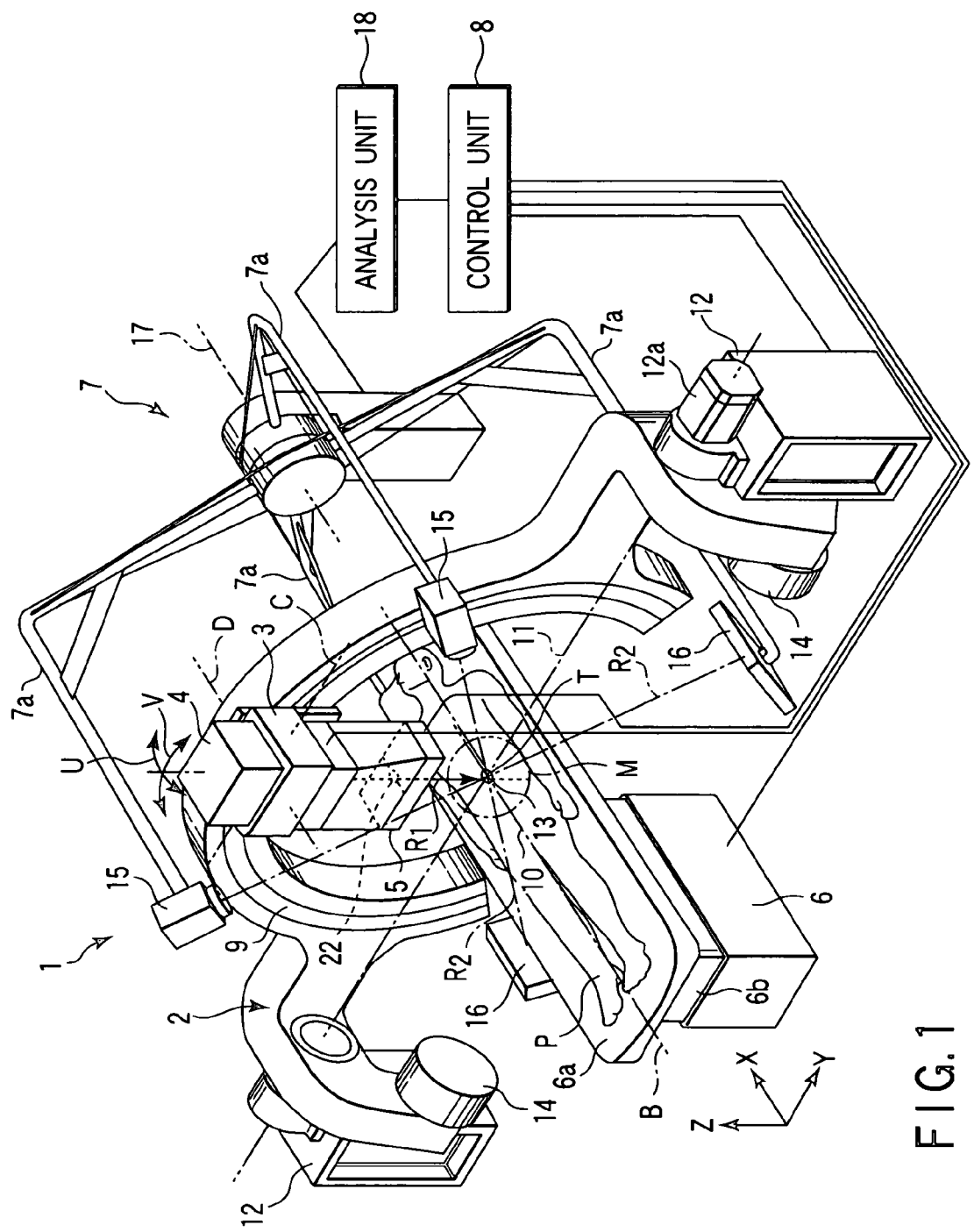
FIG. 1 is a perspective view showing a radiation treatment apparatus according to a first embodiment of the present invention.

A radiation treatment apparatus 1 according to a first embodiment of the present invention will now be described with reference to FIGS. 1 and 2. The radiation treatment apparatus 1 shown in FIG. 1 comprises a radiation generating unit 4, a variable collimator 5, a manipulator 2, a movable table 6, a diagnosis imager 7, and a control unit 8.

The radiation generating unit 4 emits an X-ray $R_1$ as radiation for treatment. The X-ray $R_1$ is generated by accelerating electrons emitted from an electron gun through an accelerator, and making the accelerated electrons impinge upon a target.

The variable collimator 5 is attached to an emission port of the radiation generating unit 4. Accordingly, the generated X-ray $R_1$ is emitted through the variable collimator 5. As is shown in FIG. 2, the variable collimator 5 includes two slide groups 19a, 19b. Each slide group 19a, 19b comprises a number of slides 20a, 20b, which are movable in an S-direction perpendicular to an A-direction in which the X-ray $R_1$ is emitted. The slides 20a, 20b are bundled in a W-direction perpendicular to each of the A-direction and S-direction. The slide groups 19a, 19b are arranged with their end portions abutted on each other in the S-direction. The slides 20a, 20b have such a shield thickness and is made of such a material that the X-ray $R_1$ can sufficiently be absorbed. For example, the slides 20a, 20b are made essentially of a metal with a great specific gravity, e.g. tungsten or lead. As is shown in FIG. 1, the variable collimator 5 is controlled by the control unit 8, so that an emission port 22 of a desired cross-sectional shape may be created between the slide groups 19a, 19b within a movement range 21 of the slides 20a, 20b.

The manipulator 2, as shown in FIG. 1, comprises a movable member 3, a guide 9, and support members 12. The movable member 3 rotatably supports the radiation generating unit 4 on two rotational axes C and D that intersect each other. The rotational axes C and D are arranged to intersect at right angles with the direction of emission of the X-ray $R_1$ that is emitted from the radiation generating unit 4. The rotational axis C is an axis for inclining the radiation generating unit 4 in directions of a double-headed arrow U. The rotational axis D is an axis for inclining the radiation generating unit 4 in directions of a double-headed arrow V. Thereby, the radiation generating unit 4 performs a so-called "swinging" operation. The movable member 3 is supported by the guide 9 and is moved along the guide 9 by a drive unit (not shown).

The guide 9 is formed in an arcuate shape. The guide 9 moves the radiation generating unit 4 along an orbit with a predetermined radius, around an isocenter 13 where the X-ray $R_1$ emitted from the radiation generating unit 4 intersects at one point. The guide 9 has a movement range greater than a range that permits the radiation generating unit 4 to emit the X-ray $R_1$ in opposite directions. In short, the guide 9 can rotate the radiation generating unit 4 over 180° or more about the isocenter 13.

The support members 12 rotate the guide 9 on a turning axis 11. The turning axis 11 is set to be horizontal so that the guide 9 is disposed in a so-called Ω shape. The turning axis 11 intersects at the isocenter 13 with a rotational axis 10 about which the radiation generating unit 4 moves along the guide 9. In this case, it is preferable that the rotational axis 10 and turning axis 11 intersect at right angles with each other, in consideration of a positioning control of the radiation generating unit 4. If the rotational axis 10 and turning axis 11 are set to intersect at right angles with each other, the turning axis 11 becomes in parallel with a plane defined by the orbit along which the radiation generating unit 4 moves, and vice versa.

The support members 12 are arranged on both sides of the isocenter 13 along the turning axis 11. The support members 12 are fixed on the floor. A servo motor 12a serving as a drive unit for rotating the guide 9 is attached to one of the two support members 12 at a position where the guide 9 is rotatably supported.

The guide 9 is disposed to be eccentric to the isocenter 13. In order to place the center of gravity on the turning axis 11, a counterweight 14 is attached on the side opposite to the guide 9 with respect to the turning axis 11. Even in the state in which the guide 9 is inclined, the center of gravity arranges on the turning axis 11. Thus, the load on the servo motor 12a is reduced.

As has been described above, according to the radiation treatment apparatus 1, the manipulator 2 positions the radiation generating unit 4 on a spherical surface defined around the isocenter 13. Hence, the control unit 8 can easily control the position of the radiation generating unit 4, if polar coordinates are used.

In addition, using the rotational axes C and D, the radiation treatment apparatus 1 can displace the direction of the X-ray $R_1$, which emitted from the radiation generating unit 4, from the isocenter 13. In short, the radiation treatment apparatus 1 can position the radiation generating unit 4 around the isocenter 13 and can non-isocentrically position the irradiation field of the X-ray $R_1$ apart from the isocenter 13.

The movable table 6, as shown in FIG. 1, comprises a slide board 6a on which a patient P who requires radiation treatment is placed, and a drive mechanism 6b that moves the slide board 6a along three orthogonal axes. The movable table 6 is disposed such that the body axis B of the patient P is directed perpendicular to the turning axis 11 of the manipulator 2. By using the drive mechanism 6b, the movable table 6 can position at the isocenter 13 a focus T that is to be treated as an object of radiation and is located within the patient P.

The diagnosis imager 7, as shown in FIG. 1, comprises X-ray sources 15, detectors 16 and an analysis unit 18. The X-ray sources 15 are a plurality of radiation sources. In this embodiment, two X-ray sources 15 are provided. The X-ray sources 15 are arranged such that X-rays $R_2$ emitted there-from may intersect at the isocenter 13. Each detector 16 is paired with the associated X-ray source 15. The detector 16 is disposed in point-symmetry with the X-ray source 15 with respect to the isocenter 13. The detectors 16 detect information of X-rays $R_2$ that pass through a detection range M centering on the isocenter 13. The detected information is sent to the analysis unit 18. Based on azimuthal information on the X-ray sources 15 and detectors 16 and the information of X-rays $R_2$ that has been sent, the analysis unit 18 finds a three-dimensional position and a three-dimensional shape, with reference to the isocenter 13, of the focus T positioned within the detection range M. The pairs of radiation sources 15 and detectors 16, with their positional relationship being maintained, are supported on arms 7a. Each arm 7a rotates the associated X-ray source 15 and detector 16 about an axis 17 extending perpendicular to the turning axis 11 through the isocenter 13.

The control unit 8, as shown in FIG. 1, is connected to the manipulator 2, radiation generating unit 4, variable collimator 5, movable table 6 and diagnosis imager 7, and provides soft limits for preventing mutual contact of these components. On the basis of the information on the three-dimensional position and three-dimensional shape of the focus T obtained by the diagnosis imager 7 and the positional and angular information of the radiation generating unit 4 positioned by the manipulator 2, the control unit 8 finds a projected cross-sectional shape of the X-ray $R_1$ that has been radiated from the radiation generating unit 4 onto the focus T. Based on the found radiation-projected cross-sectional shape, the control unit 8 controls the shape of an emission port 22 of the variable collimator 5. In addition, the control unit 8 has a monitor and a console panel, although not shown. The monitor permits visual confirmation of a transmission diagnosis image of the inspection range M and a three-dimensional position and a three-dimensional shape of the focus T, on the basis of the information of the X-rays $R_2$ detected by the diagnosis imager 7. The console panel is provided for remote control of the manipulator 2, radiation generating unit 4, variable collimator 5, movable table 6 and diagnosis imager 7.

The operation of the radiation treatment apparatus 1 having the above structure will now be described. The patient P with the focus T to be subjected to radiation treatment is placed on the slide board 6a. The movable table 6 positions the focus T, which has been determined by an inspection made in advance, at the vicinity of the isocenter 13. Since the focus T is located within the inspection range M, the position thereof is confirmed by the diagnosis imager 7 and is finely adjusted, when necessary, by moving the movable table 6.

On the basis of a treatment plan laid out according to the inspection made in advance and the information on the focus T and its vicinity obtained by the diagnosis imager 7, the radiation treatment apparatus 1 sets, for example, a shape of a irradiation field and an angle of radiation of the X-ray $R_1$ to be radiated on the focus T.

Figure 2:
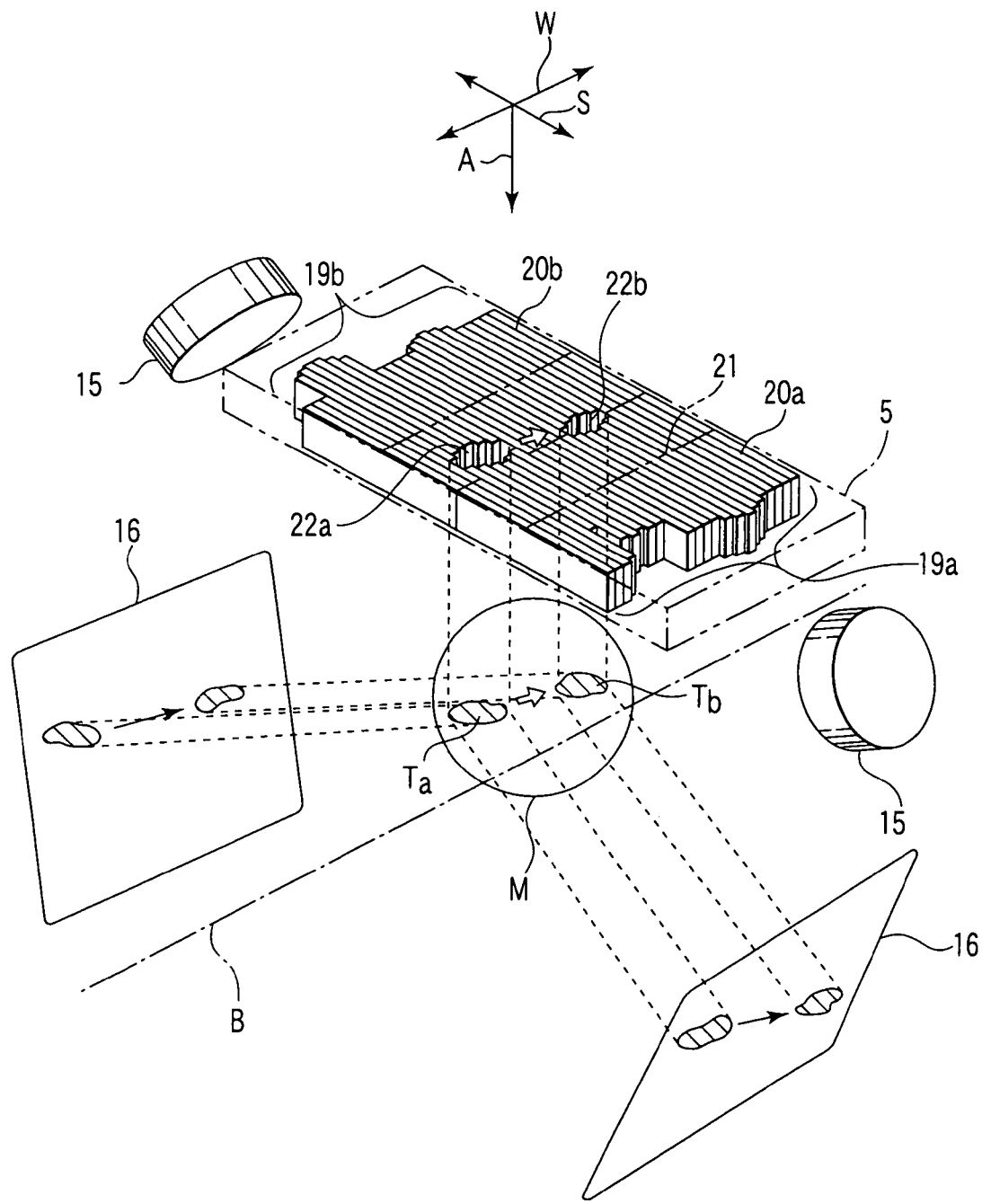
FIG. 2 is a perspective view showing a positional relationship between an object of radiation, and a variable collimator and a diagnosis imager that are components of the radiation treatment apparatus shown in FIG. 1.

In a case as shown in FIG. 2, the focus T changes its shape or moves from Ta to Tb. In this case, the diagnosis imager 7 performs X-ray transmission imaging of the inspection range M centering on the isocenter 13, at sufficiently short time intervals relative to the change of shape or movement. Thereby, the three-dimensional position and three-dimensional shape of the focus T are tracked by the analysis unit 18 of diagnosis imager 7, on the basis of the obtained information of X-rays $R_2$.

Based on the three-dimensional position and three-dimensional shape of the focus T tracked by the analysis unit 18 and the positional relationship between the manipulator 2, radiation generating unit 4 and diagnosis imager 7, the control unit 8 finds, in a time-sequential manner, the radiation-projected cross-sectional shape of the X-ray radiated from the radiation generating unit 4 onto the focus T. The control unit 8 alters the emission port 22 of variable collimator 5 from 22a to 22b so as to vary the irradiation field of X-ray $R_1$ in accordance with the radiation-projected cross-sectional shape of the focus T that changes from Ta to Tb as it moves or changes its shape.

As has been described above, in this radiation treatment apparatus 1, the radiation generating unit 4 is moved along the orbit of a given radius of the guide 9 around the isocenter 13, and the guide 9 is rotated on the turning axis 11 passing through the isocenter 13. Thus, the radiation treatment apparatus 1 positions the radiation generating unit 4 on a spherical surface defined around the isocenter 13. Accordingly, the X-ray $R_1$ can be radiated three-dimensionally in multiple directions on the object of radiation, such as the focus T, located at the isocenter 13, without the need to move the object of radiation.

Since the radiation treatment apparatus 1 has the diagnosis imager 7, the position and shape of the focus T can be tracked and the X-ray $R_1$ can be radiated even if the focus T moves or changes its shape during radiation treatment. When the components that are actually operated during tracking the focus T are the slides 20a, 20b of the variable collimator 5. In this radiation treatment apparatus 1, the irradiation field of X-ray $R_1$ can be made to follow the movement or change of shape of the focus T, without moving the manipulator 2 or radiation generating unit 4. Therefore, the radiation treatment apparatus 1 has good tracking responsivity to little-by-little or quick movement or change of shape of the focus T, and precise tracking can be carried out.

In the radiation treatment apparatus 1, the irradiation field of X-ray $R_1$ can properly be adjusted to conform to the position or shape of the focus T, on the basis of the information of the diagnosis imager 7 obtained during treatment. Thus, the dose of unnecessary radiation on parts other than the object of radiation can be reduced. Since the radiation treatment apparatus 1 can continuously apply the X-ray $R_1$ to the focus T, the time of treatment can be decreased. As a result, the load on the patient P can be reduced.

Possible factors of movement of the focus T during treatment are heartbeats, respiratory movement, peristalsis, etc. These physiological movements are greater in the direction of the body axis B. Thus, the movable collimator 5 is attached such that the W-direction in which the slides 20a, 20b are bundled coincides with the body axis B. The range within which the irradiation field of X-ray $R_1$ can be made to follow the movement of the focus T, can be increased by increasing the number of slides 20a, 20b to be bundled.

In order to reduce the weight of the radiation generating unit 4 mounted on the movable member 3, it is possible to provide a microwave generating unit, e.g. a Klystron, on a base portion of the manipulator 2 and to guide microwaves from the Klystron to an accelerator built in the radiation generating unit 4 with use of a waveguide. A concrete example of this case will be described below as a second embodiment of the invention.

A radiation treatment apparatus according to the second embodiment of the invention will now be described with reference to FIGS. 3 to 6. The same parts as those of the radiation treatment apparatus 1 of the first embodiment are denoted by same reference numerals, and a description thereof is omitted.

Figure 3:
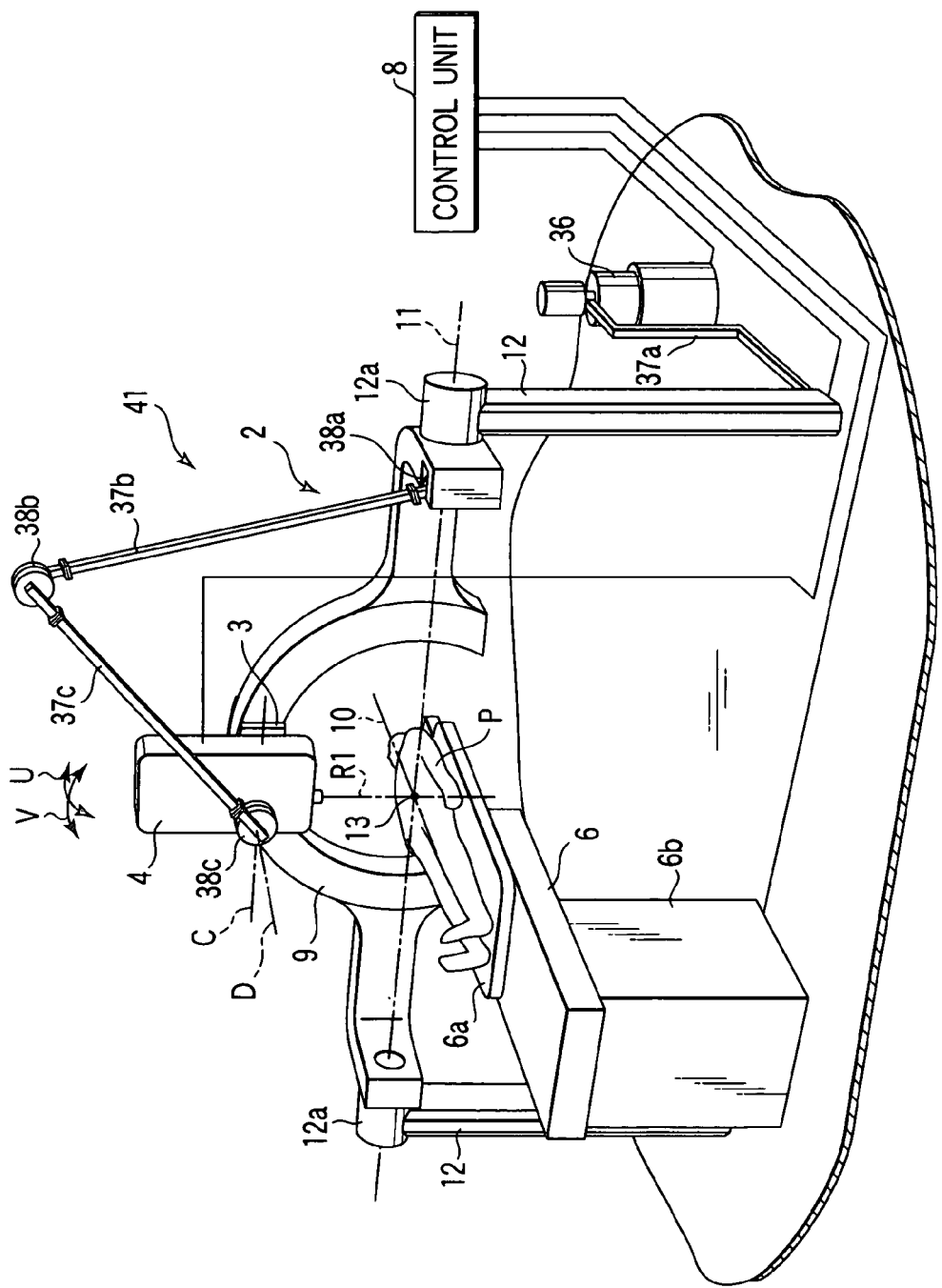
FIG. 3 is a perspective view showing a radiation treatment apparatus according to a second embodiment of the invention.

In a radiation treatment apparatus 41 shown in FIG. 3, like the radiation treatment apparatus 1 shown in FIG. 1, a guide 9 is rotated about a turning axis 11 that horizontally passes through an isocenter 13. The guide 9 is supported on support members 12 on both sides of the isocenter 13. In short, the radiation treatment apparatus 41 is of the Ω-type, wherein both ends thereof are supported.

The radiation treatment apparatus 41 differs from the radiation treatment apparatus 1 of FIG. 1 in that a microwave source 36 for supplying microwaves is disposed apart from the radiation generating unit 4. Although not shown, a variable collimator and a diagnosis imager may be provided, like the radiation treatment apparatus 1.

Microwaves are supplied from the microwave source 36 to the vicinity of the radiation generating unit 4 through waveguides 37a, 37b and 37c and rotary RF couplers 38a, 38b and 38c. The arrangement of waveguides 37d and 37e near the radiation generating unit 4 will be described with reference to FIGS. 4 to 6. The other elements of the radiation treatment apparatus 41 are the same as those of the radiation treatment apparatus 1 shown in FIG. 1, and thus these elements are shown in FIG. 3 in a simplified manner.

The microwave source 36 shown in FIG. 3 is disposed near the support member 12. A Klystron or a magnetron, for instance, is used as the microwave source 36. As is shown in FIG. 3, the waveguide 37a extends from the microwave source 36 up to the turning axis 11 through the support member 12. A rotational part between the support member 12 and guide 9 is coupled by a rotary RF coupler (not shown).

The waveguides 37b and 37c between the guide 9 and the vicinity of the radiation generating unit 4 are arranged in a roundabout fashion so as to prevent interference with the patient P placed at the isocenter 13 when the radiation generating unit 4 is moved. In FIG. 3, the end portions of the respective waveguides 37b and 37c are coupled by the rotary RF couplers 38a, 38b and 38c that rotate on axes parallel to the rotational axis 10, and these end portions are moved in a plane parallel to the plane in which the radiation generating unit 4 moves. In FIG. 3, the guide 9 and radiation generating unit 4 are coupled by two waveguides 37b and 37c. Alternatively, these may be coupled by more waveguides.

Figure 4:
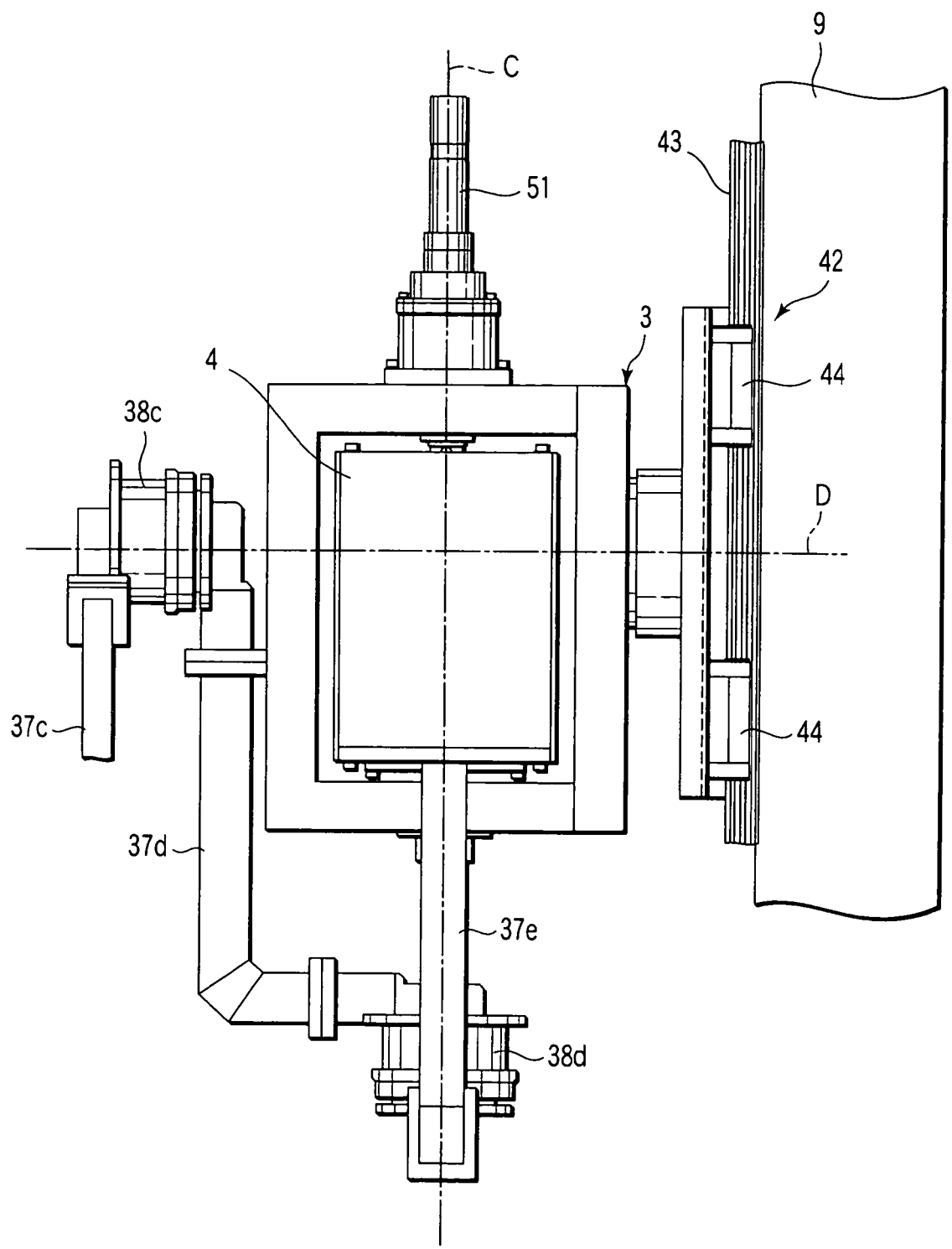
FIG. 4 is a top view of a region including a radiation generating unit and a movable member of the radiation treatment apparatus shown in FIG. 3.
Figure 5:
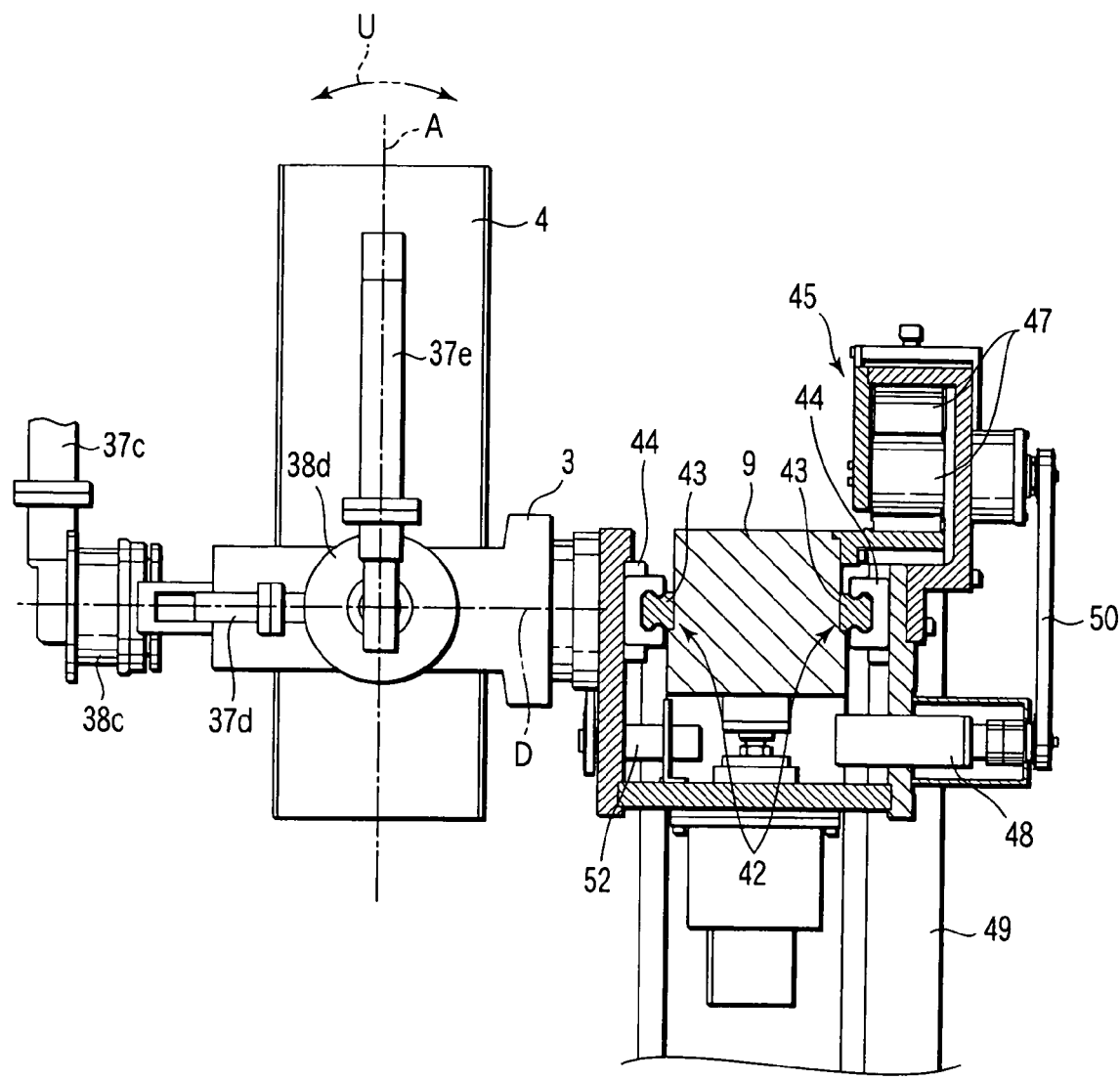
FIG. 5 is a side view of the region including the radiation generating unit and movable member of the radiation treatment apparatus shown in FIG. 3.

The rotational axis of the rotary RF coupler 38c attached to the end of the waveguide 37c on the radiation generating unit 4 side is disposed coaxial with the rotational axis D of the movable member 3, as shown in FIG. 4 or 5. Thereby, the waveguides 37b and 37c and rotary RF coupler 38b are made immovable when the radiation generating unit 4 is rotated on the rotational axis D. Even if the rotary RF coupler 38c is not disposed coaxial with the rotational axis D, no problem will occur with the operation of the radiation treatment apparatus 41.

Figure 6:
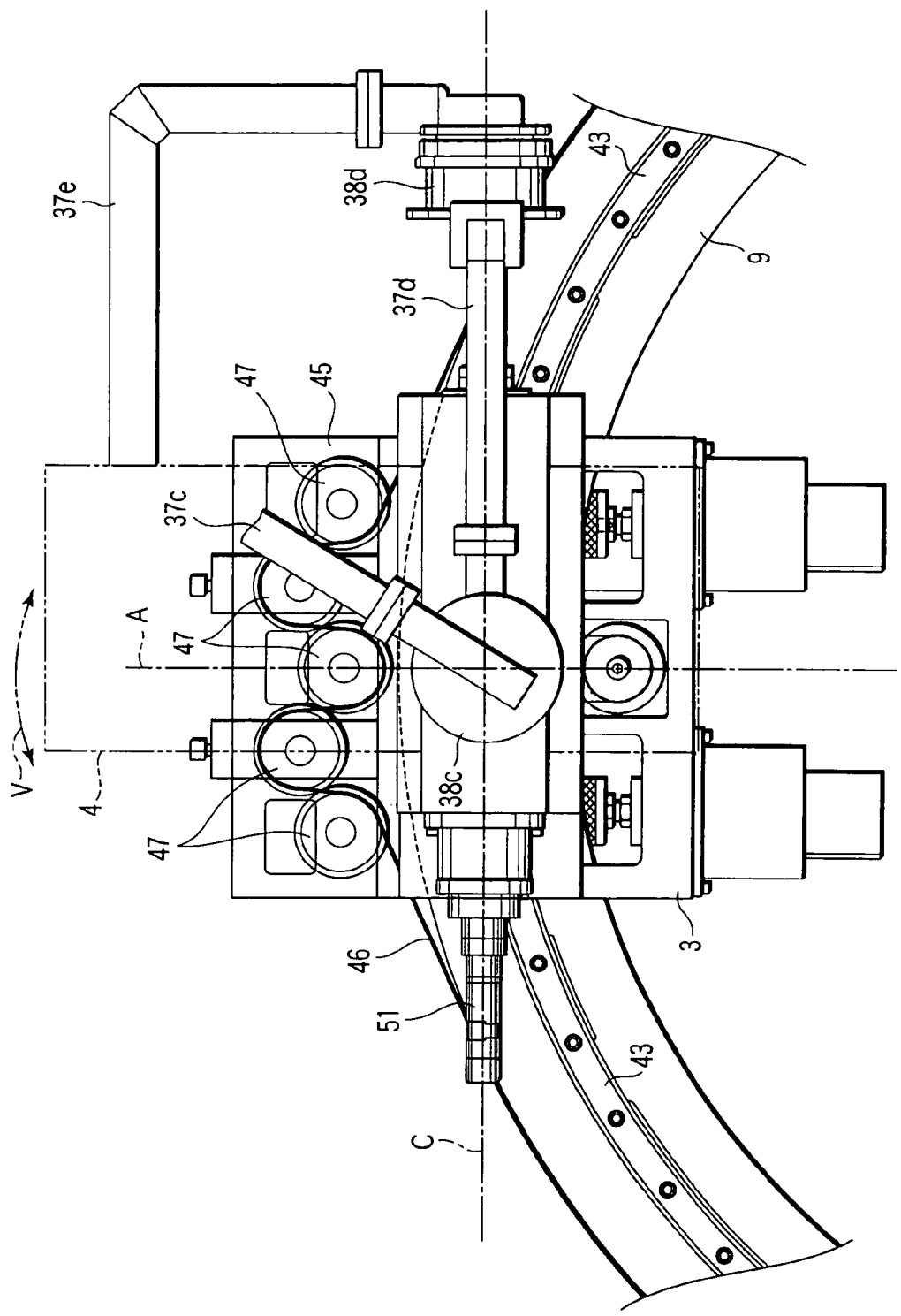
FIG. 6 is a front view of the region including the radiation generating unit and movable member of the radiation treatment apparatus shown in FIG. 3.

As is shown in FIG. 6, in order to rotate the radiation generating unit 4 about the rotational axis C, the rotary RF coupler 38c is connected to the waveguide 37d. The waveguide 37d extends along the periphery of the radiation generating unit 4 in a roundabout fashion and is connected to a rotary RF coupler 38d that rotates on the rotational axis C. The rotary RF coupler 38d is connected to the radiation generating unit 4 via the waveguide 37e.

With the above structure, microwaves propagate from the microwave source 36 to the radiation generating unit 4 through, in the named order, the waveguide 37a, the rotary RF coupler (not shown), rotary RF coupler 38a, waveguide 37b, rotary RF coupler 38b, waveguide 37c, rotary RF coupler 38c, waveguide 37d, rotary RF coupler 38d, and waveguide 37e. In the case where the angle of rotation is set to be sufficiently small, the rotary RF coupler 38c may be directly coupled to the radiation generating unit 4 over a flexible waveguide, instead of using the waveguides 37d and 37e and rotary RF coupler 38d.

As is shown in FIG. 5, a slide unit 42 is provided between the guide 9 and movable member 3. The slide unit 42 comprises rails 43 fixed on the guide 9 and sliders 44 fixed on the movable member 3. The rails 43 are formed concentrically on the rotational axis 10, as shown in FIG. 6. As is shown in FIG. 5, in this embodiment, a pair of rails 43 are provided on both sides, respectively. As is shown in FIG. 4, a plurality of sliders 44 are provided on the same rail 43. The slider 44 is a kind of bearing having circulating rolling elements. Since the rolling elements are arranged between the rail 43 and slider 44 without a gap, the movable member 3 can smoothly move.

The movable member 3 has a drive unit 45 shown in FIGS. 5 and 6. The drive unit 45 includes a belt 46 and running pulleys 47 shown in FIG. 6, and a motor 48 shown in FIG. 5. The running belt 46 is tensed around a bracket 49 that is provided in parallel with the outer periphery of the guide 9. The running belt 46 passes among a plurality of running pulleys 47 in a zigzag manner, as shown in FIG. 6. In order to adjust the tension of the running belt 46, the running pulleys 47 can move in the thickness direction of the running belt 46. One of the running pulleys 47 is coupled via a driving belt 50 to the motor 48 fixed to the movable member 3. When the running pulleys 47 are rotated by the motor 48, the pulleys 47 hold and pull the running belt 46. Thereby, the movable member 3 moves along the rails 43.

Since the drive unit 45 is the belt-drive mechanism which grips the belt 46 and moves, a position measuring sensor such as an inductosyn may advantageously be used to enhance the precision in positioning. In addition, the drive unit 45 may be a rack-and-pinion unit, etc.

The movable member 3 includes a servomotor 51 and a servo motor 52. The servomotor 51 is disposed on the rotational axis C and oscillates the radiation generating unit 4 directly or via a decelerator. The servomotor 52 is disposed in parallel with the rotational axis D and oscillates the radiation generating unit 4 by belt-driving. If the servo motor 51 is activated in the state in which the radiation generating unit 4 is set in a desired position by the manipulator 2, the radiation generating unit 4 and waveguide 37e rotate on the rotational axis C. Similarly, if the servomotor 52 is activated, the radiation generating unit 4 with servomotor 51, the waveguide 37e, rotary RF coupler 38d and waveguide 37d rotate on the rotational axis D.

According to the radiation treatment apparatus 41 of the second embodiment, the microwave source 36 is disposed apart from the radiation generating unit 4 and thus the radiation generating unit 4 is reduced in weight. Therefore, the bending of the entirety of the radiation treatment apparatus 41 is small, and the load on each driving device is reduced. Furthermore, the precision in positioning of the radiation generating unit 4 is enhanced.

A radiation treatment apparatus according to a third embodiment of the invention will now be described with reference to FIGS. 7, 4, 5 and 6. The same parts as those of the radiation treatment apparatuses 1 and 41 of the first and second embodiments are denoted by same reference numerals, and a description thereof is omitted.

Figure 7:
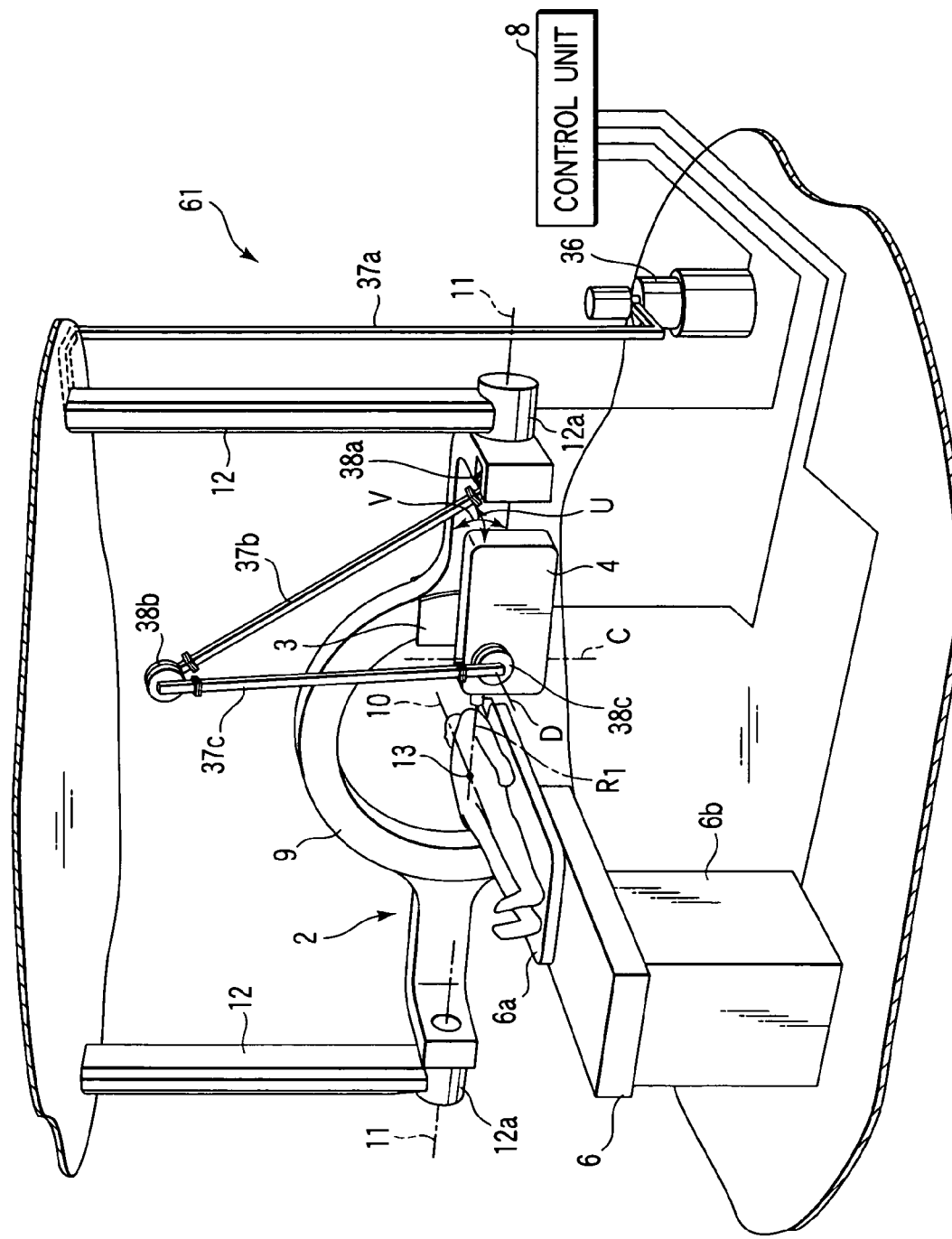
FIG. 7 is a perspective view showing a radiation treatment apparatus according to a third embodiment of the present invention.

In a radiation treatment apparatus 61 shown in FIG. 7, like the radiation treatment apparatus 41 shown in FIG. 3, the guide 9 is rotated about the turning axis 11 that horizontally passes through the isocenter 13. The microwave source 36 is disposed on the floor, apart from the radiation generating unit 4. The guide 9 is supported on support members 12 on both sides of the isocenter 13. In short, the radiation treatment apparatus 61 has the Ω-shaped appearance, wherein both ends thereof are supported.

The radiation treatment apparatus 61 differs from the radiation treatment apparatus 41 shown in FIG. 3 with respect to the arrangement of the support members 12. The support members 12 are fixed to the ceiling and support the manipulator 2 such that the manipulator 2 is suspended from the ceiling. The waveguide 37*a*, which passes through the support member 12, extends first up to the ceiling and then reaches the rotary RF coupler (not shown) situated on the turning axis 11. Alternatively, the waveguide 37*a*, without being extended up to the ceiling, may be passed into the support member 12 from a given portion thereof.

With the radiation treatment apparatus 61 having the above structure, the support members 12 are fixed to the ceiling. Thus, preparatory works, etc. can easily be done prior to the radiation treatment. In addition, the space on the floor can effectively be used.

With respect to the improvement in work efficiency and the effective use of space on the floor, it should suffice if the support members 12 are disposed at a position on the ceiling side relative to the plane horizontally extending through the isocenter 13. In addition, the radiation treatment apparatus 61 may be designed such that it can be retracted, when not in use, to the ceiling side by means of the support members 12.

A radiation treatment apparatus 71 according to a fourth embodiment of the invention will now be described with reference to FIGS. 8, 4, 5 and 6. The same parts as those of the radiation treatment apparatuses 1, 41 and 61 of the first to third embodiments are denoted by same reference numerals, and a description thereof is omitted.

Figure 8:
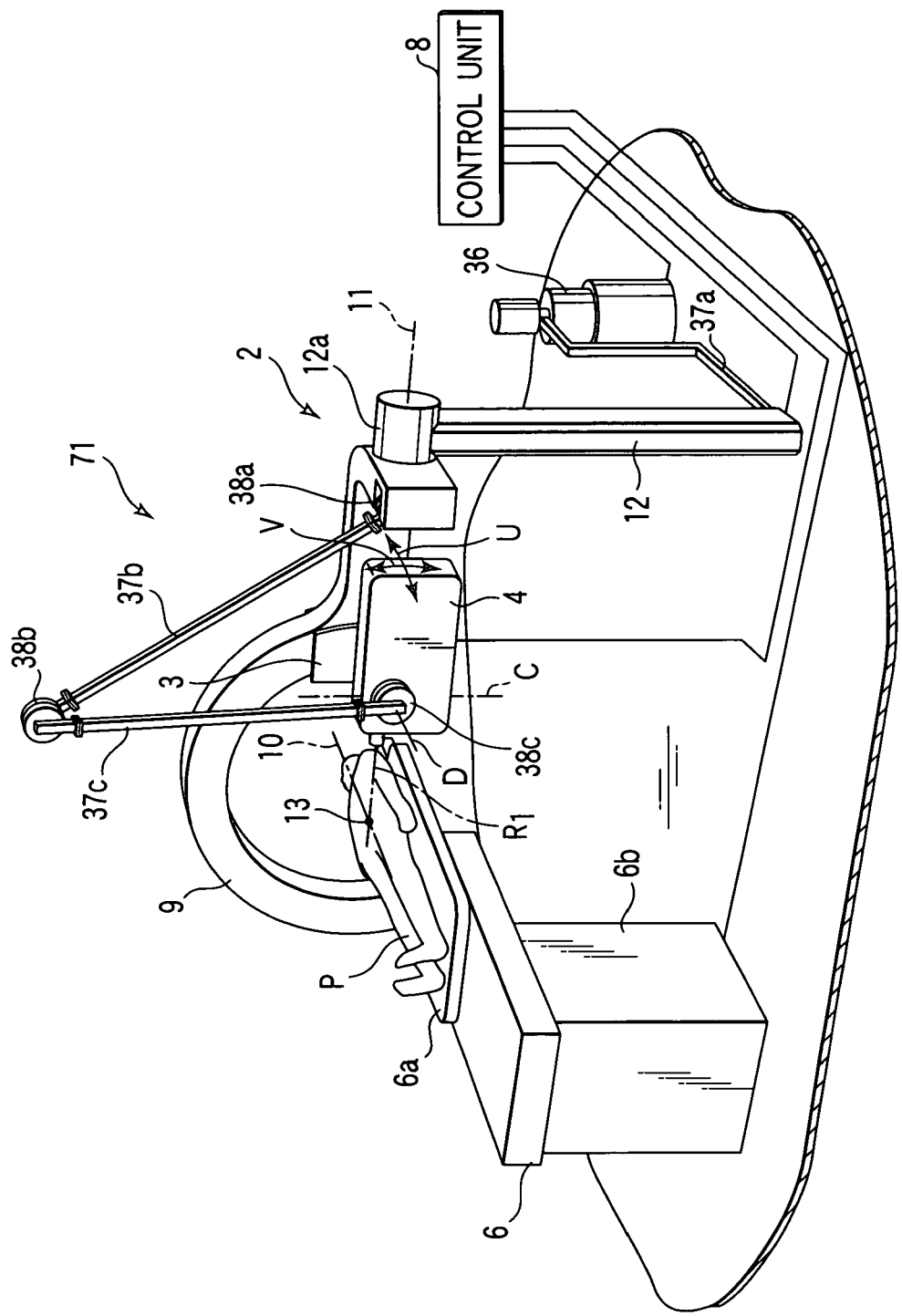
FIG. 8 is a perspective view showing a radiation treatment apparatus according to a fourth embodiment of the present invention.

In the radiation treatment apparatus 71 shown in FIG. 8, like the radiation treatment apparatus 41 shown in FIG. 3, the guide 9 is rotated about the turning axis 11 that horizontally passes through the isocenter 13. In the radiation treatment apparatus 41 shown in FIG. 3, the guide 9 is supported on support members 12 on both sides of the isocenter 13. By contrast, in the radiation treatment apparatus 71, unlike the other embodiments, the guide 9 is supported by the support member 12 at one part on the turning axis 11 extending through the isocenter 13. In short, the radiation treatment apparatus 71 has a cantilever-configuration and the Ω-shaped appearance.

In the radiation treatment apparatus 71, the support member 12 supports the guide 9 on one side. Consequently, if the radiation generating unit 4 moves far from the support member 12, the guide 9 bends. In the radiation treatment apparatus 71, the angle of application of radiation on the isocenter 13 is determined by moving the radiation generating unit 4 along the guide 9 and by turning the guide 9. In brief, the angle of radiation on the isocenter 13 in the radiation treatment apparatus 71 is determined by two variables relating to the rotational angles on the rotational axis 10 and turning axis 11. In the radiation treatment apparatus 71, the position of radiation is determined in one-to-one correspondence with the angle of radiation. Since there is reproducibility in bending of the guide 9 relative to a given angle of radiation, such bending can easily be corrected. Accordingly, in the radiation treatment apparatus 71, the radiation generating unit 4 can be positioned precisely with high reproducibility, and X-ray $R_1$ can be applied. Moreover, the radiation treatment apparatus 71, which has the cantilever-configuration, is smaller in size than the radiation treatment apparatus that is supported on both sides.

A radiation treatment apparatus 81 according to a fifth embodiment of the invention will now be described with reference to FIGS. 9, 4, 5 and 6. The same parts as those of the radiation treatment apparatuses 1, 41, 61 and 71 of the first to fourth embodiments are denoted by same reference numerals, and a description thereof is omitted.

Figure 9:
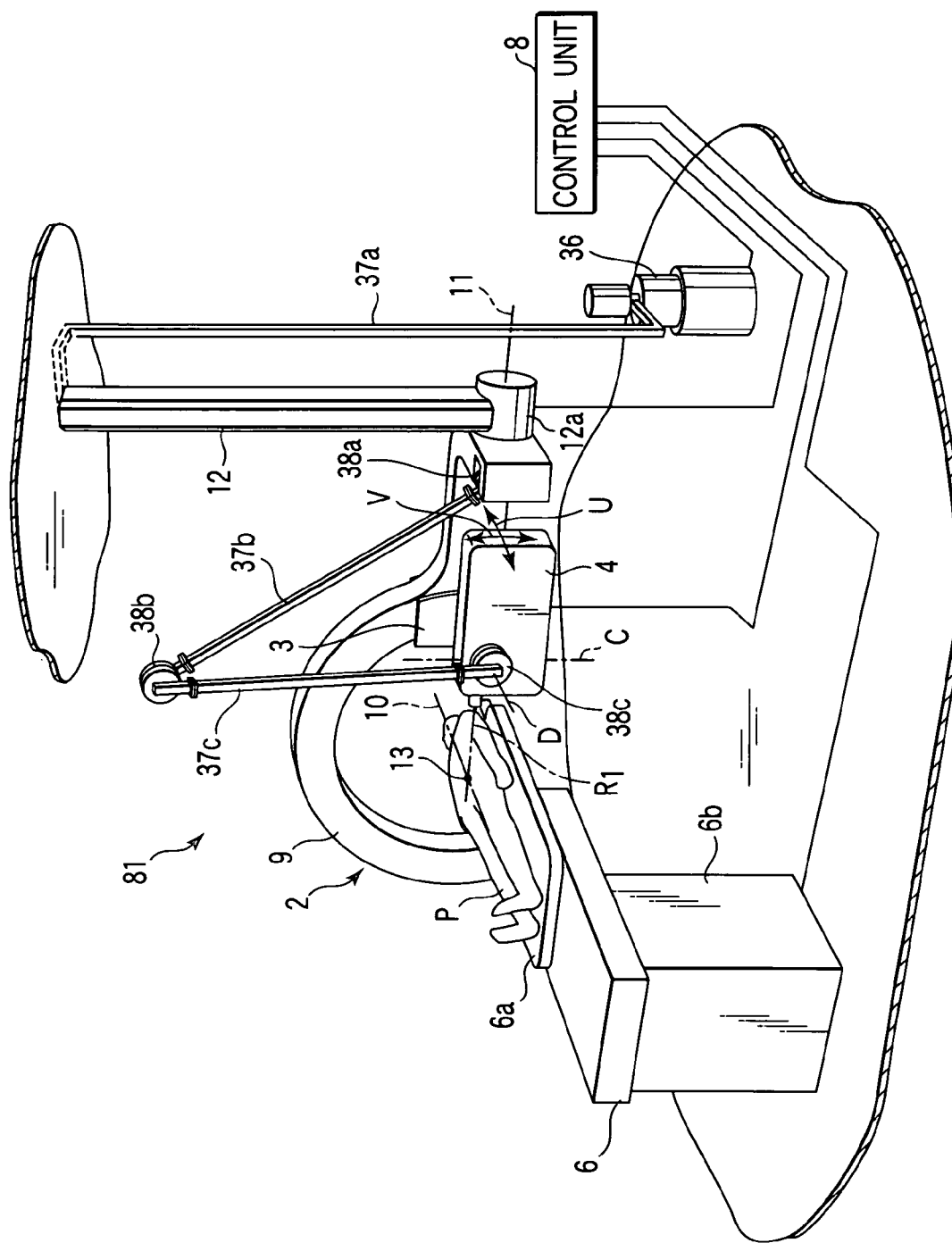
FIG. 9 is a perspective view showing a radiation treatment apparatus according to a fifth embodiment of the present invention.

In the radiation treatment apparatus 81 shown in FIG. 9, like the radiation treatment apparatuses shown in FIGS. 1, 3, 7 and 8, the guide 9 is rotated about the turning axis 11 that horizontally passes through the isocenter 13. Like the radiation treatment apparatus 71 shown in FIG. 8, the guide 9 is supported on one side. In addition, the support member 12 is fixed to the ceiling, like the radiation treatment apparatus 61 shown in FIG. 7. The microwave source 36 is disposed on the floor, apart from the radiation generating unit 4. In short, the radiation treatment apparatus 81 has a cantilever-configuration and the Ω-shaped appearance wherein the apparatus 81 is suspended from the ceiling.

The radiation treatment apparatus 81 can perform the same functions as the radiation treatment apparatus 1 or the radiation treatment apparatus 41, and has the advantages as both the radiation treatment apparatus 61 and radiation treatment apparatus 71.

A radiation treatment apparatus 91 according to a sixth embodiment of the invention will now be described with reference to FIGS. 10, 4, 5 and 6. The same parts as those of the radiation treatment apparatuses 1, 41, 61, 71 and 81 of the first to fifth embodiments are denoted by same reference numerals, and a description thereof is omitted.

Figure 10:
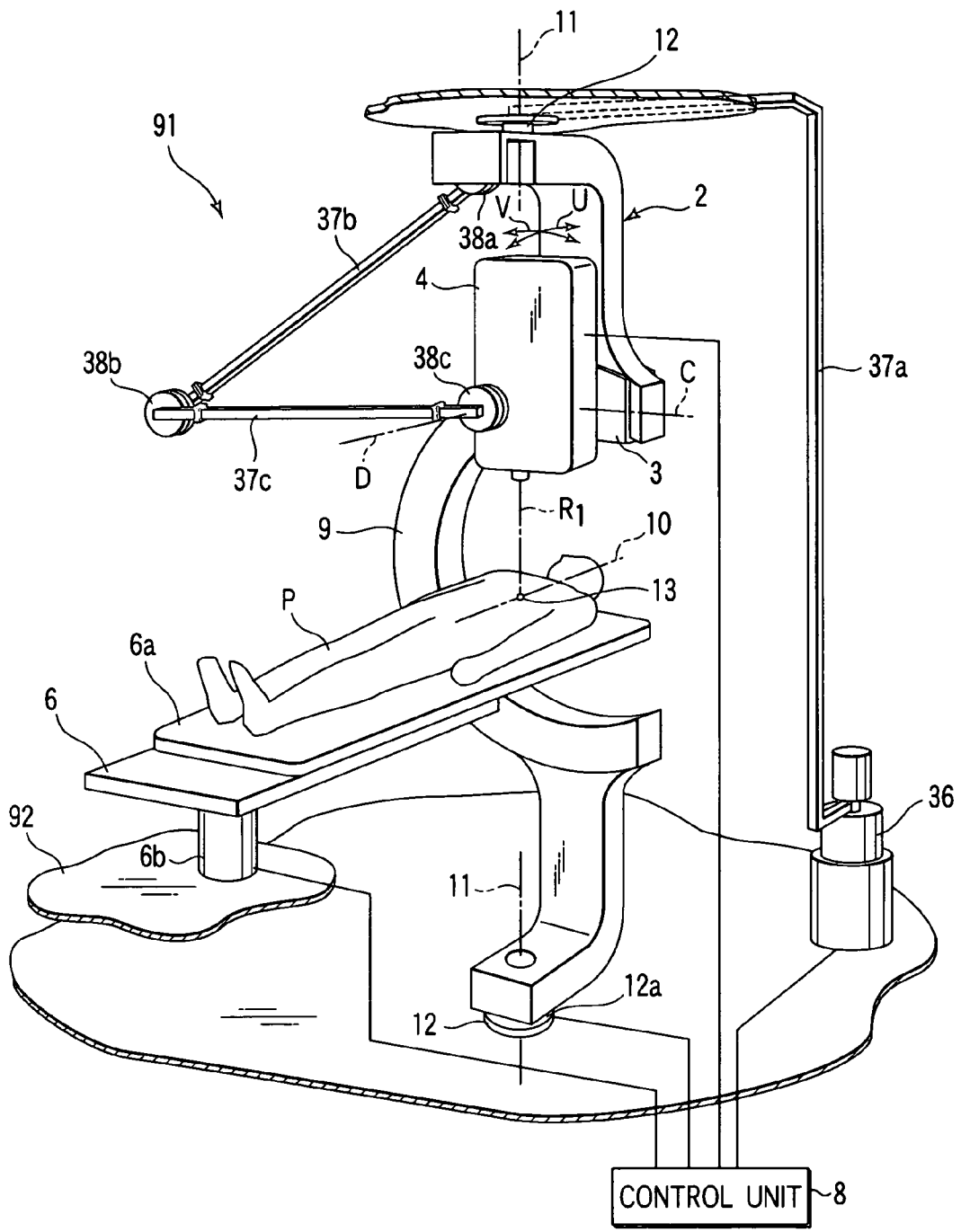
FIG. 10 is a perspective view showing a radiation treatment apparatus according to a sixth embodiment of the present invention.

In the radiation treatment apparatus 91 shown in FIG. 10, the guide 9 is rotated about a turning axis 11 vertically extending through the isocenter 13. The guide 9 is supported on support members 12 provided on the ceiling and the floor, on both sides of the isocenter 13 on the turning axis 11. The arcuate guide 9 is disposed in what is called C-shape.

The microwave source 36 is disposed on the floor, apart from the radiation generating unit 4. Microwaves are supplied from the ceiling side to the radiation generating unit 4 through waveguides 37*a*, 37*b*, 37*c*, 37*d* and 37*e* and rotary RF couplers 38*a*, 38*b*, 38*c* and 38*d*. Alternatively, microwaves may be supplied from the floor side.

The Ω-shaped guide 9 of the radiation treatment apparatus, as represented by the radiation treatment apparatus 1 of the first embodiment, requires provision of the counterweight 14 to reduce the load on the servo motor 12*a* in the environment in which the gravity acts. On the other hand, in the radiation treatment apparatus 91, when the guide 9 is rotated, the center of gravity moves in the horizontal direction. In addition, when the guide 9 is in the stationary state, no load acts on the servo motor 12*a*. Thus, in the radiation treatment apparatus 91, there is no need to provide the guide 9 with the counterweight 14.

In the radiation treatment apparatus 91, the radiation generating unit 4 is movable to a position below the patient P, so the rotational axis 10 is positioned high above the floor. There is a case where the patient P may feel uncomfortably when the movable table is raised. To prevent this, a second floor 92 is provided above the floor where the manipulator 2 is installed, and the movable table 6 is situated on the second floor 92. The microwave source 36 may be disposed below the second floor 92.

Since the support members 12 are disposed on the ceiling and the floor, the radiation treatment apparatus 91 allows effective use of the surrounding space. Furthermore, the guide 9 of radiation treatment apparatus 91 is less bent since the weight of the guide 9 in the vertical direction is supported by the support members 12 vertically disposed on the ceiling and the floor.

A radiation treatment apparatus 101 according to a seventh embodiment of the invention will now be described with reference to FIGS. 11, 4, 5 and 6. The same parts as those of the radiation treatment apparatuses 1, 41, 61, 71, 81 and 91 of the first to sixth embodiments are denoted by same reference numerals, and a description thereof is omitted.

Figure 11:
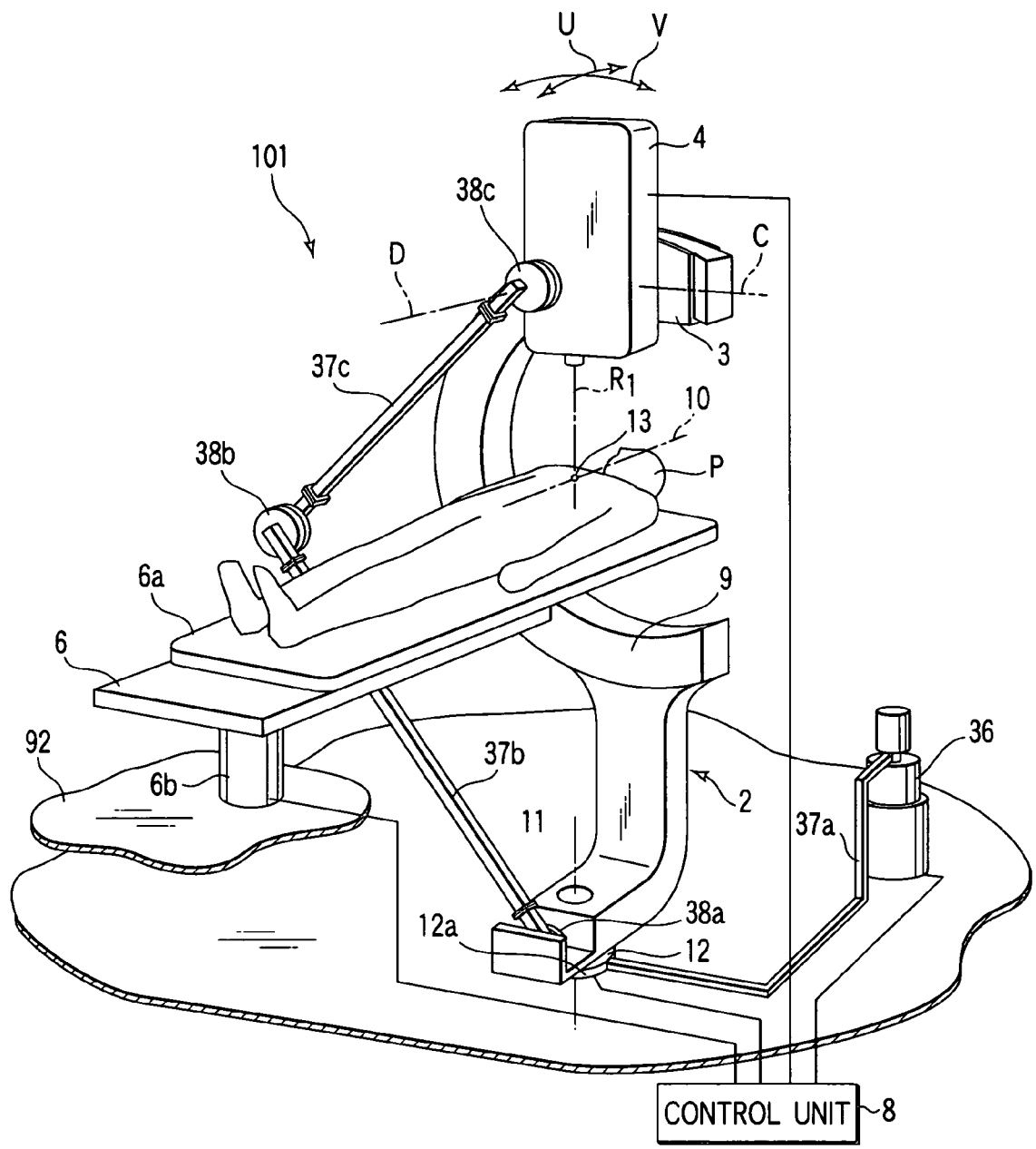
FIG. 11 is a perspective view showing a radiation treatment apparatus according to a seventh embodiment of the present invention.

In the radiation treatment apparatus 101 shown in FIG. 11, like the radiation treatment apparatus 91 shown in FIG. 10, the guide 9 is rotated about the turning axis 11 vertically extending through the isocenter 13. The radiation treatment apparatus 101 differs from the radiation treatment apparatus 91 shown in FIG. 10 in that the guide 9 is supported on the support member 12 provided on the floor and microwaves are supplied to the radiation generating unit 4 from the floor side. In short, the radiation treatment apparatus 91 shown in FIG. 10 has the C-shaped appearance wherein it is supported on both sides, whereas the radiation treatment apparatus 101 shown in FIG. 11 has the C-shaped appearance wherein it is supported on the floor side alone.

The radiation treatment apparatus 101 has a cantilever configuration. Hence, when the radiation generating unit 4 has moved to the ceiling side, away from the support member 12, the guide 9 will bend. When the radiation generating unit 4 is positioned by the manipulator 2 at a desired angle of radiation relative to the isocenter 13, the angle of radiation is determined in one-to-one correspondence by the two variables relating to the rotational angles on the rotational axis 10 and turning axis 11.

In this case, the bending of the guide 9 varies when the radiation generating unit 4 moves along the guide 9, and it does not vary when the guide 9 turns about the turning axis 11. In other words, it should suffice if the bending of the guide 9 is corrected with respect to only the rotational angle of the radiation generating unit 4 that moves about the rotational axis 10.

Thus, according to the radiation treatment apparatus 101, the bending of the guide 9 can easily be corrected and high precision in positioning can be attained. Moreover, with provision of a second floor at a proper height, for example, the microwave propagation path comprising the radiation generating unit 4, support member 12, microwave source 36, waveguides and rotary RF couplers can be hidden under the second floor when the radiation treatment apparatus 101 is not in use.

A radiation treatment apparatus 111 according to an eighth embodiment of the invention will now be described with reference to FIGS. 12, 4, 5 and 6. The same parts as those of the radiation treatment apparatuses 1, 41, 61, 71, 81, 91 and 101 of the first to seventh embodiments are denoted by same reference numerals, and a description thereof is omitted.

Figure 12:
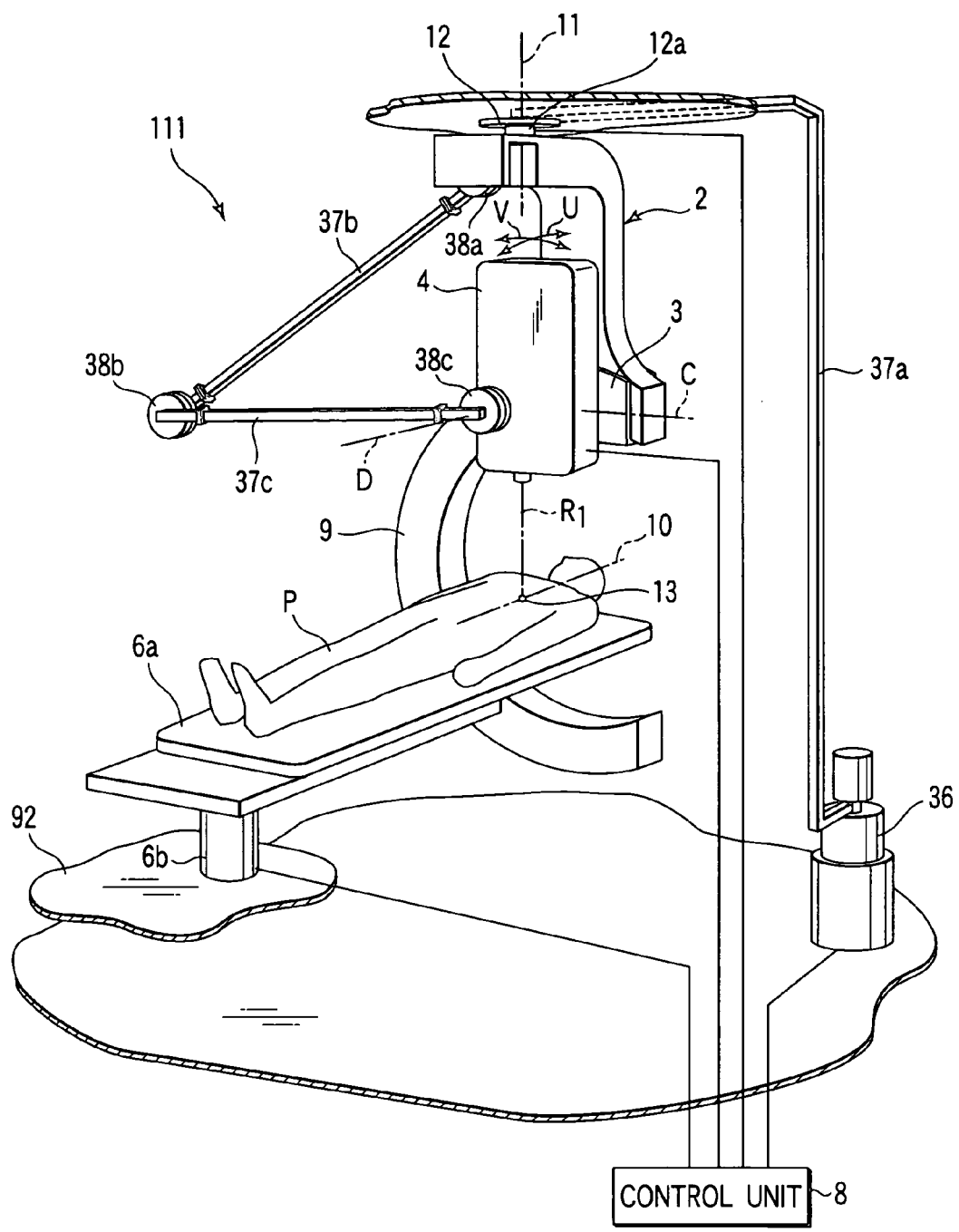
FIG. 12 is a perspective view showing a radiation treatment apparatus according to an eighth embodiment of the present invention.

In the radiation treatment apparatus 111 shown in FIG. 12, like the radiation treatment apparatuses 91 and 101 shown in FIGS. 10 and 11, the guide 9 is rotated about the turning axis 11 vertically extending through the isocenter 13. The radiation treatment apparatus 111 differs from the radiation treatment apparatus 101 in that the guide 9 is supported on the support member 12 provided on the ceiling. In the radiation treatment apparatus 111, like the radiation treatment apparatus 91, microwaves are supplied via the ceiling side. In short, the radiation treatment apparatus 111 has the C-shaped appearance wherein it is supported on the ceiling side alone.

The radiation treatment apparatus 111, like the radiation treatment apparatus 101, has a cantilever configuration. Hence, when the radiation generating unit 4 moves along the guide 9, the guide 9 will bend. However, for the same reason as stated in connection with the radiation treatment apparatus 101, correction can easily be made in the radiation treatment apparatus 111. Moreover, since the radiation treatment apparatus 111 is suspended from the ceiling, the surrounding space on the second floor can effectively be used.

A radiation treatment apparatus 121 according to a ninth embodiment of the invention will now be described with reference to FIG. 13. The same parts as those of the radiation treatment apparatuses 1, 41, 61, 71, 81, 91, 101 and 111 of the first to eighth embodiments are denoted by same reference numerals, and a description thereof is omitted.

Figure 13:
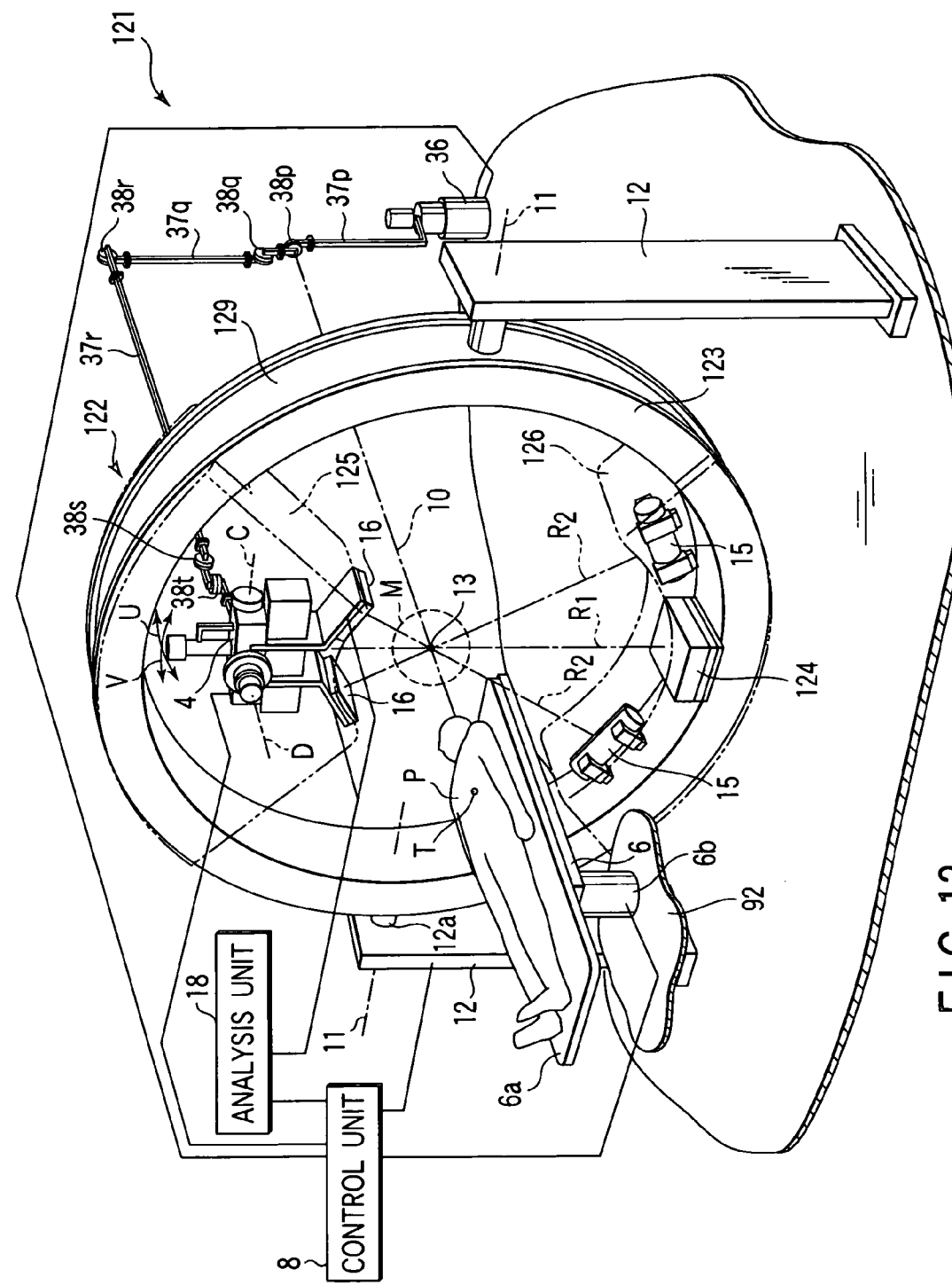
FIG. 13 is a perspective view showing a radiation treatment apparatus according to a ninth embodiment of the present invention.

The radiation treatment apparatus 121 shown in FIG. 13 comprises a manipulator 122, a radiation generating unit 4, a movable table 6, a diagnosis imager, and a control unit 8. The manipulator 122 comprises a movable member 123, a guide 129 and support members 12. The diagnosis imager comprises a plurality of pairs of radiation sources 15 and detectors 16. In this embodiment, the diagnosis imager comprises two pairs of radiation sources 15 and detectors 16.

The movable member 123 and guide 129 are formed in annular shapes. The movable member 123 is provided inside the guide 129. The slide unit 42 shown in FIG. 5 is mounted between the movable member 123 and guide 129. The movable member 123 rotates about the rotational axis 10.

The radiation generating unit 4, radiation sources 15 and detectors 16 are arranged inside the movable member 123. The radiation generating unit 4 is supported on the movable member 123 on rotational axes C and D crossing the direction of emission of the X-ray $R_1$. The radiation generating unit 4 rotates in a U-direction and a V-direction on the rotational axes C and D, respectively. The isocenter 13 is set at a point where the X-ray $R_1$ emitted from the radiation generating unit 4 intersects at right angles with the rotational axis 10.

The support members 12 rotate the guide 129 about a turning axis 11 that horizontally extends through the isocenter 13. Thus, the radiation treatment apparatus 121 can position the radiation generating unit 4 at a given point on a spherical surface, and can apply the X-ray $R_1$ in multiple directions with a focus set at the isocenter 13. The support members 12 are disposed at two portions on the turning axis 11, that is, on opposed external sides of the guide. The support members 12 are fixed on the floor. In short, the radiation treatment apparatus 121 has an O-shaped appearance wherein both sides thereof are supported in the horizontal direction.

The radiation sources 15 are arranged such that X-rays $R_2$ may cross at the isocenter 13. The radiation sources 15 are disposed at remote positions from the radiation generating unit 4 so that the X-rays $R_2$ to be detected may not interfere with the X-ray $R_1$ emitted from the radiation generating unit 4. The detectors 16 are situated at such positions as to detect X-rays $R_2$ emitted from the associated radiation sources 15. A beam stopper 124 for shutting off the X-ray $R_1$ is disposed at a position which is in symmetry with the radiation generating unit 4 with respect to the isocenter 13. The radiation generating unit 4 and detectors 16, except detection surfaces of the detectors 16, are covered with a hood 125. The radiation sources 15 and beam stopper 124 are covered with a hood 126.

The radiation generating unit 4 is supplied with microwaves from the microwave source 36 that is disposed apart from the manipulator 122. Microwaves are propagated to the vicinity of the radiation generating unit 4 through waveguides 37$p$, 37$q$ and 37$r$ and rotary RF couplers 38$p$, 38$q$, 38$r$, 38$s$ and 38$t$. The rotary RF coupler 38$p$ is situated on an axis extending through the isocenter 13. The waveguides and rotary RF couplers near the radiation generating unit 4 are arranged in the same fashion as those shown in FIGS. 4 to 6, and a description thereof is omitted.

In the radiation treatment apparatus 121 with the above-described structure, the guide 129 and movable member 123 are formed in annular shapes. Accordingly, when the radiation generating unit 4 has been moved along the guide, the degree of deformation of the guide 129 is small. Thus, the radiation generating unit 4 can precisely positioned with simple correction. In addition, like the radiation treatment apparatuses according to the first to eighth embodiments, the radiation treatment apparatus 121 can apply X-rays $R_1$ in multiple directions without altering the attitude of the patient P. Furthermore, according to the radiation treatment apparatus 121, the object of radiation can be confirmed by the diagnosis imager and the X-ray $R_1$ can be applied to the object of radiation departing from the isocenter 13 by varying the direction of radiation of the radiation generating unit 4 about the rotational axes C and D. A balancer weight may be attached to a desired position of the movable member 123, in order to set the center of gravity of the movable member 123 that is eccentric by being attached the radiation generating unit 4 etc. at the isocenter 13. Thus, the load on driving devices attached to the movable member 123 can be reduced.

A radiation treatment apparatus 131 according to a tenth embodiment of the invention will now be described with reference to FIG. 14. The same parts as those of the radiation treatment apparatuses 1, 41, 61, 71, 81, 91, 101, 111 and 121 of the first to ninth embodiments are denoted by same reference numerals, and a description thereof is omitted.

Figure 14:
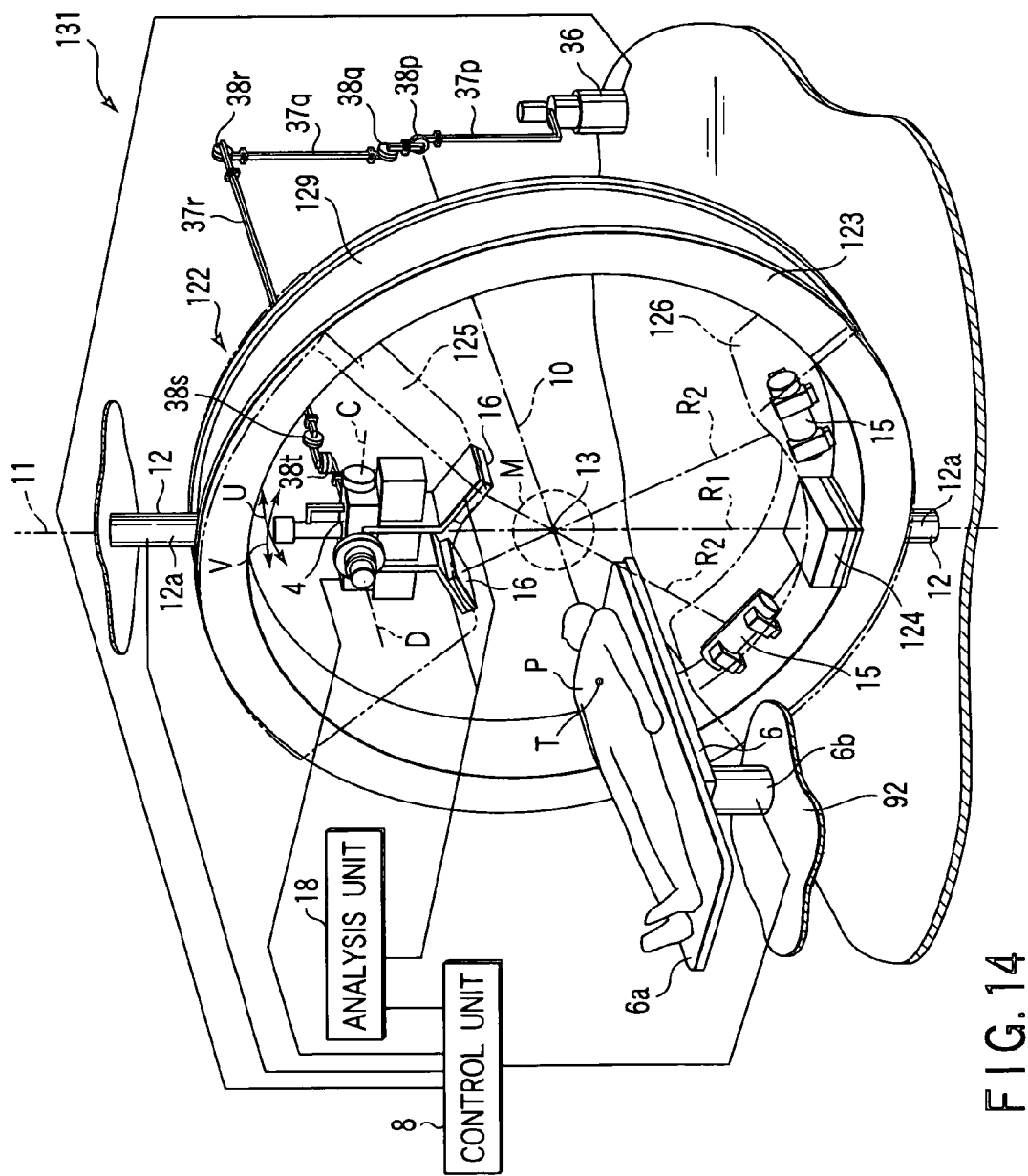
FIG. 14 is a perspective view showing a radiation treatment apparatus according to a tenth embodiment of the present invention.

In the radiation treatment apparatus 131 shown in FIG. 14, the guide 129 is rotated about the rotational axis 10 vertically extending through the isocenter 13. In this respect, the radiation treatment apparatus 131 differs from the radiation treatment apparatus 121 shown in FIG. 13. The support members 12 are disposed on the ceiling and the floor, and a servo motor 12$a$ is provided. In short, the radiation treatment apparatus 131 has the O-shaped appearance wherein it is vertically supported on both sides.

Since the turning axis 11 is set to be vertical, no load that deforms the guide 129 in an outward direction of the plane thereof acts on the guide 129 even if the radiation generating unit 4 moves. Thus, the radiation treatment apparatus 131 can apply the X-ray $R_1$ to the focus T with high precision, by correcting deformation in the in-plane direction of the guide 129.

A radiation treatment apparatus 141 according to an eleventh embodiment of the invention will now be described with reference to FIG. 15. The same parts as those of the radiation treatment apparatuses 1, 41, 61, 71, 81, 91, 101, 111, 121 and 131 of the first to tenth embodiments are denoted by same reference numerals, and a description thereof is omitted.

Figure 15:
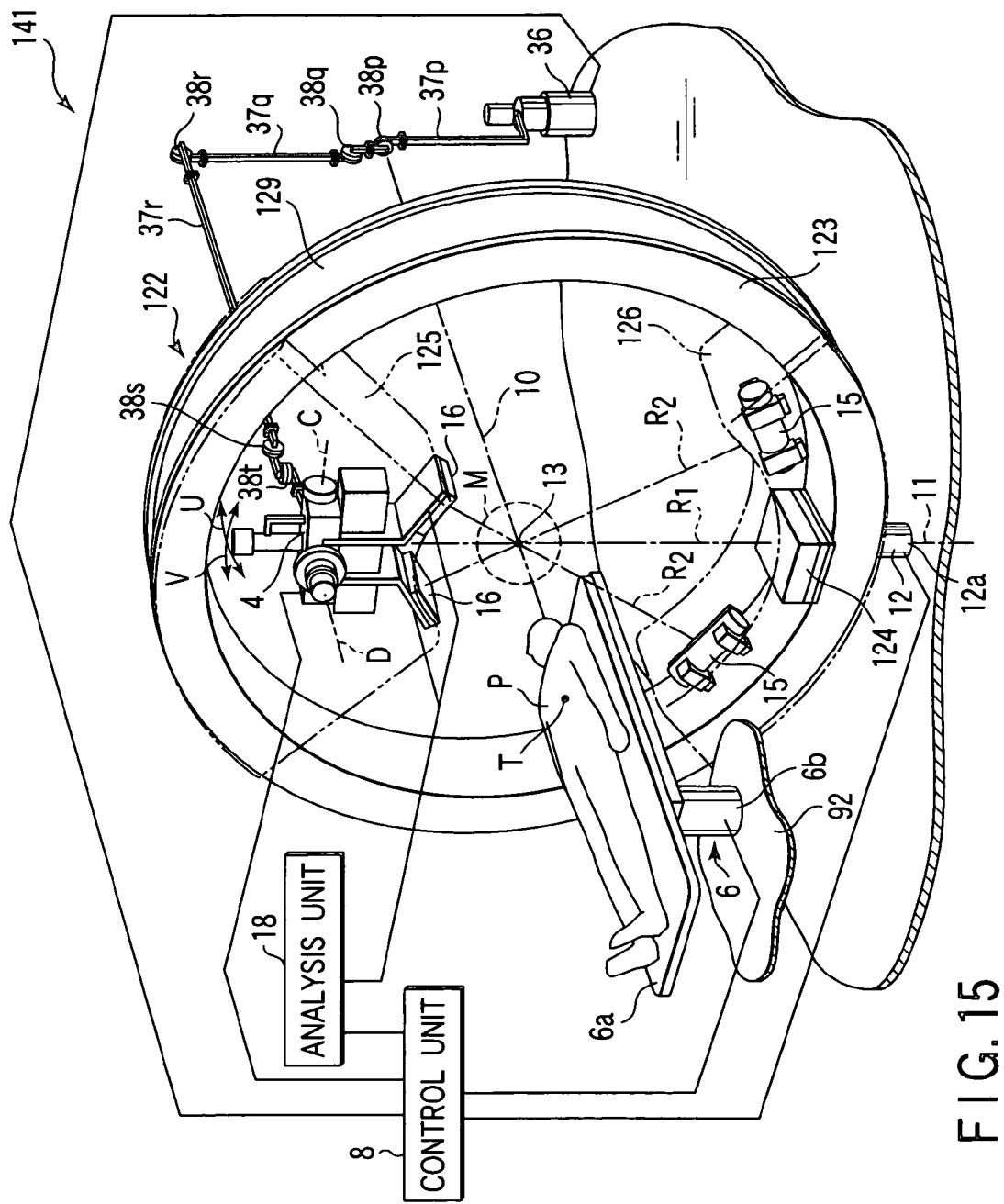
FIG. 15 is a perspective view showing a radiation treatment apparatus according to an eleventh embodiment of the present invention.

The radiation treatment apparatus 141 shown in FIG. 15 differs from the radiation treatment apparatus 131 shown in FIG. 14 in that the guide 129 is supported at one portion on the floor. In short, the radiation treatment apparatus 141 has the O-shaped appearance wherein it is vertically supported on the floor side.

The radiation treatment apparatus 141 does not have a support member on the ceiling side. Thus, it can be installed without a work for reinforcing the ceiling.

A radiation treatment apparatus 151 according to a twelfth embodiment of the invention will now be described with reference to FIG. 16. The same parts as those of the radiation treatment apparatuses 1, 41, 61, 71, 81, 91, 101, 111, 121, 131 and 141 of the first to eleventh embodiments are denoted by same reference numerals, and a description thereof is omitted.

Figure 16:
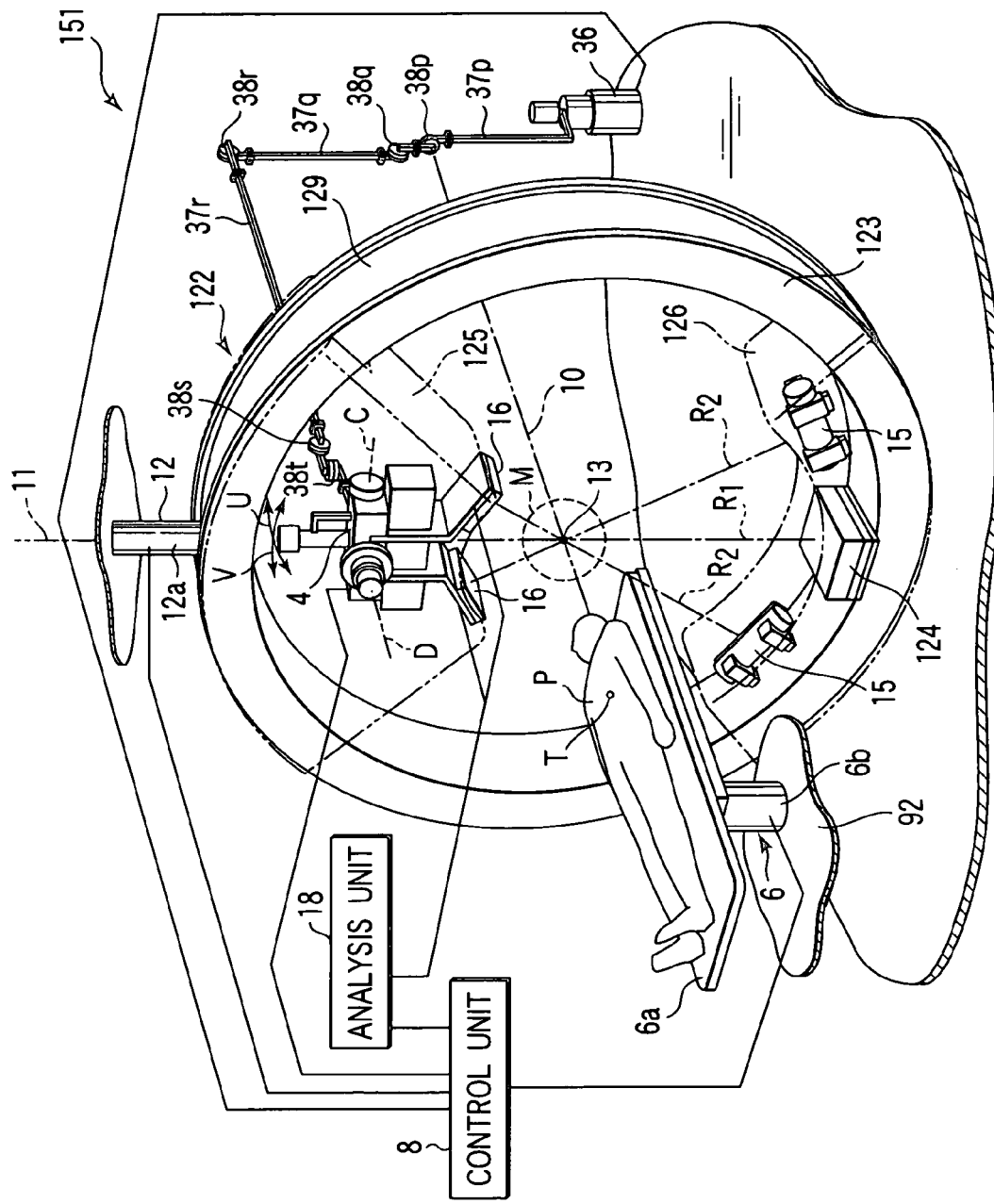
FIG. 16 is a perspective view showing a radiation treatment apparatus according to a twelfth embodiment of the present invention.

The radiation treatment apparatus 151 shown in FIG. 16 differs from the radiation treatment apparatuses 131 and 141 shown in FIGS. 14 and 15 in that the guide 129 is supported at one portion on the ceiling side. In short, the radiation treatment apparatus 151 has the O-shaped appearance wherein it is vertically supported on the ceiling side. In the radiation treatment apparatus 151, the manipulator 122 is disposed to be suspended from the ceiling, and the center of gravity of the guide 129, etc. is located below the support member 12. Thus, the radiation treatment apparatus 151 is easily stabilized in the stationary state.

A radiation treatment apparatus 31 according to a 13th embodiment of the invention will now be described with reference to FIG. 17. The same parts as those of the radiation treatment apparatuses 1, 41, 61, 71, 81, 91, 101, 111, 121, 131, 141 and 151 of the first to twelfth embodiments are denoted by same reference numerals, and a description thereof is omitted.

Figure 17:
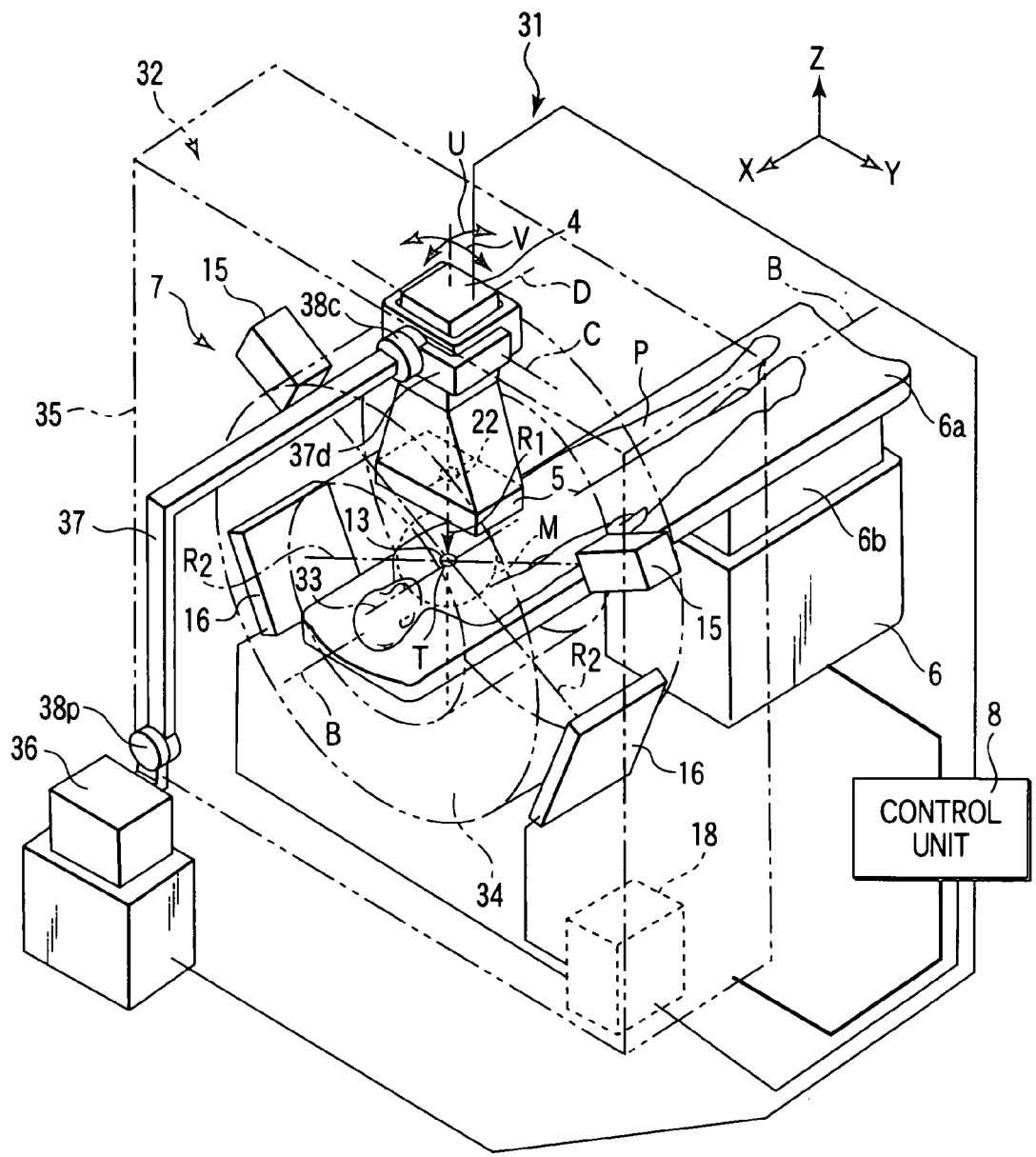
FIG. 17 is a perspective view showing a radiation treatment apparatus according to a 13th embodiment of the present invention.

The radiation treatment apparatus 31 shown in FIG. 17 comprises a gantry 32, a radiation generating unit 4, a variable collimator 5, a movable table 6 and a diagnosis imager 7. The gantry 32 includes a drum 34 that is rotatable about a rotational axis 33, and a frame 35 that supports the drum 34. The drum 34 is one form of the movable member. The drum 34 is provided with the radiation generating unit 4 and radiation sources 15 and detectors 16 of the diagnosis imager 7, which are arranged in a proper configuration. A hollow part of the drum 34 has such a size as to accommodate a slide board 6$a$ of the movable table 6 on which the patient P is placed in a direction along the rotational axis 33.

The radiation generating unit 4 is supported on rotational axes C and D so as to emit an X-ray $R_1$ toward the rotational axis 33. The rotational axes C and D are arranged so as to intersect at right angles with each other. The rotational axes C and D permit rotation of the radiation generating unit 4 in a U-direction along the rotational axis 33 and in a V-direction crossing the rotational axis 33. In short, the radiation generating unit 4 can perform what is called "swinging" operation on the rotational axes C and D.

The radiation generating unit 4 has a microwave source 36 disposed apart from the dram 34. Microwaves are supplied via waveguides 37 and 37$d$ and rotary RF couplers 38$p$ and 38$c$. The variable collimator 5 is attached to the radiation generating unit 4, and is controlled by a control unit 8.

The radiation sources 15 are paired with the detectors 16 and are arranged such that the emitted X-rays $R_2$ may cross at the isocenter 13 on the rotational axis 33. The radiation sources 15 are fixed to the drum 34 and rotate along with the radiation generating unit 4. Therefore, their fields of radiation do not interfere with each other.

In the radiation treatment apparatus 31 according to the 13th embodiment which has the above-described structure, the patient P is placed on the movable table 6 and is inserted in the drum 34 along with the slide board 6$a$. A doctor or a radiation engineer positions a focus T of the patient P while confirming it by the diagnosis imager 7. On the basis of the position of the drum 34 of gantry 32, the angle of "swinging" movement of the radiation generating unit 4 and the three-dimensional position and shape of the focus T obtained by the diagnosis imager 7, the control unit 8 controls the variable collimator 5 and adjusts the irradiation field of X-ray $R_1$ in a tracking manner in accordance with the movement of the focus T.

In the radiation treatment apparatus 31, the irradiation field of X-ray $R_1$ is adjusted in a tracking manner in accordance with the three-dimensional position and shape of the focus T during the radiation treatment. Thus, even if the focus T moves during radiation treatment, the X-ray $R_1$ can be applied with high precision. According to the radiation treatment apparatus 31, the X-ray $R_1$ can successively be applied to the focus T that is moving during radiation treatment, and the dose of unnecessary radiation on non-diseased parts can be reduced.

If a CT scanner is used for the diagnosis imager 7 in the first to 13th embodiments, a three-dimensional position and a three-dimensional shape with high precision of the focus T can be obtained. Thus, the irradiation field of the X-ray $R_1$ can precisely be adjusted in accordance with the focus T in a tracking manner.

The imager and variable collimator are not illustrated in connection with the second to eighth embodiments. It is possible to provide the imager and variable collimator in the second to eighth embodiments, like the first embodiment. Thereby, the focus T, or the object of radiation of X-ray $R_1$, can be confirmed and the irradiation field can be adjusted in a tracking manner in accordance with the focus T.

Where the radiation treatment apparatus according to the present invention has the diagnosis imager and variable collimator, the three-dimensional position and shape of the object of treatment, which is subjected to radiation treatment, are detected by the diagnosis imager, and the variable collimator is controlled by the control unit on the basis of the three-dimensional position and shape of the object of treatment and the angle of application of treatment radiation. Thereby, the radiation treatment apparatus adjusts the field of application of treatment radiation in accordance with the object of treatment in a tracking manner. Thus, according to the radiation treatment apparatus, the field of application of radiation can precisely be adjusted in a tracking manner in accordance with the object of treatment that moves and changes its shape.

If an X-ray CT scanner is used for the diagnosis imager, the radiation treatment apparatus according to this invention can obtain a three-dimensional position and a three-dimensional shape with high precision of the object of treatment. Thus, the field of application of treatment radiation can precisely be adjusted in accordance with the object of treatment in a tracking manner.

In the control method for the radiation treatment apparatus according to the present invention, the diagnosis imager detects the three-dimensional position and three-dimensional shape of the object of treatment of the patient positioned within the range of detection of the diagnosis imager. Based on the angle of application of treatment radiation and the three-dimensional position and three-dimensional shape of the object of treatment which have been obtained by the diagnosis imager, the position and shape of the emission port of the variable collimator, which passes the treatment radiation through, are successively varied in accordance with the projection cross section of the object of treatment as viewed in the direction of application of the treatment radiation, in order to successively adjust the irradiation field of the treatment radiation in a tracking manner in accordance with the object of treatment. Therefore, medical treatment can be performed by precisely adjusting the irradiation field of radiation in a tracking manner in accordance with the object of treatment that moves and changes its shape.

In the first to 13th embodiments, the radiation treatment apparatus having the imager and variable collimator can confirm the object of treatment of the patient even during radiation treatment and can vary the shape of the irradiation field in accordance with the position and shape of the object of treatment. Therefore, according to the radiation treatment apparatus, the application of radiation on parts other than the object of radiation can be suppressed, the distribution of radiation dose can be controlled, and the precise radiation treatment can be performed.

Furthermore, according to the radiation treatment apparatuses according to the above-described embodiments of the invention, the imager can confirm the object of treatment, even in the circulatory system, digestive system or thereabouts, where constant movements occur due to heartbeats, respiratory movement, peristalsis, etc. In addition, the variable collimator can adjust the irradiation field of radiation in a tracking manner in accordance with the object of treatment. Therefore, the time of radiation treatment can be shortened, and the load on the patient reduced.

Besides, according to the radiation treatment apparatus of the present invention, even without moving the patient, the angle of application of treatment radiation can be altered and the focus to be subjected to radiation can be tracked. Thus, the patient may less frequently feel uncomfortable.

A radiation treatment apparatus 161 according to a 14th embodiment of the invention will now be described with reference to FIGS. 18 to 26.

Figure 18:
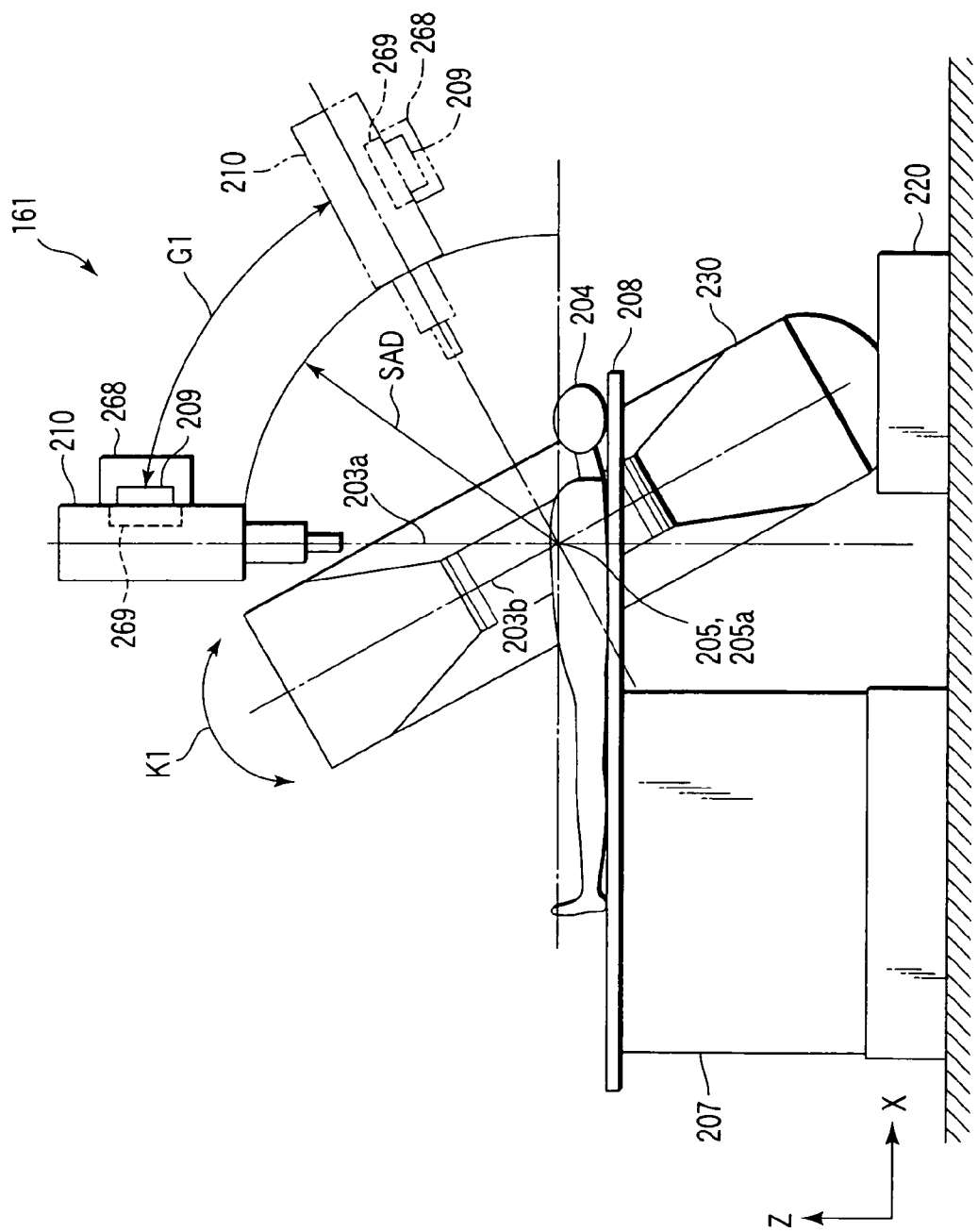
FIG. 18 shows the structure of a radiation treatment apparatus according to a 14th embodiment of the invention, which is viewed in a direction perpendicular to the axis of the bed.
Figure 19:
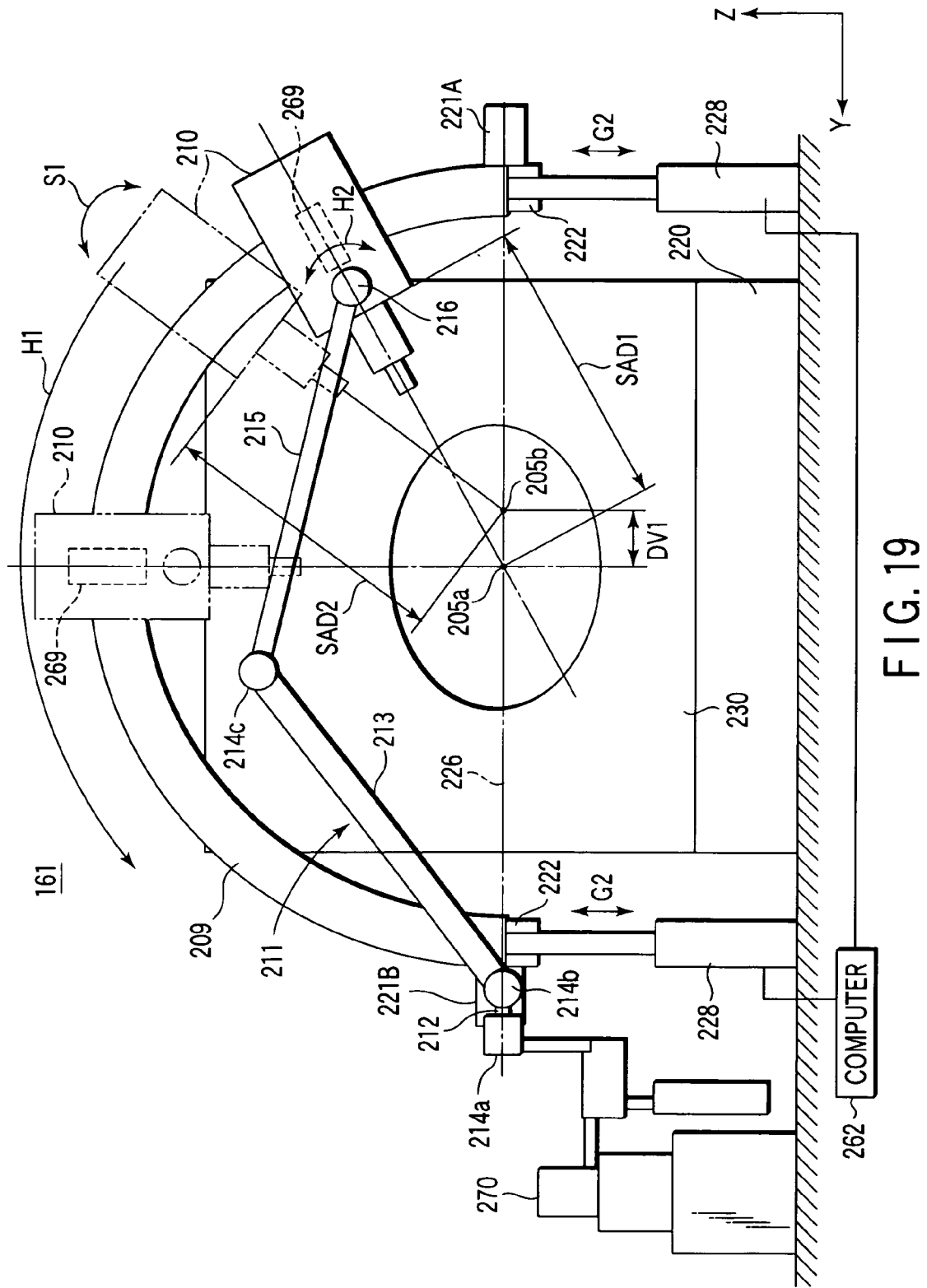
FIG. 19 shows the structure of the radiation treatment apparatus according to the 14th embodiment, as viewed in a bed-axis direction.
Figure 20:
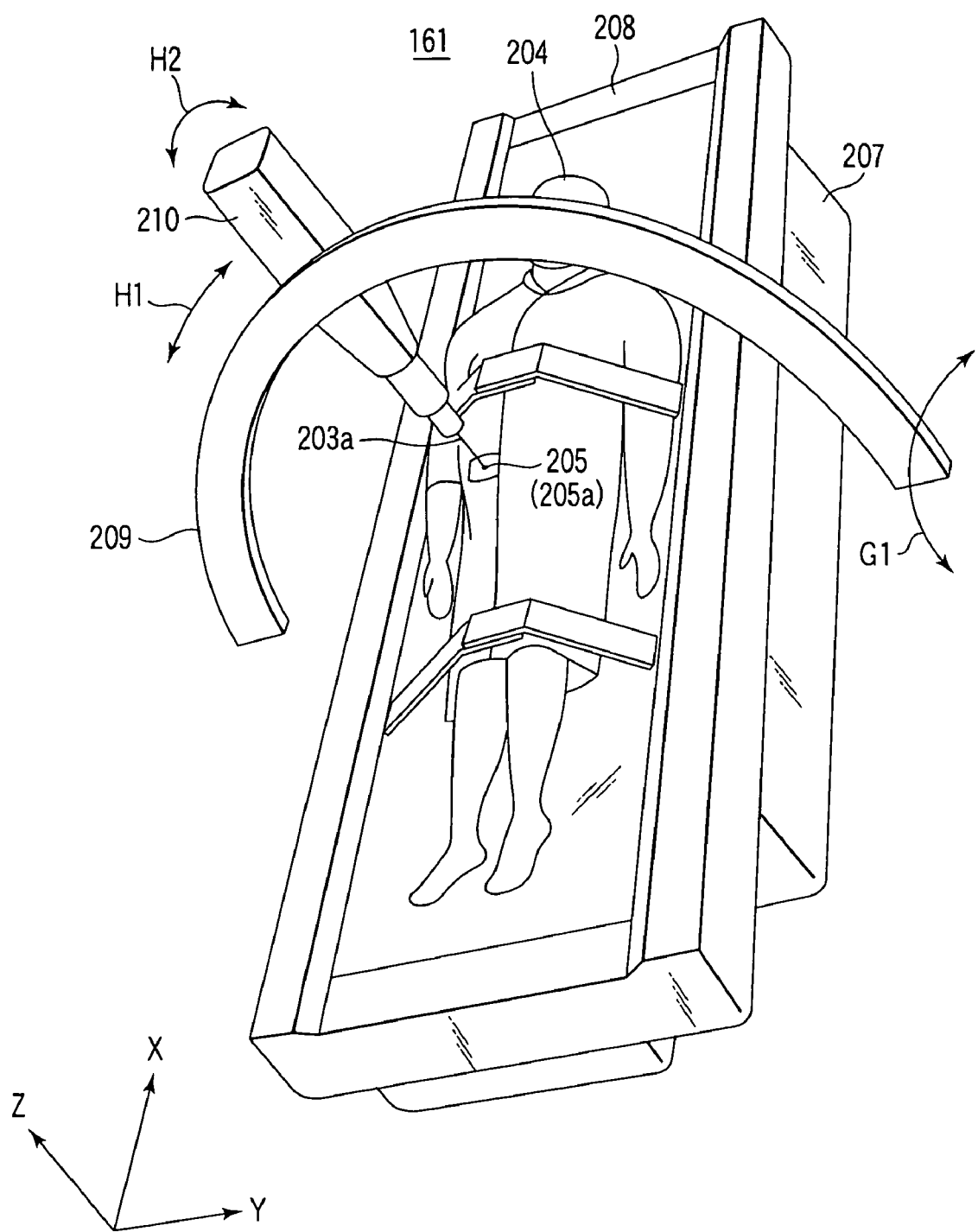
FIG. 20 is a perspective view for explaining radiation treatment using the radiation treatment apparatus according to the 14th embodiment.

As is shown in FIGS. 18 to 20, the radiation treatment apparatus 161 according to this embodiment comprises a bed 207 having a top plate 208 as a slide board on which a patient 204 is placed; a radiation head 210 for applying treatment radiation to a irradiation field 205 that can be set on the patient 204; and an X-ray CT unit 230 that acquires a tomogram of the irradiation field 205 that is a focus.

In FIG. 18, the top plate 208 can be moved by an X-Y drive mechanism (not shown) built in the bed 207 in two axes, that is, an X-axis in the longitudinal direction of the bed, and a Y-axis in the transverse direction of the bed. The top plate 208 is position-controlled by a computer system (not shown) on the basis of an image acquired by a TV camera (not shown) so that the irradiation field 205 of patient 204 may be positioned at an isocenter 205a. In addition, the top plate 208 is formed of such a material and a shape as to be suitable for the X-ray CT unit 230 or a PET (Position Emission Tomography) unit, which is an imager. Numeral 203b denotes an image acquiring X-ray (image acquiring radiation) emitted from the X-ray CT unit 230. Numeral 220 denotes a turning mechanism for tilting the X-ray CT unit 230 in a K1 direction shown in the Figure.

Hereinafter, the longitudinal direction of the bed is referred to as an X-axis direction, the transverse direction of the bed as a Y-axis direction, and the vertical direction of the bed as a Z-axis direction. The patient 204 is placed on the top plate 208 such that the body axis of the patient is situated in the longitudinal direction of the bed of the top plate 208. The X-axis direction and Y-axis direction are horizontal, and the Z-axis direction is vertical.

The radiation head 210 is movably supported on an arc guide rail 209 via a circumferential movement mechanism 268 and a swinging mechanism 269. The radiation head 210 applies treatment radiation 203a. The circumferential movement mechanism 268 and swinging mechanism 269 position the radiation head 210 at a desired radiation position in a range of a ½ sphere centering on the isocenter 205a.

Figure 21:
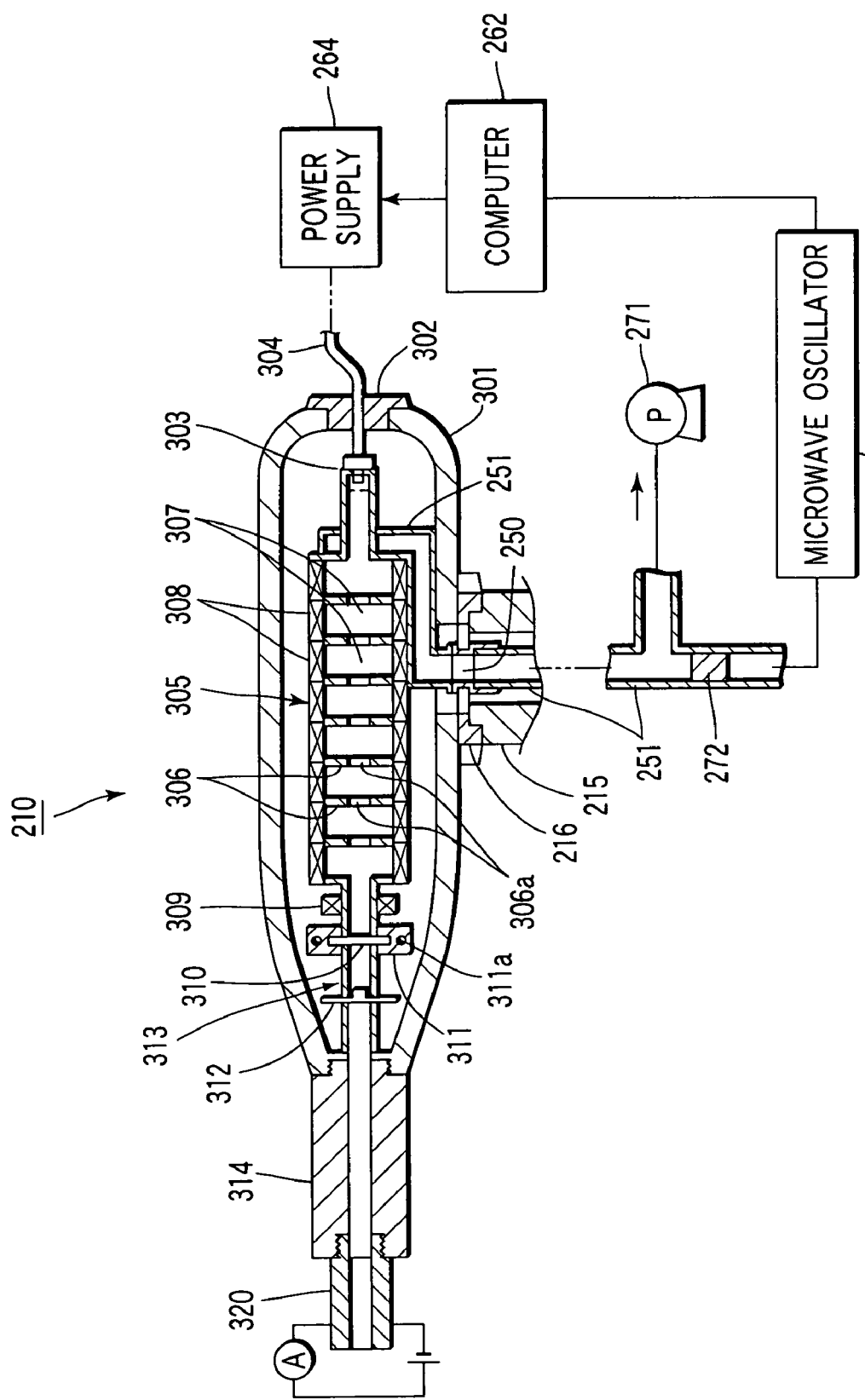
FIG. 21 is a partial cross-sectional view of a radiation head in the radiation treatment apparatus according to the 14th embodiment.

As is shown in FIG. 19, the circumferential movement mechanism 268 circumferentially moves the radiation head 210 along the arc guide rail 209 (direction H1). The circumferential movement mechanism 268 may comprise a rack-and-pinion system or a belt drive system. A fourth joint 216 of a waveguide system 211, 215 is coupled to the radiation head 210. As is shown in FIG. 21 that will be described later in detail, the radiation head 210 is electromagnetically connected to a microwave oscillator 270, such as a Klystron, via waveguide paths 250, 251 and 252 that constitute the waveguide system 211. The swinging mechanism 269, as shown in FIG. 19, swings the radiation head 210 about the fourth joint 216 on the arc guide rail 209 (direction H2). The entire length of the radiation head 210 is 800 to 1000 mm, and the outside diameter of the main body thereof is 300 to 500 mm.

The arc guide rail 209, as shown in FIGS. 19 and 20, comprises a semi-circular ring of an arc defined above the top plate 208. The arc guide rail 209 is disposed to straddle the top plate 208 in its width direction. The arc guide rail 209 is movably supported by a turning mechanism, which comprises motors 221A and 221B and ball-screws 222, and a pair of cylinder mechanisms 228. The turning mechanism turns the arc guide rail 209, as shown in FIG. 18, in a range of 0° to 180° about a turning axis 226 shown in FIG. 19 (direction G1). The arc guide rail 209 is formed of a high-rigidity material such as stainless steel. The arc guide rail 209 has a width of 200 to 400 mm, a thickness of 20 to 50 mm, and a radius of 800 to 1000 mm about the isocenter 205a.

The paired cylinder mechanisms 228 support right and left lower end portions of the arc guide rail 209, as shown in FIG. 19. The cylinder mechanisms 228 elevate the arc guide rail 209 in the Z-axis direction (G2). A computer 262, which is a position control means, controls the cylinder mechanisms 228 so that their operations are synchronized.

As has been described above, in this embodiment, the radiation head 210 can be moved in an isocentric manner on the ½ sphere defined about the isocenter 205a by the tilting (G1) of the arc guide rail 209 and the circumferential movement (H1) of the radiation head 210. In addition, the radiation head 210 can be moved in a non-isocentric manner at positions departing from the ½ sphere defined about the isocenter 205a by the elevation (G2) of the arc guide rail 209 and the swinging (H2) of the radiation head 210.

The X-ray CT unit 230 has a doughnut-shaped vacuum chamber. The vacuum chamber accommodates a number of X-ray generating units that are concentrically arranged. The vacuum chamber has a central opening, and the central opening is used as a diagnosis space. The patient 204 together with the top plate 208 is inserted in, and taken out of, the diagnosis space.

The X-ray CT unit 230 of this embodiment is a non-magnetic type imager. The X-ray CT unit 230 of this embodiment is what is called the fifth-generation device wherein X-ray sources and detectors are stationary, as will be described later in detail. The X-ray CT unit 230 of this embodiment may be replaced with a third-generation X-ray CT device wherein X-ray sources and detectors are rotatable, or a fourth-generation X-ray CT device wherein X-ray sources are rotatable and detectors are stationary.

The X-ray CT unit 230 of this embodiment can be supported by an imager tilting mechanism 220 shown in FIG. 18, at an angle of, e.g. 20° to 30° relative to the X-axis. If the tilting mechanism 220 is driven, the X-ray CT unit 230 is tilted (K1) and the irradiation angle of the image acquiring X-ray 203b is varied. The X-ray CT apparatus 230 and arc guide rail 209 are mechanically firmly coupled so as to have common reference coordinates. The X-ray CT unit 230 is controlled such that the arc guide rail 209 and radiation head 210 do not interfere. If an X-ray transmission unit is used as the imager instead of the X-ray CT unit 230, the resolution and contrast will deteriorate, compared to the X-ray CT unit 230. To solve this problem, a small metal plate, for instance, is buried near the irradiation field so that the plate may be imaged on a transmission image. Thereby, the image of the plate is used as a marker, and the irradiation field is marked with reference to the marker. Thus, the precision in positioning is attained.

Aside from the X-ray CT unit or X-ray transmission unit, a PET can be used as the imager. Furthermore, an MRI unit may be used as a magnetic type imager.

In FIG. 18, SAD (Source Axis Distance) indicates a distance between the isocenter 205a and a target 310 (see FIG. 21) within the radiation head 210. In this embodiment, the SAD is set at 80 cm.

In this embodiment, as shown in FIG. 19, a shift amount DV from the isocenter 205a to a non-isocenter 205b and equations below are obtained by position calculations using the computer 262. Based on the calculation result, the driving of the arc guide rail 209 (G1, G2) and the driving (H1, H2) of the radiation head 210 (H1, H2) are controlled when X-rays are applied to the non-isocenter 205b.

$$H1 = \theta 1 \quad (1)$$

$$H2 = \theta 1 - \arctan((r \sin \theta 1 - DV1)/((r \cos \theta 1))) \quad (2)$$

$$G1 = 0 \quad (3)$$

$$G2 = z \quad (4)$$

Where

θ1: the rotational angle of the arc guide rail 209 from the isocenter vertical axis, r: the radius of curvature of arc guide rail 9 (distance from the isocenter 205a to the center of swinging motion of the radiation head 210), and z: a vertical displacement from the isocenter 205a.

In FIG. 19, each of joint portions 214a to 214c and 216 of the waveguide system 211 includes a rotary RF coupler 250 that propagates acceleration microwaves by axial rotation.

In addition, as shown in FIG. 22, waveguides 251 and 252 are provided in the waveguide system 211. The waveguides 251 and 252 are connected electromagnetically with each other via the rotary RF coupler 250 in the joint portion, 214a to 214c.

Furthermore, as shown in FIG. 23, the rotary RF coupler 250 is connected to the waveguides 251 and 252 by means of flange couplers 253 and 254. Numerals 255a and 255b denote waveguide passages of the waveguides 251 and 252.

As is shown in FIG. 24, the waveguide passages 255a and 255b of waveguides 251 and 252 are connected with a rotary space surrounded by rotary members 256 and 257 of the rotary RF coupler 250. An electric field (vector or mode) is produced in the rotary space, and microwaves are propagated. In FIG. 24, numeral 258 denotes a bearing, and numeral 259 denotes a λ/4 wavelength choke. With the combination of the rotary RF coupler 250 and waveguides 251 and 252, acceleration microwaves can smoothly be supplied to the moving radiation head 210 from the microwave oscillator, such as a Klystron, fixed on the floor.

As is shown in FIG. 19, the waveguide system 211 is a link mechanism having one end fixed to an end portion of the arc guide rail 209 via the first joint portion 214a, and having the other end coupled to the radiation head 210 via the fourth joint portion 216.

The waveguide system 211 comprises the first joint portion 214a fixed to the end portion of the arc guide rail 209; a first waveguide 212 having one end rotatably coupled to the first joint portion 214a; a second joint portion 214b coupled to the other end of the first waveguide 212; a second waveguide 213 having one end coupled to the second joint portion 214b; a third joint portion 214c coupled to the other end of the second waveguide 213; a third waveguide 215 having one end coupled to the third joint portion 214c; and the fourth joint portion 216 coupled to the other end of the third waveguide 215 and also coupled to the radiation head 210.

The first joint portion 214a alone is disposed along the Y-axis, and the second to fourth joint portions 214b, 214c and 216 are disposed along the X-axis.

Next, the X-ray CT unit 230 will be described in detail.

The X-ray CT unit 230 applies a fan-shaped imaging-acquiring X-ray 203b in multiple directions to the irradiation field 205 of the subject such as the patient 204, and detects the transmitted X-ray. The detected data is converted to image by processing, thereby enabling the computer screen to display a tomogram of the irradiation field 205.

The X-ray CT unit 230 of this embodiment is what is called fifth-generation device, and it has a doughnut-shaped vacuum chamber (not shown) with a central opening that is a diagnosis space. The vacuum chamber is evacuated by a vacuum pump via an exhaust port. Within the vacuum chamber, there are provided a number of X-ray generating units (not shown) disposed on an outer-periphery-side concentric circle, and a number of sensor arrays (not shown) disposed on an inner-periphery-side concentric circle in association with the X-ray generating units. The X-ray generating units and sensor arrays are arranged such that they are shifted in the X-axis direction, and the image-acquiring X-ray 203b is applied in a fan-shape inclined in a direction along the axis which perpendicularly pass through the central opening of the doughnut-shaped forward with respect to the radius of the vacuum chamber at isocenter 205a. Thus, the fan-shaped image-acquiring X-ray 203b passes through the patient 204 in the diagnosis space, without being shut off by the sensor arrays situated on the X-ray radiating side. The X-ray that has passed through the patient 204 can be detected by the sensor arrays situated on the opposite side.

The vacuum chamber includes a beam limiter, an electron gun drive circuit and an image signal digitizer. The fan-shaped X-ray 203b emitted from the X-ray generating unit is collimated by a collimator and then restricted to a width at the position of radiation by the beam limiter.

The sensor arrays are densely arranged and fixed along a circumference surrounding the diagnosis space, and comprise many hypersensitive CdTe sensors. The sensor array has a resolution of 0.5 mm. An imaging width of one shot at the time of image acquisition is about 80 mm. The time of X-ray irradiation is 0.01 second per shot.

A data collecting device (not shown) is connected to an X-ray generation control unit (not shown). The data collecting device receives an X-ray generation instruction signal from the computer 262. The X-ray transmission data detected by the sensor array is converted to a current signal that is proportional to the transmission X-ray dose. The current signal is delivered to a digitizer (not shown) via a preamplifier and a main amplifier (both not shown) and then accumulated in the data collecting device (not shown). The timing of data accumulation is controlled by the X-ray generation instruction signal from the computer 262. The accumulated data is output to a signal processing unit (not shown) from the data collecting device, and is processed by the signal processing unit. The processed data is reproduced and displayed on a display (not shown) as a tomogram of the irradiation field 205.

On the other hand, the output side of the X-ray generation control unit (not shown) is connected to a generator, and an anode, a cathode and a grid electrode of a gate array (not shown) of the X-ray generating unit. If the computer 262 outputs the X-ray generation instruction signal to the X-ray generation control unit, the X-ray generation control unit controls the power supply operation for supplying power from a power supply (not shown) to an electron gun drive circuit (not shown) and selects the grid electrode among the gate arrays, which is suitable for the part to be imaged. Accordingly, one of the cathodes of the X-ray generating unit emits an electron beam, and a negative bias voltage applied to the selected grid electrode is released and set at a zero potential. The electron beam passes through the hole of the grid electrode and is emitted to the anode. Once the electron beam has been incident on the anode, the anode emits a secondary X-ray and thus the fan-shaped image-acquiring X-ray 203b is emitted toward the patient 204 via a collimator attached to the window.

If the computer 262 has received transmission X-ray data of the irradiation field 205 from the X-ray CT unit 230, the computer 262 controls the operations of the circumferential movement mechanism 268, swinging mechanism 269 and imager turning mechanism 220. Thereby, the position and direction of the radiation head 210 are finely adjusted, and the radiation head 210 is aimed at the irradiation field 205 that is situated at the isocenter 205a or non-isocenter 205b.

The radiation head 210 will now be described in detail with reference to FIG. 21.

The radiation head 210 of this embodiment accelerates electrons up to an energy level of 4 MeV to 20 MeV and generates the treatment radiation 203a. The radiation head 210 functions as the radiation head of the radiation treatment apparatus 161. The radiation head 210 has an outer casing 301 having radiation shield properties. The outer casing 301 accommodates an electron gun 303, an acceleration tube 305, a focusing coil 309, an X-ray target 310, a flattening filter 312 and a focusing tube 313.

An insulating cap 302 is fitted on a tail end of the outer casing 301. A cable 304 connected via the insulating cap 302 to a power supply 264 is brought into the casing 301. The cable 304 is connected to the electron gun 303. The output of the power supply 264 of the electron gun 303 is controlled by the computer 262.

The elements between the electron gun 303 and the flattening filter 312 are arranged in series along the center axis of the electron beam. The electron gun 303 is continuous with the acceleration tube 305, and the acceleration tube 305 is continuous with the focusing tube 313.

The waveguide 251 connects with the acceleration tube 305. The waveguide 251 connects with the microwave oscillator 270 and a vacuum pump 271. The inside of the acceleration tube 305 is evacuated by the pump 271 via the waveguide 251. A ceramic window 272 is fitted in a main passage of the waveguide 251 that is branched to the vacuum pump 271. The ceramic window 272 shuts off SF6 gas sealed in the waveguide between microwave oscillator 270 and the ceramic window 272, and the ceramic window 272 permits passage of only microwaves.

The microwave oscillator 270 is of a Klystron type with high output stability. The power supply circuit of the microwave oscillator 270 is connected to the computer 262. The electron gun 303 has a filament (cathode) provided within a chamber that is evacuated by the vacuum pump 271.

The acceleration tube 305 is provided to continuously connect with the chamber containing the electron gun 303. The acceleration tube 305 accelerates the electron emitted from the electron gun 303. The inside of the acceleration tube 305 is divided by a plurality of partitions 306, thus forming a plurality of acceleration cavities 307. An electron beam passage hole 306a is formed at a center of each partition 306. Coils 308 are wound around the respective acceleration cavities 307, and the coils 308 are connected to the power supply circuit that is operated and controlled by the computer 262.

The focusing tube 313 is provided to be continuous with the acceleration tube 305. In the focusing tube 313, a focusing coil 309, an X-ray target 310 and a flattening filter 312 are attached in this order. The focusing coil 309 converges the electrons accelerated by the acceleration tube 305 toward the X-ray target 310.

The X-ray target 310 receives high-energy accelerated electrons and emits bremsstrahlung X-rays. Thus, in order to prevent thermal damage, a water-cooling jacket 311 having a flow path 311a is attached to the X-ray target 310 so that the X-ray target 310 is forcibly cooled. Preferably, the target 310 is formed of an elemental metal such as tungsten, molybdenum or tantalum, or an alloy thereof.

The flattening filter 312 is formed of a metal and averages the intensity of the X-ray emitted from the target 310. The flattening filter 312 thus produces the treatment radiation 203a having a substantially uniform energy density.

A collimator 314 and a dose measuring tube 320 are attached to the outside of the outer casing 301. The collimator 314 is screwed in a distal end portion of the outer casing 301. The collimator 314 has a hollow portion connecting with the focusing tube 313. The collimator 314 is formed of a high-shield-property material, such as lead, that shuts off the treatment radiation 203a. The X-ray 203a is transmitted to the dosimeter tube 320 via the hollow portion.

The dosimeter tube 320 comprises an ionization chamber in which a gas is sealed. The dosimeter tube 320 detects the amount of charge of an ionized gas that is produced when the radiation passes, thus measuring the dose.

Figure 25:
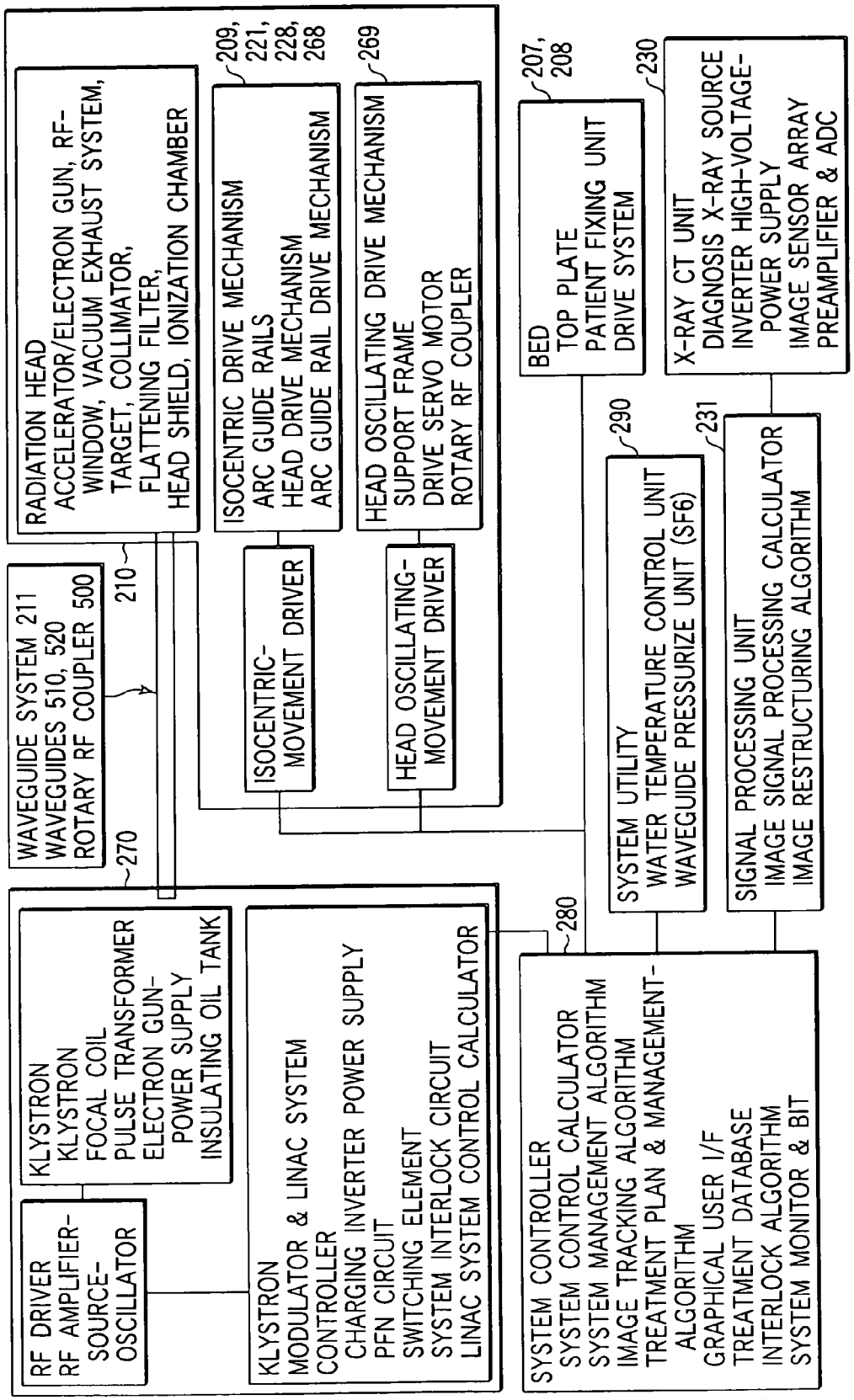
FIG. 25 is a block diagram of the radiation treatment apparatus according to the 14th embodiment.

A control system of the apparatus of this embodiment will now be described with reference to FIG. 25.

The radiation treatment apparatus of this embodiment has a control system comprising a treatment bed system 207, 208, radiation head 210, X-ray CT unit 230, a signal processing unit 231, microwave oscillator 270, a system control unit 280 and a system utility 290. The system control unit 280 controls the entirety of the system.

The system control unit 280 includes a system control calculator, a system management algorithm, an image tracking algorithm, a treatment plan algorithm, a treatment management algorithm, a graphical user interface, a treatment database, an interlock algorithm, a system monitor, and BIT. The system control unit 280 controls the entirety of the control system, performs exchange of input/output signals with the other blocks.

The X-ray CT unit 230 is connected to the system control unit 280 via the signal processing unit 231. Thereby, during the radiation treatment, images are acquired in real time by the X-ray CT unit 230. The doctor can perform treatment while viewing the images displayed on the display.

The microwave oscillator 270 comprises a klystron modulator & linac system control unit, a Klystron, and an RF driver. The Klystron that is a supply source of microwaves to the acceleration tube 305 is connected to the radiation head 210 via the waveguide system 211.

Drivers for the isocentric drive mechanism and swinging drive mechanism of the radiation head 210 are connected to the system control unit 280. The radiation head 210 is controlled the circumferential movement at the time of isocentric irradiation and the two-axes swinging movement at the time of pseudo-non-isocentric irradiation.

In the above-described embodiment, radiation is applied from the ½ spherical positions. The radiation head 210 may be equipped with an imager having a smaller size than the X-ray CT unit 230 in the form of a unit. Thereby, radiation can be applied from any point of the upper-half sphere.

A treatment method using the apparatus of this invention will now be described with reference to FIG. 26.

In radiation treatment, the doctor prepares a treatment plan. The treatment plan is based on various inspections conducted prior to an operation. In addition, during the operation, the doctor acquires an image of a patient's focus as direct in real-time, using the radiation treatment apparatus of the present embodiment. With the acquisition of the image, more precise and sure radiation treatment can be performed.

Figure 26:
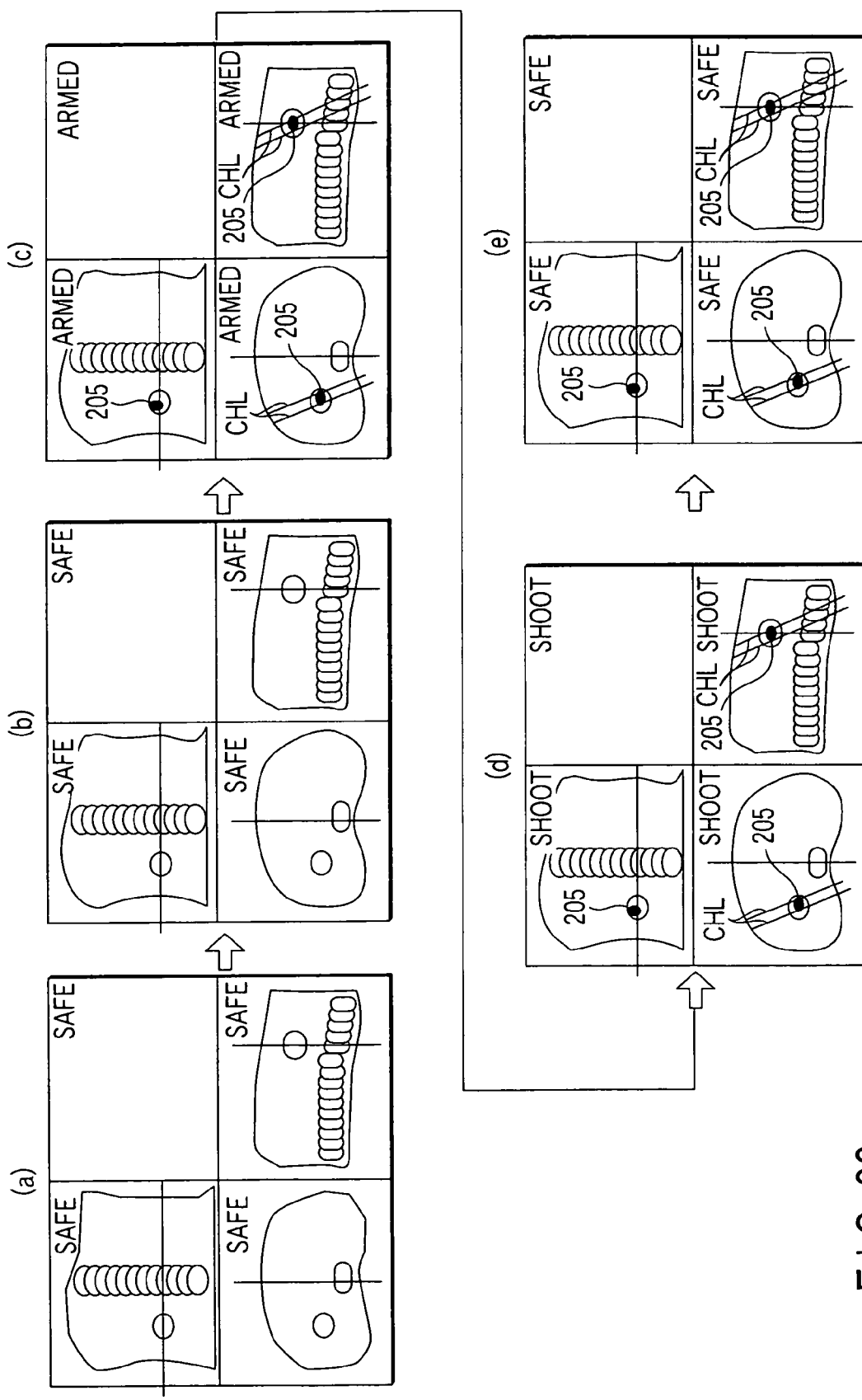
FIG. 26 illustrates operational procedures of the radiation treatment in the 14th embodiment, referring to a transitional change of monitor screens.

As is shown at (a) in FIG. 26, images of the irradiation field 205 and vicinity thereof are obtained by using the X-ray CT unit 230 alone. Each cross section of the irradiation field 205 is confirmed on the system screen, and a contour line for image tracking is defined. Prior to the treatment, the mapping of the irradiation field 205 is finished. Referring to the mapping, the contour of the irradiation field 205 is defined at a plurality of slices.

As is shown at (b) in FIG. 26, a contour of the image of the actual irradiation field 205 is selected by the image tracking system of the radiation treatment apparatus. The selected contour and the defined contour line are subjected to pattern matching, and the image tracking is started. The doctor confirms the state of image tracking visually.

As is shown at (c) in FIG. 26, after the image tracking is stabilized, the doctor operates a master arm switch (Master Arm SW) and sets the system in the ARMED state. The system displays a target on the image by cross hairlines and also displays a radiation volume in red on the same image. Since image tracking is continued, the target and radiation volume will automatically follow the movement of the irradiation field.

As is shown at (d) in FIG. 26, application of the treatment radiation 203a is started by the doctor's trigger operation. At the stage of the treatment plan, a radiation time is predetermined. Count-down begins on the screen. When the count value has decreased to zero, the treatment radiation is automatically stopped. A dose of distribution is successively displayed on the screen, and the doctor continues the irradiation with the trigger being pulled, while confirming the displayed dose. The system alternately continues at high speed the image sampling and the application of the treatment radiation 203a, and continues in real time the image tracking and the application of the treatment beam. Even before the count value has decreased to zero, if the doctor releases the trigger, the treatment radiation 203a is immediately stopped at that time. Thus, the safety is fully maintained.

As is shown at (e) in FIG. 26, the doctor operates the master arm switch (Master Arm SW) at the SAFE position and sets the system in the safe state. Then, the doctor moves the radiation head 210 to the next radiation position. After the end of the radiation at each portal and a series of radiation operations, the doctor confirms a total dose that corresponds to the total of accumulated radiation amount. The total dose and the total dose distribution in each course are displayed on the screen and stored in a treatment file prepared for each patient.

As has been described above, according to the embodiment, the conditions such as the position of application of radiation and the time of radiation can be precisely controlled while the irradiation field is being confirmed using the X-ray CT unit 230. Thus, this embodiment is applicable to the treatment of the head in which the organ itself does not move, and also the radiation can exactly be applied to a small focus of a movable organ such as the heart or lung. A greater number of applications in the radiation field treatment can be expected.

Moreover, according to the present embodiment, unlike a cantilever-type robot arm that has a problem in terms of rigidity, the radiation head support structure with high strength and rigidity can be adopted. Thus, high mechanical precision can be ensured. Accordingly, there is no need to perform teaching that is necessary in order to ensure desired positioning precision with use of a robot arm, and efficient treatment can be performed.

It is problematic in terms of the safety of the patient to apply a general-purpose industrial robot, which has a much higher degree of freedom than required, to the non-isocentric radiation treatment. Specifically, when the robot arm has accidentally malfunctioned, the robot arm or the radiation head attached to the distal end of the robot arm may hit the patient and cause an external injury to the patient. By contrast, in the radiation treatment apparatus of this embodiment, the ranges of mechanical movement of the radiation head support mechanism and radiation head are limited. Therefore, the absolute safety of the patient can be ensured.

In the prior art, the irradiation field cannot be monitored in real time during the radiation treatment, and the irradiation has to be performed based on estimation. By contrast, according to the radiation treatment apparatus of this embodiment, the irradiation field can be monitored in real time during radiation treatment by the imager such as the X-ray transmission unit, X-ray CT unit, PET (Positron Emission Tomography) or DSA (Digital Subtraction Angiogram), etc. Therefore, radiation treatment with high reliability and safety can be performed. Furthermore, the image tracking can be performed based on the real-time irradiation field image, and the tracking irradiation on the moving irradiation field can be realized.

Besides, according to the radiation treatment apparatus of this embodiment, the man-machine interface with the doctor is provided, and the exact radiation treatment with high safety and reliability can be performed.

Figure 28:
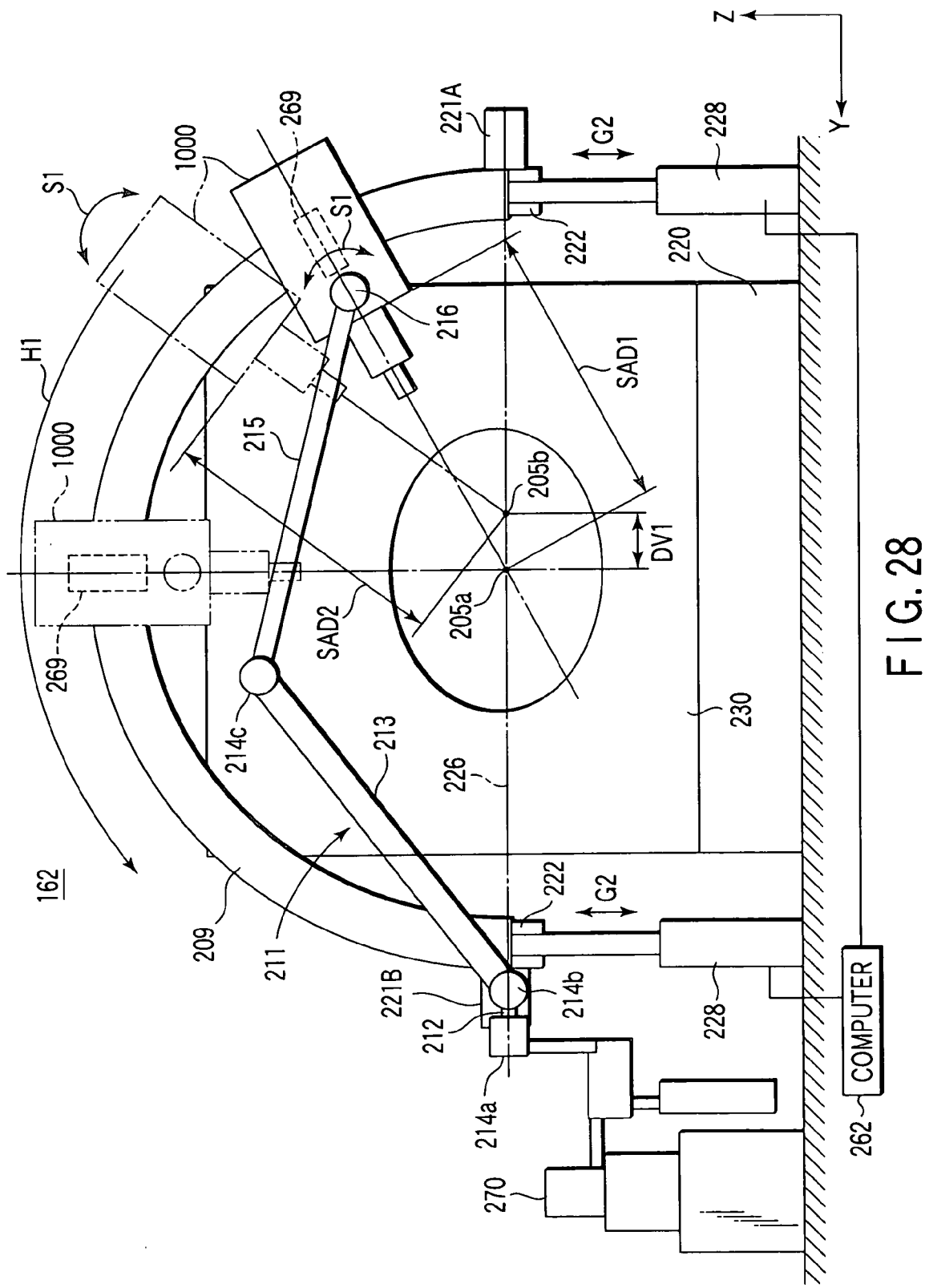
FIG. 28 shows the structure of the radiation treatment apparatus according to the 15th embodiment, as viewed in a bed-axis direction.
Figure 29:
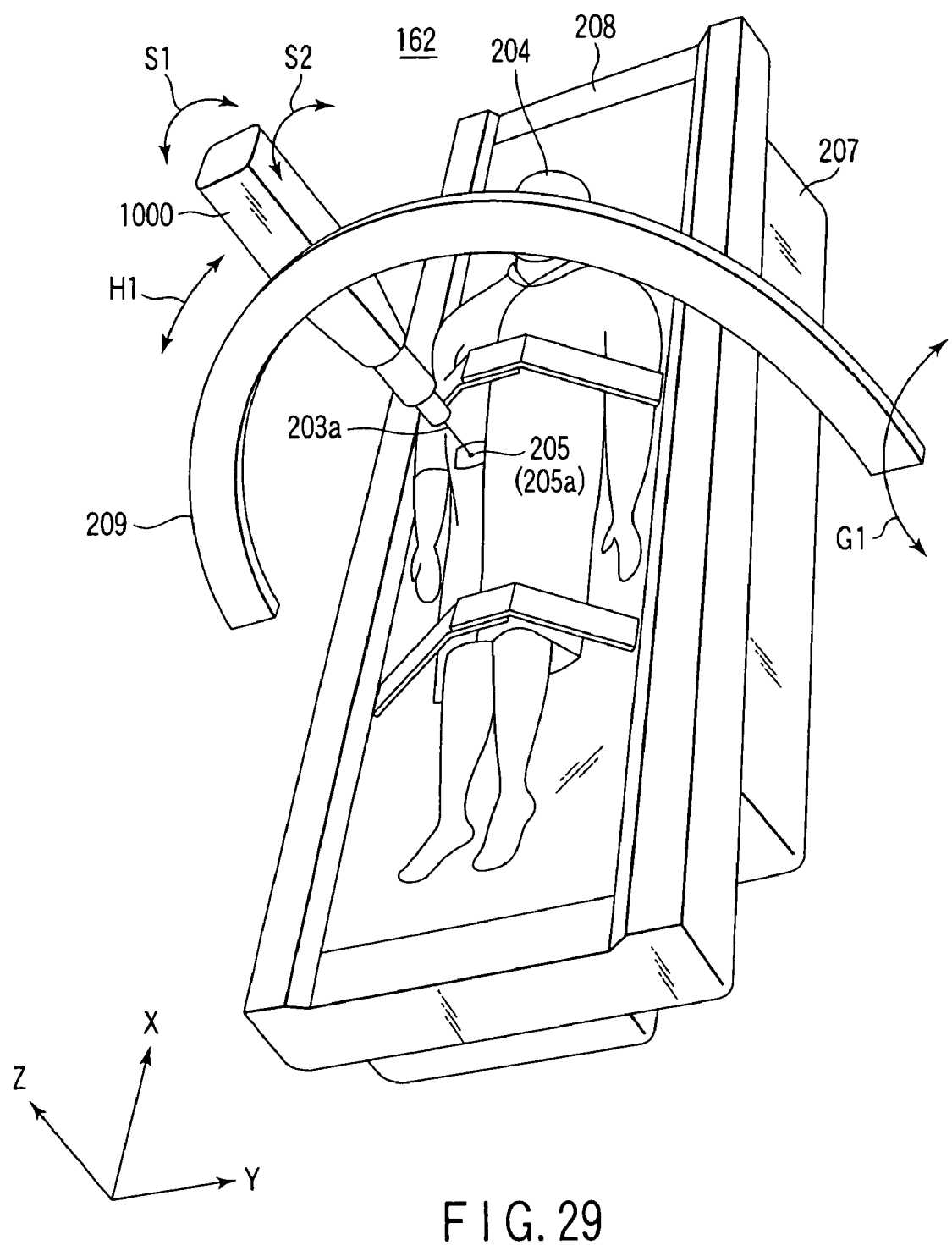
FIG. 29 is a perspective view for explaining radiation treatment using the radiation treatment apparatus according to the 15th embodiment.
Figure 30:
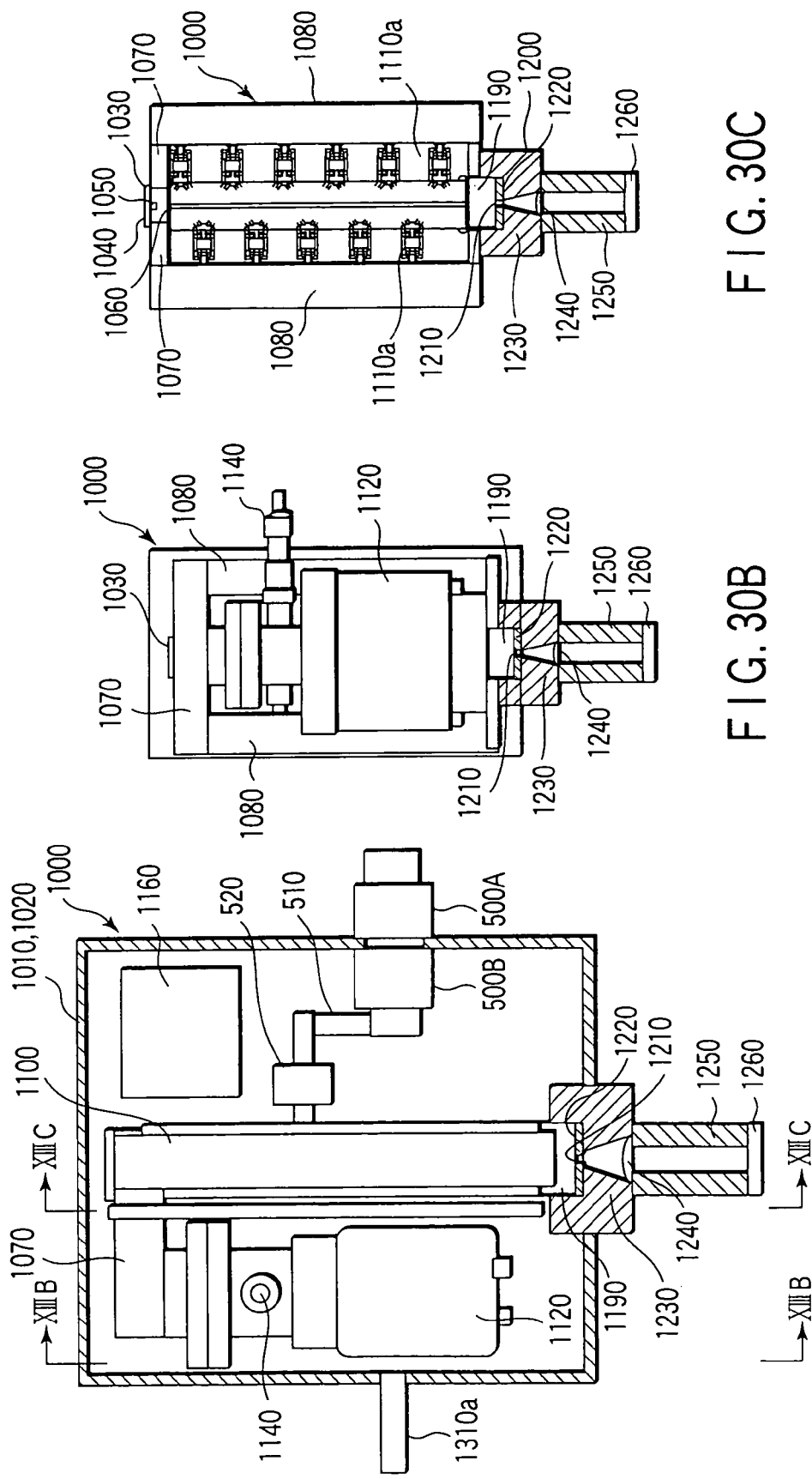
FIGS. 30A, 30B and 30C show a radiation head in the radiation treatment apparatus according to the 15th embodiment, FIG. 30B being a cross-sectional view taken along line XIIIB—XIIIB in FIG. 30A, and FIG. 30C being a cross-sectional view taken along line XIIIC—XIIIC in FIG. 30A.
Figure 34:
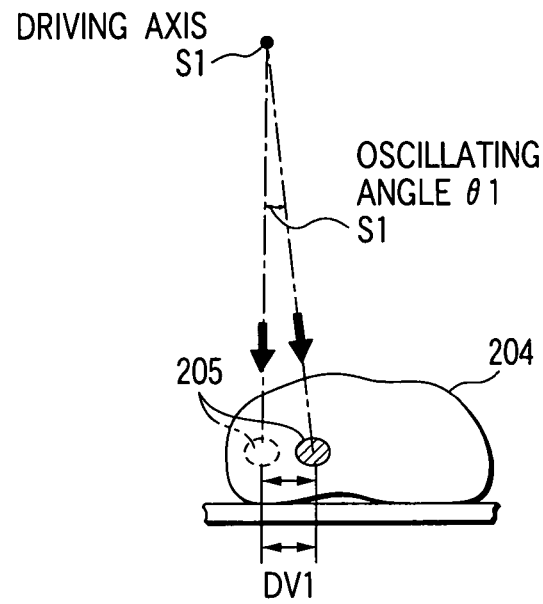
FIG. 34 is a partial cross-sectional view taken along line XVII—XVII in FIG. 32, illustrating another example of the swinging operation of the radiation head in the case of performing radiation treatment in a pseudo-non-isocentric manner using the radiation treatment apparatus of the 15th embodiment.
Figure 35:
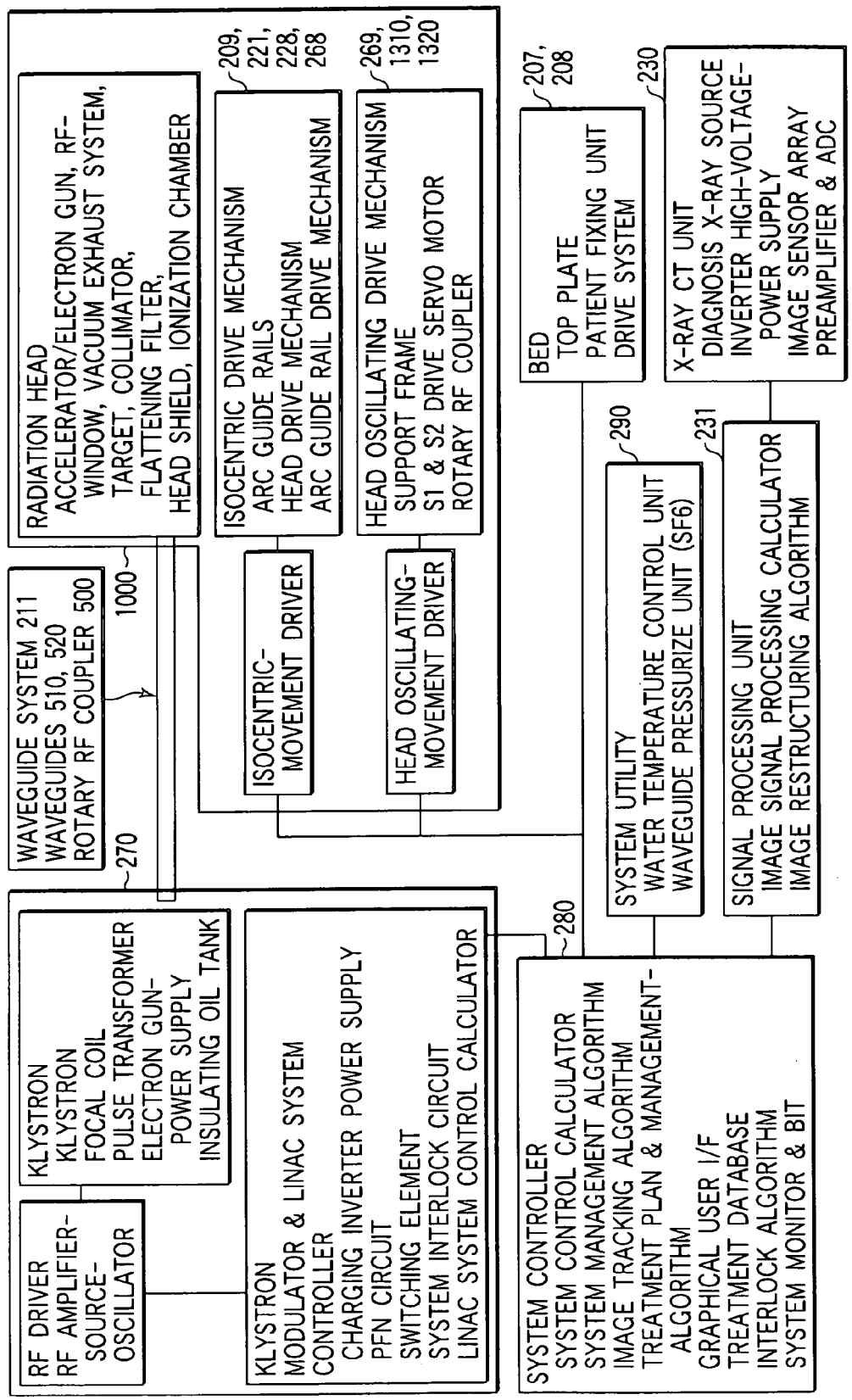
FIG. 35 is a block diagram of the radiation treatment apparatus according to the 15th embodiment of the invention.
Figure 38:
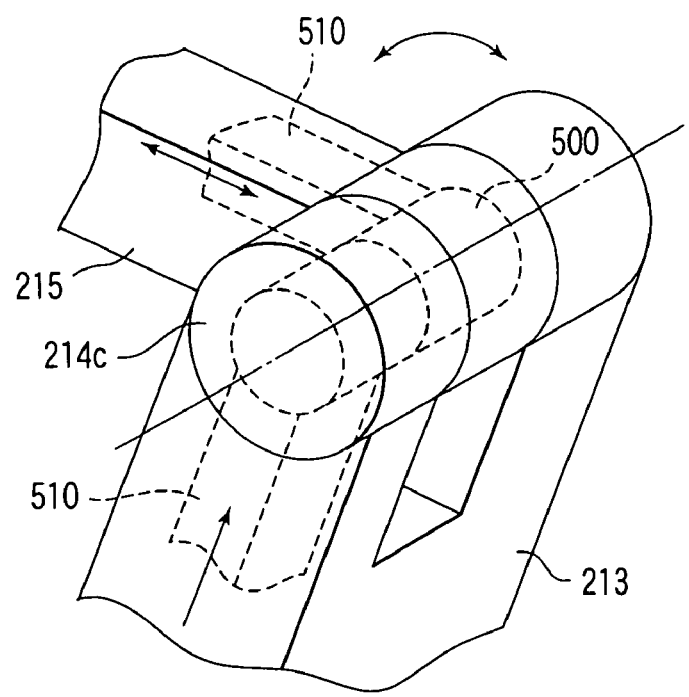
FIG. 38 is a perspective view showing a waveguide system and a rotary RF coupler in the radiation treatment apparatus of the 15th embodiment.
Figure 39:
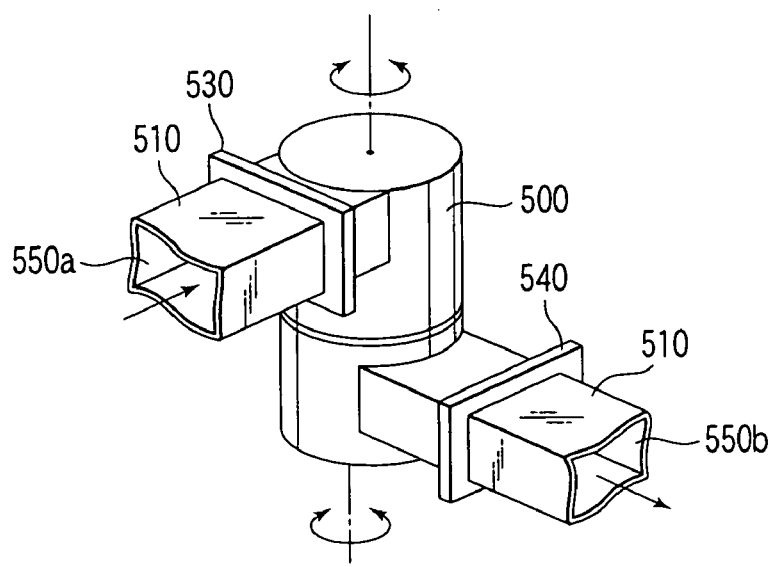
FIG. 39 is a perspective view showing the rotary RF coupler and waveguides in the radiation treatment apparatus of the 15th embodiment.

A radiation treatment apparatus 162 according to a 15th embodiment of the invention will now be described with reference to FIG. 27 through FIG. 42 wherein the same parts as those in FIGS. 18 to 26 are denoted by same reference numerals. FIGS. 27 to 29 correspond to FIGS. 18 to 20; FIG. 35 corresponds to FIG. 25; FIGS. 38 and 39 correspond to FIGS. 22 and 23; and FIG. 42 corresponds to FIG. 26. A description of the overlapping parts in these Figures is omitted.

As is shown in FIGS. 27 to 29 and FIGS. 37A to 37D, a radiation head 1000 of this embodiment is supported on the guide rail 209 by a circumferential movement mechanism 268 and first and second swinging mechanisms 1310 and 1320. The circumferential movement mechanism 268 and first and second swinging mechanisms 1310 and 1320 position the radiation head 1000 at a desired radiation position in a range of a ½ sphere centering on the isocenter 205a.

The circumferential movement mechanism 268 circumferentially moves (H1) the radiation head 1000 along the arc guide rail 209 by means of a rack-and-pinion system, a belt system, etc.

As is shown in FIGS. 37A to 37D, the first swinging mechanism 1310 has a servo motor and swings the radiation head 1000 over the arc guide rail 209 about a first axis S1 of a rotary RF coupler 216. In this case, the rotary RF coupler 216 is provided on an axis that passes substantially through the center of inertia of the radiation head 1000 so as to decrease the moment when the radiation head 1000 is swung.

As is shown in FIGS. 37A to 37D, the second swinging mechanism 1320 has a servo motor and swings the radiation head 1000 about a second axis S2 of rotary RF couplers 500A and 500B. The rotary RF couplers 500A and 500B are provided on an axis that passes substantially through the center of inertia of the radiation head 1000 so as to decrease the moment when the radiation head 1000 is swung. The radiation head 1000 of this embodiment has a length of 500 to 600 mm, a width of 500 mm, a depth of 300 mm and a weight of 60 to 80 kg.

The radiation head 1000 is swingably jointed to the rotary RF coupler 216 of the waveguide system 211. The radiation head 1000 is connected to the microwave oscillator 270 via a waveguide 510 and a rotary RF coupler 500 on a gimbal mechanism shown in FIG. 37A.

By the above-mentioned two-axis driving (G1, H1), the radiation head 1000 can be moved in an isocentric manner on the ½ sphere defined about the isocenter 205a. In addition, by the above-mentioned two-axis driving (S1, S2), the radiation head 1000 can be moved in a pseudo-non-isocentric manner on the ½ sphere defined.

The pseudo-non-isocentric movement is a swinging movement about the center of inertia of the radiation head 1000. Thus, much quicker movement can be achieved, compared to the isocentric movement. By virtue of the pseudo-non-isocentric high-speed tracking motion with high responsivity, the head can be aimed with high responsivity and precision in a tracking manner in accordance with quick movement of, e.g. heartbeats.

Figure 33:
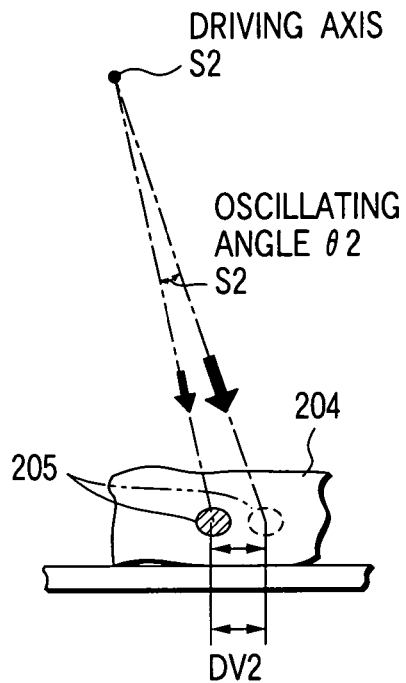
FIG. 33 is a partial cross-sectional view taken along line XVI—XVI in FIG. 32, illustrating an example of a swinging operation of the radiation head in the case of performing radiation treatment in a pseudo-non-isocentric manner using the radiation treatment apparatus of the 15th embodiment.

In the present embodiment, the irradiation in the tracking manner in accordance with the movement of the irradiation field is performed in the following manner. As is shown in FIGS. 32, 33 and 34, using shift amounts DV1 and DV2 obtained from image data and predetermined formulae, a fine displacement angle θ1 about S1-swing drive axis and a fine displacement angle θ2 about S2-swing drive axis are calculated. Based on the calculation results, the operations of the swinging mechanisms 331 and 332 are controlled, and the radiation head 1000 is quickly swung by degrees corresponding to the fine displacement angle θ1 and fine displacement angle θ2. Thereby, the radiation head 1000 can be quickly aimed, with high responsivity, at the diseased part 205 that is placed in parts of the patient, other than the head, e.g. a tumor with movement due to respiratory movement, heartbeats, peristalsis, urine in the bladder, etc. Therefore, high-precision application of radiation is realized. In the radiation treatment apparatus of this embodiment, the radiation head 1000 can be swung at high speed within 0.1 second including a processing time for acquired images. The movement of the radiation head 1000 can be quickly adjusted in a tracking manner in accordance with the movement of the irradiation field (diseased part).

As is shown in FIG. 40A, waveguide passages 550a and 550b of the waveguide 510 connect with a rotary space surrounded by rotary members 560 and 570 of the rotary RF coupler 500. In the rotary space, microwaves are guided in an in-tube mode as exemplified in FIG. 40B.

If system control unit 280 has received tomogram data of the irradiation field 205 from the X-ray CT unit 230 functioning as the imager, it controls the operations of the circumferential movement mechanism 268, the tilting mechanism and the bed 207 on the basis of the received data. Thereby, the radiation head 1000 is aimed at the irradiation field 205 that is situated at the isocenter 205a.

In addition, if the irradiation field 205 has moved, the system control unit 280 performs arithmetic operations for image tracking, based on the input data from the X-ray CT apparatus 230. Based on the arithmetic result, the system control unit 280 controls the operations of the first and second swinging mechanisms 1310 and 1320 and swings the radiation head 1000. While the swinging operation of the radiation head 1000 is being performed, an interlock control is effected to prohibit the application of radiation. Thus, the dose in the vicinity of the focus can be limited to a minimum.

The radiation head 1000 of the present embodiment will now be described in detail.

In the radiation head 1000, as is shown in FIGS. 30A to 30C and FIG. 36, the head body is covered with a cover 1010. An emission portion 1200 for emitting radiation is provided at a distal end portion of the head body. The cover 1010 encasing the head body accommodates an electric circuit/cooling-water circuit 1160, an acceleration tube 1100, an RF window 520, a waveguide 510, a portion 500B of the rotary RF coupler, an exhaust conduit 1070, an ion pump 1120, a target exhaust chamber 1190, a target 1210, and a cooling plate 1220. A cable (not shown), which is connected from an insulator 1030 provided at the tail end of the acceleration tube 1100 to an external power supply, is brought into the cover 1010 and connected to a cathode 1050 of an electron gun 1040. An anode 1060 is disposed to face the cathode 1050. The space between the cathode 1050 and anode 1060 is vacuumed via the exhaust conduit 1070 connecting with the ion pump 1120. The power supply to the electron gun 1040 is controlled by the system control unit 280. The electron gun 1040 is continuous with the emission portion 1200 via the acceleration tube 1100. The length between the insulator 1030 and the distal end of the acceleration tube 1100 is about 360 mm.

As is shown in FIG. 31, the central hole in the anode 1060 of electron gun 1040 connected with a buncher cavity 1090 of the acceleration tube 1100. The acceleration tube 1100 accelerates an electron emitted from the electron gun 1040 and causes the high-energy electron beam to impinge upon the X-ray target 1210. An acceleration cavity 1110b with a central hole for electron beam passage is provided within the acceleration tube 1100. The acceleration cavity 1110b connects with a pair of right and left lateral exhaust conduits 1080 via side-couple cavities 1110a. The paired lateral exhaust conduits 1080 are connected to the ion pump 1120. Thereby, the lateral exhaust conduits 1080 are vacuumed by the ion pump 1120. In other words, the acceleration tube 1100 is vacuumed by the ion pump 1120 via the side-couple cavities 1110a and lateral exhaust conduits 1080.

The waveguide 510 connects with the acceleration tube 1100. The waveguide 510 connects with the microwave oscillator 270 via the ceramic RF window 520 and rotary RF couplers 500A and 500B. The RF window 520 is an inlet that prevents leak of SF6 gas sealed in the waveguide 510 and introduces microwaves into the acceleration tube 1100. The microwave oscillator 270 is a Klystron-type device with high stability of output. The power supply circuit of the microwave oscillator 270 is connected to the system control unit 280.

The emission portion 1200 is provided at the distal end of the head body encased with the cover 1010. The emission portion 1200 includes the X-ray target 1210, target cooling plate 1220, a primary collimator 1230 and a flattening filter 1240. The elements from the electron gun 1040 to the flattening filter 1240, through the acceleration tube 1100 intervening, are linearly arranged along the axis of the electron beam. The accelerated electron beam is made incident on the target 1210 of emission portion 1200 via the target exhaust chamber 1190.

The X-ray target 1210 receives high-energy accelerated electrons and emits bremsstrahlung X-rays. Consequently, the X-ray target 1210 is susceptible to thermal damage. To prevent such thermal damage, the X-ray target 1210 is cooled by the cooling plate 1220. The target 1210 is formed of a high-melting-point metal such as tungsten or tantalum, or an alloy thereof.

The primary collimator 1230 is formed of a material, e.g. tungsten, which has high radiation-shield properties and generates less thermal neutrons. The primary collimator 1230 guides x-rays from the target 1210 to the flattening filter 1240.

The flattening filter 1240 averages the intensity of radiation (X-ray) emitted from the target 1210 and produces the treatment radiation 203a having a uniform dose distribution.

A secondary collimator 1250 and a ionization chamber 1260 for dosimeter are attached to the distal end of the emission portion 1200. The secondary collimator 1250 is formed of a material with high radiation-shield properties, such as tungsten, which permits no passage of the treatment radiation 203a. The treatment radiation 203a is transmitted to the ionization chamber 1260 through the hollow part of the secondary collimator 1250. The secondary collimator 1250 is detachably screwed in the end face of the primary collimator 1230.

The ionization chamber 1260 for dosimeter is attached to the distal end of the secondary collimator 1250, and a gas of a predetermined composition is sealed therein. A detection circuit (not shown) for detecting the discharged electricity is connected to the ionization chamber 1260. The detection circuit is connected to the input side of the system control unit 280. The system control unit 280 calculates the dose of the treatment radiation emitted from the radiation head 1000, on the basis of the input signal from the dose-measuring ionization chamber 1260. The calculated result is stored in a memory as dose data for treatment of the patient 204.

A control system of the radiation treatment apparatus according to the present embodiment will now be described with reference to FIG. 35.

The control system of this apparatus comprises a bed 208, radiation head 1000, X-ray CT unit 230, a signal processing unit 231, microwave oscillator 270, a system control unit 280 and a system utility 290. The system control unit 280 controls the entirety of the system.

The system control unit 280 includes a system control calculator, a system management algorithm, an image tracking algorithm, a treatment plan algorithm, a treatment management algorithm, a graphical user interface, a treatment database, an interlock algorithm, a system monitor, and BIT.

The X-ray CT unit 230 is connected to the system control unit 280 via the signal processing unit 231. Thereby, during the radiation treatment, images are acquired in real time. The doctor can perform treatment while viewing the images displayed on the display.

The microwave oscillator 270 comprises a klystron modulator & linac system control unit, a Klystron, and an RF driver. The Klystron that supplies microwaves to the acceleration tube 1100 is connected to the radiation head 1000 via the waveguide system 211.

Drivers for the isocentric drive mechanism and swinging drive mechanisms of the radiation head 1000 are connected to the system control unit 280. The circumferential movement mechanism 268 is controlled at the time of isocentric irradiation and the 2-axis swinging mechanisms 1310 and 1320 are controlled at the time of pseudo-non-isocentric irradiation.

The swinging mechanisms of this embodiment will now be described in detail with reference to FIGS. 32 to 34, FIG. 36 and FIGS. 37A to 37D.

Figure 36:
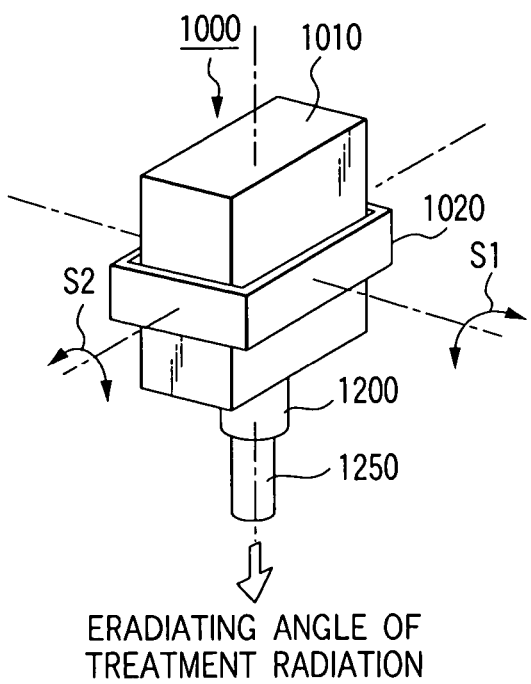
FIG. 36 is a perspective view showing the radiation head of the radiation treatment apparatus according to the 15th embodiment of the invention.

As is shown in FIG. 36, the radiation head 1000 of this embodiment is supported on a gimbal support frame 1020 of the head cover 1010. The support frame 1020 is disposed at positional coordinates through which the axes S1 and S2 including the center of inertia of the radiation head 1000 extend.

As is shown in FIG. 37A, the rotary RF coupler 216 of waveguide system 211, paired rotary RF couplers 500A and 500B, the S1-axis swinging mechanism 1310 comprising a servo motor, and the S2-axis swinging mechanism 1320 comprising a servo motor are attached to the respective sides of the support frame 1020.

As is shown in FIG. 37B, the rotary RF coupler 216 of the waveguide system 211 is attached to the center of one of the long sides of the support frame 1020. A drive shaft 1310a of the S1-axis swinging mechanism 1310 is attached to the center of the other long side of the frame 1020 so as to face the rotary RF coupler 216. When the drive shaft 1310a is rotated, the radiation head 1000 is swung about the S1-drive shaft, as shown in FIG. 34.

As is shown in FIG. 37D, the paired rotary RF couplers 500A and 500B are attached to the center of one of the short sides of the support frame 1020.

As is shown in FIG. 37C, a drive shaft 1320a of the S2-axis swing mechanism 1320 is disposed at the center of the other short side of the support frame 1020 so as to face the paired rotary RF couplers 500A and 500B. Specifically, the body of the S2-axis swinging mechanism 1320 is fixedly supported on a bracket 1020a of the support frame 1020. The drive shaft 1320a is rotatably supported at the support frame 1020 via a bearing 1330. If the drive shaft 1320a is rotated, the radiation head 1000 is swung about the S2-drive shaft, as shown in FIG. 33.

As is shown in FIG. 37A, waveguides 510 are provided in link arms 213 and 215 of the waveguide system 211. Rotary RF couplers 500 are provided in joint portions 214 and 216. Microwaves are introduced into the acceleration tube 1100 in the radiation head through the paired rotary RF couplers 500A and 500B.

Referring now to a timing chart of FIG. 41, the radiation and the operations of the treatment apparatus 162 according to the embodiment will now be described. In particular, a description will be given of the method of preventing the effect of direct rays, leak rays and scattered rays of the treatment radiation upon the detectors, and realizing real-time time-division processing for the application of the image-acquiring X-ray and the application of the treatment radiation.

If the main switch of the radiation treatment apparatus 162 is turned on, the power supplies to the treatment bed system 207, 208, radiation head 1000, X-ray CT unit 230, microwave oscillator 270, system control unit 280 and system utility 290 are set in the standby state. The top plate 208 moves to shift the patient 204 into the treatment area. At this time, the X-ray CT unit 230 and/or the bed 207 is moved to position the diseased part 205 at the isocenter 205a. After the isocentric positioning is completed, the X-ray CT unit 230 starts real-time image acquisition and radiation treatment is performed by the radiation head 1000.

Figure 41:
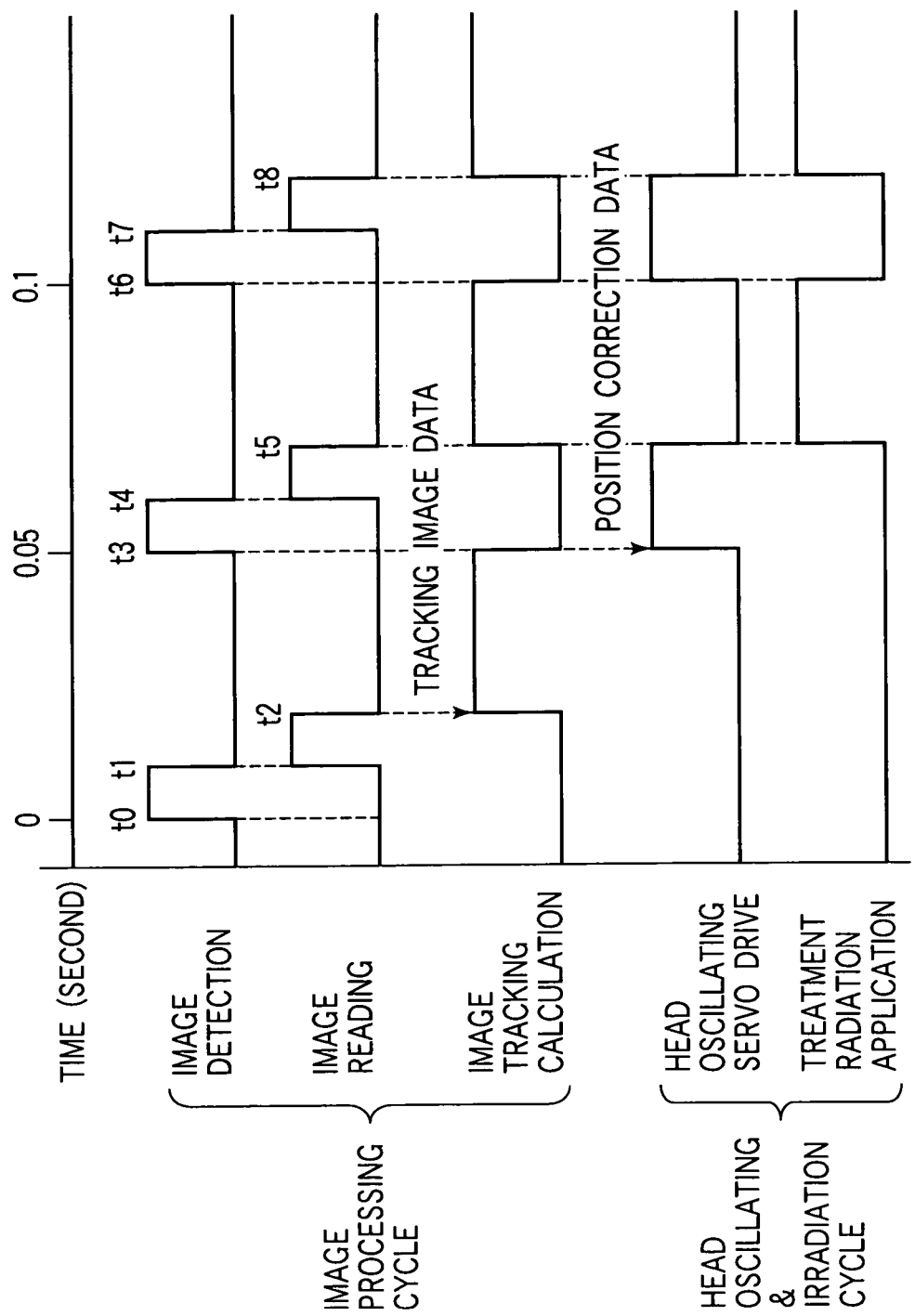
FIG. 41 is a timing chart illustrating the operation of the 15th embodiment.

In FIG. 41, at time t0, the X-ray CT unit 230 starts irradiation of the image-acquiring X-ray 203b toward the irradiation field 205. The obtained transmission image is detected as an acquired image in a time period t0–t1 in FIG. 41. In order to minimize the dose, the irradiation time of image-acquiring X-ray 203b is limited to the time period t0–t1. The radiation head 1000 is interlocked so as not to emit the treatment radiation 203a, in order to prevent the direct rays, leak rays and scattered rays of the treatment radiation 203a from affecting the detectors, at least in the time period t0–t1 in which the image-acquiring X-ray 203b is applied.

The detected acquired-image is taken in (recorded) in a time period t1–t2. Information such as tracking image data of the taken-in acquired image is processed by the signal processing unit 231 and system control unit 280 in the time period t2–t3. The processed image is displayed on the display. After the image tracking calculation, the processed information is sent to the swinging mechanisms 1310 and 1320 as position correction data. After time t3, the same cycle of time period t0–t3 between the image acquisition and the image processing is repeated.

While the next image detection and image take-in are performed in a time period t3–t5, the swinging servo of the swinging mechanisms 1310 and 1320 is effected over small swing angles θ1 and θ2, on the basis of the image tracking calculation result sent as the position correction data. During the time period t3–t5 when the swinging mechanisms 1310 and 1320 are driven, the radiation head 1000 is interlocked in consideration of safety so as not to apply the treatment radiation 203a.

At time t5 when the swinging mechanisms 1310 and 1320 are stopped, the interlock of the radiation head 1000 is released and the application of the treatment radiation 203a begins. The irradiation time of the treatment radiation 203a is a time period t5–t6 before the next driving of the swinging mechanisms 1310 and 1320. In synchronism with the time period t5–t6, the image tracking calculation of the tracking image data of the image acquired in the time period t3–t5 is carried out. At time t6, third image detection and second swinging servo drive are started, and the second image tracking calculation and the first application of the treatment radiation 203a are completed.

At time t6, after the application of the treatment radiation 203a is stopped, the application of the image-acquiring X-ray 203b is started. The next image processing cycle begins at time t6. At time t8 corresponding to the completion of the third image acquisition from time t0, the interlock of the radiation head 1000 is released and the second application of the treatment radiation 203a is started.

As stated above, the image processing cycle and the swinging & irradiation cycle overlap each other. The cycle of the head swinging drive and the application of the treatment radiation 203a, which is performed in a certain image processing cycle, is executed based on the information of the previous image processing cycle performed just before this image processing cycle.

In order to follow quick movement of, e.g. heartbeats, the time period t0–t6, during which the image detection begins, the swinging of the radiation head 1000 is performed and the application of the treatment radiation 203a is finished, is generally set within 0.1 second. In the timing chart of FIG. 41, each of the image processing cycle and the swinging & irradiation cycle is set at 0.05 second. Thus, the time intervals in the timing chart of FIG. 41 are merely by way of example, and other time intervals may be adopted.

When abnormality occurs in the image acquisition or image tracking calculation, the interlock is effected to stop the application of the treatment radiation 203a at that time, thereby enhancing the safety. The radiation treatment apparatus 162 of this embodiment is designed such that the treatment radiation 203a is applied after confirming that the swinging and positioning of the radiation head 1000 have normally been carried out.

According to the radiation treatment apparatus 162 of this embodiment as described above, the image detection cycle, the image take-in cycle and the image tracking calculation cycle, as well as the head swing control cycle and the treatment radiation 203a application cycle, based on those cycle, are repeated. Thus, the treatment is performed by applying radiation to the irradiation field 205 from a position on the ½ sphere relative to the bed 207 in a tracking manner.

Figure 42:
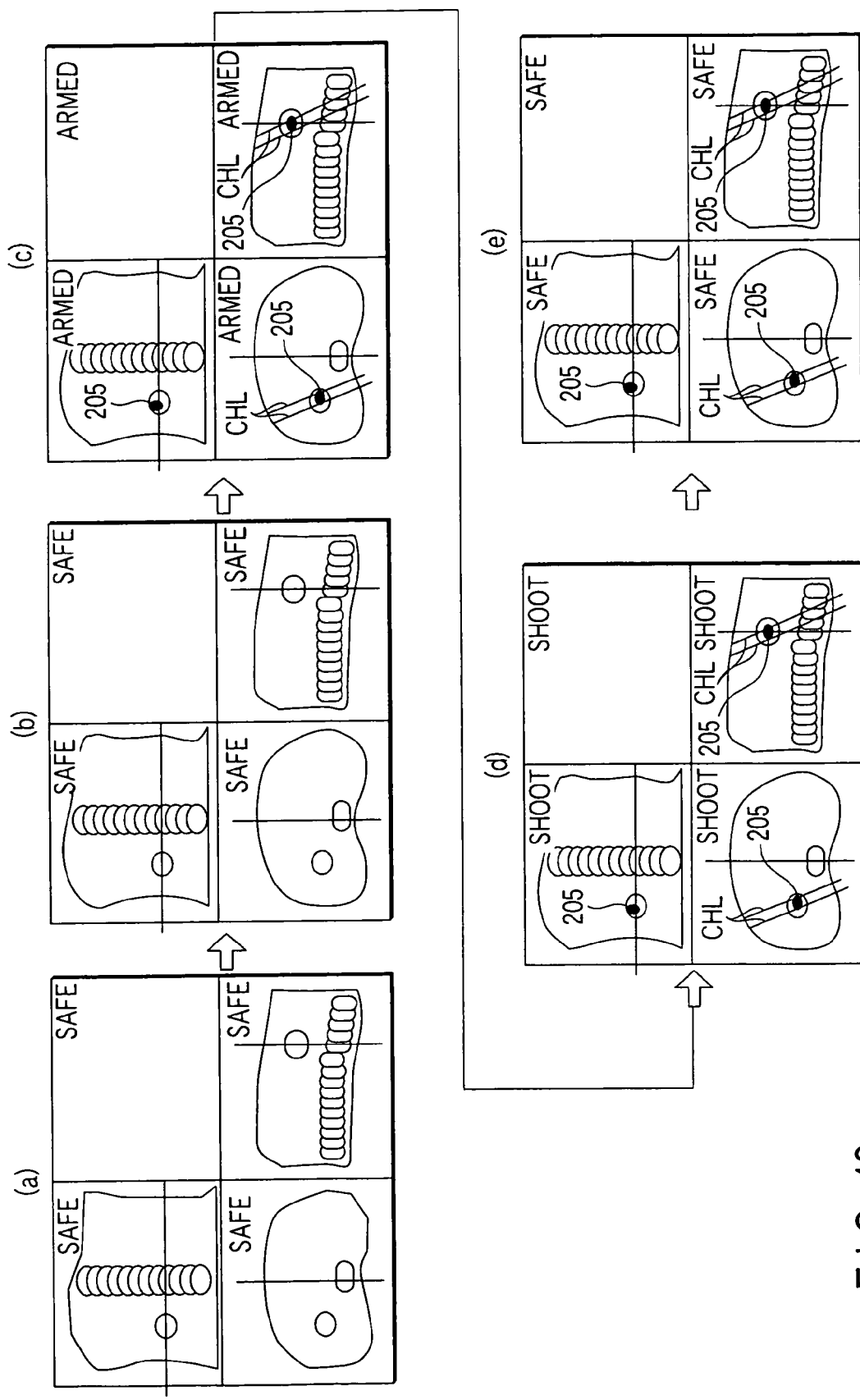
FIG. 42 illustrates operational procedures of the radiation treatment in the 15th embodiment, referring to a transitional change of monitor screens.

The treatment method of the radiation treatment apparatus 162 of the above-described embodiment is illustrated in portions (a) to (e) of FIG. 42. Since FIG. 42 is the same as FIG. 26, a description thereof is omitted.

According to the radiation treatment apparatus 162 of the above-described embodiment, the radiation head 1000 can be quickly swung within 0.1 second including the image processing time, in a tracking manner in accordance with the movement of the irradiation field (diseased part). Therefore, high-precision application of radiation can be realized.

The radiation treatment apparatus 162 of this embodiment can perform non-isocentric irradiation with high responsivity and high precision in accordance with the movement of the diseased part. Thus, the radiation treatment apparatus 162 can select a region as a subject of medical treatment, which is the object of radiation, such as a tumor that is placed in parts of the patient, other than the head, and moved owing to the movement or state of organs, for example, respiration, heartbeats, peristalsis, urine in the bladder, etc.

Figure 43:
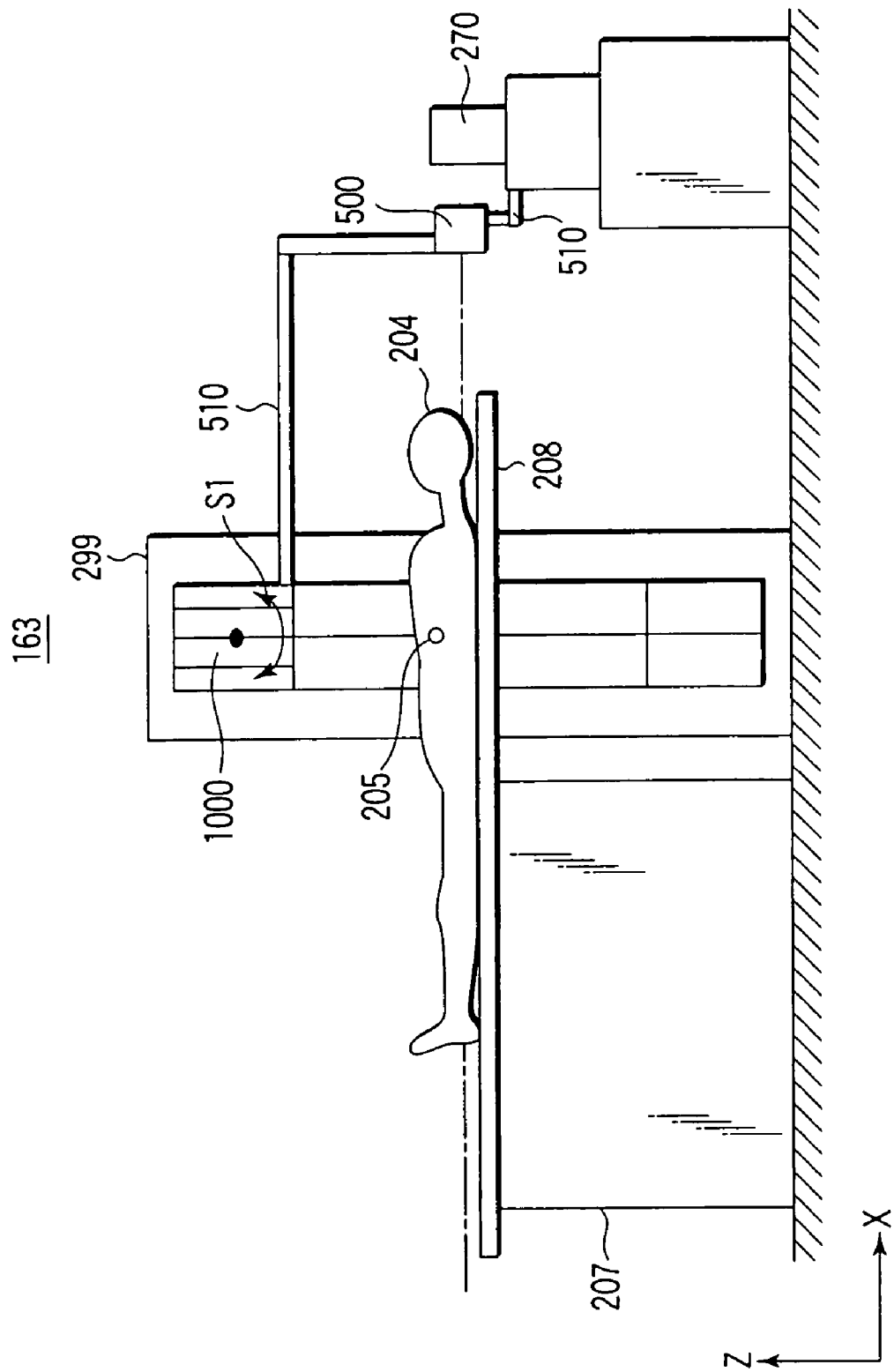
FIG. 43 shows the structure of a radiation treatment apparatus according to a 16th embodiment of the invention which is viewed in a direction perpendicular to the axis of the bed.
Figure 44:
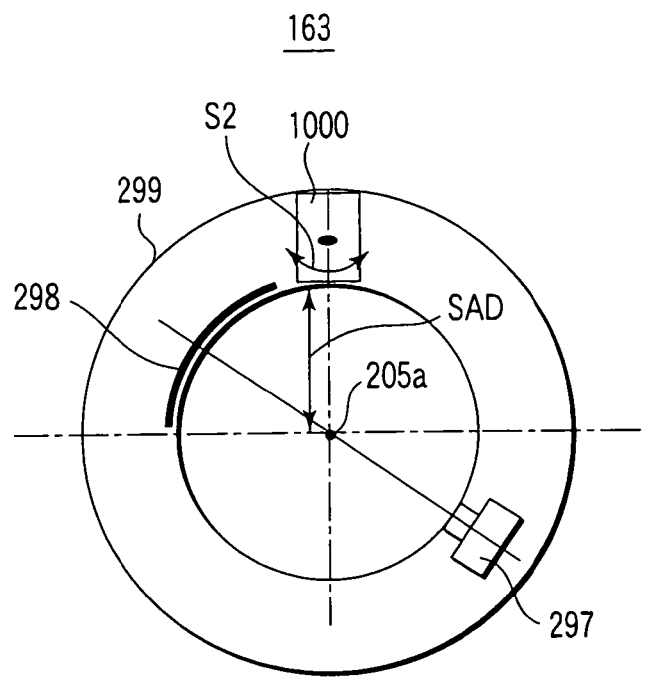
FIG. 44 shows the structure of the radiation treatment apparatus according to the 16th embodiment, as viewed in a bed-axis direction.

A radiation treatment apparatus 163 according to a 16th embodiment of the invention will now be described with reference to FIGS. 43 and 44. In FIGS. 43 and 44, the same parts as those shown in the preceding Figures are denoted by same reference numerals, and a description thereof is omitted.

In the radiation treatment apparatus 163 of this embodiment, a radiation head 1000, an image-acquiring X-ray source 297, i.e. an X-ray tube, and a sensor array 298 of an X-ray CT unit are mounted on a rotary drum 299. The radiation head 1000 is disposed on the drum of a third-generation X-ray CT unit or the like. The center of rotation of the rotary drum 299 coincides with the isocenter 205a. The radiation head 1000 includes a linear accelerator that generates radiation of 4 MeV to 10 MeV. As is shown in the Figures, the radiation head 1000 has two-axis (S1, S2) swinging mechanisms. By the movability of the swinging mechanisms, non-isocentric irradiation can be performed about the rotational axis of the rotary drum 299. An alignment of aiming angle is needed for the swinging operation about the S2 axis due to rotation of the rotary drum 299. As regards the swinging operation about the S1 axis, such alignment of aiming angle is not needed.

The image-acquiring X-ray source 297 and sensor array 298 are attached at predetermined positions on the rotary drum 299 such that no interference occurs with the radiation head 1000. The image-acquiring X-ray source 297 and sensor array 298 are opposed to each other. The sensor array 298 is a multi-row sensor.

Figure 45:
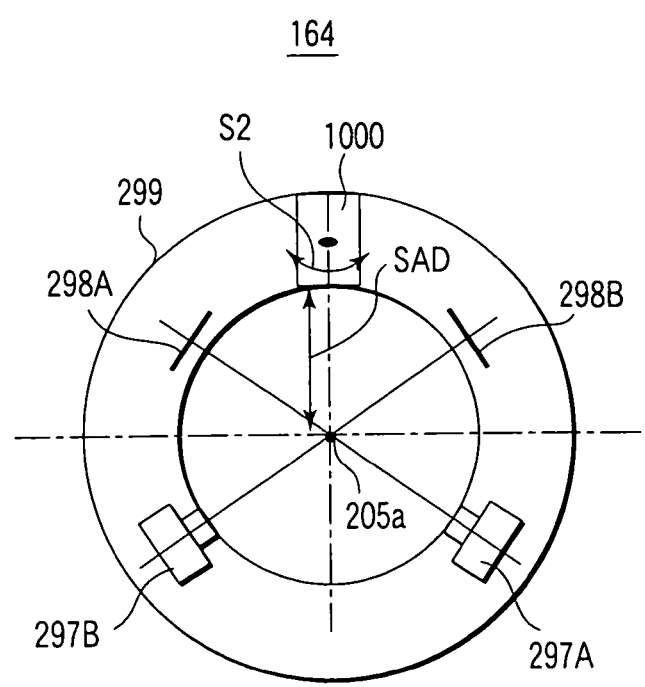
FIG. 45 shows the structure of a radiation treatment apparatus according to a 17th embodiment of the invention, as viewed in a bed-axis direction.

A radiation treatment apparatus 164 according to a 17th embodiment of the invention will now be described with reference to FIG. 45. In FIG. 45, the same parts as those shown in the preceding Figures are denoted by same reference numerals, and a description thereof is omitted.

In the radiation treatment apparatus 164 of this embodiment, a radiation head 1000, X-ray sources 297A and 297B and sensor arrays 298A and 298B are mounted on a rotary drum 299. The set of the X-ray source 297A and sensor array 298A and the set of the X-ray source 297B and sensor array 298B function as X-ray transmission units, respectively. The visual lines of the two X-ray transmission units do not coincide. Thereby, X-ray transmission images, which include an image of marker such as a landmark or a small metal plate in the patient 204, can be acquired in two axial directions, and the movement of the position of the diseased part can be understood. In the radiation treatment apparatus 164, it is available to enhance the X-ray transmission image by using contrast media for image processing, such as DSA (Digital Subtraction Angiogram). The radiation head 1000 is the same as the radiation head 1000 of the radiation treatment apparatus 163 described in connection with the 16th embodiment.

The present invention can be applied to a radiation treatment in which a radiation treatment apparatus is required a fine operation.

What is claimed is:

1. A radiation treatment apparatus comprising:
a radiation generating unit that emits radiation;
a movable member that rotatably supports the radiation generating unit on two rotational axes crossing each other;
a guide that moves the movable member carrying the radiation generating unit along an orbit with a predetermined radius about an isocenter such that the emitted radiation crosses at one point;
a support member that rotates the guide about a turning axis extended through the isocenter and arranged in parallel with a plane defined by the orbit;
an imager that acquires information of a radiation transmission image of an area including the isocenter; and
a control unit which controls two axes of the movable member that rotatably supports the radiation generating unit, to change a radiation direction of the radiation generating unit on the basis of the information acquired by the imager.

2. The radiation treatment apparatus according to claim 1, wherein the movable member is disposed on at least a pair of rails provided on the guide.

3. The radiation treatment apparatus according to claim 1, wherein the guide has a range of movement of the radiation generating unit, which is greater than a range that permits the radiation generating unit to emit the radiation to the isocenter in opposite directions.

4. The radiation treatment apparatus according to claim 1, wherein the guide is supported by the support member at one portion on the turning axis.

5. The radiation treatment apparatus according to claim 4, wherein the support member has a drive unit, which rotates the guide about the turning axis, at a location where the guide is rotatably supported.

6. The radiation treatment apparatus according to claim 1, wherein the guide is supported by the support members at two portions on the turning axis on both sides of the isocenter.

7. The radiation treatment apparatus according to claim 6, wherein the support member has a drive unit, which rotates the guide about the turning axis, at least at one of locations where the guide is rotatably supported.

8. The radiation treatment apparatus according to claim 1, wherein the guide is provided in an arcuate shape and is supported by the support member on a turning axis horizontally extending through the isocenter.

9. The radiation treatment apparatus according to claim 1, wherein the guide is provided in an arcuate shape and is supported by the support member on a turning axis vertically extending through the isocenter.

10. The radiation treatment apparatus according to claim 1, wherein the guide is provided in an annular shape and is supported by the support member on a turning axis horizontally extending through the isocenter.

11. The radiation treatment apparatus according to claim 1, wherein the guide is provided in an annular shape and is supported by the support member on a turning axis vertically extending through the isocenter.

12. The radiation treatment apparatus according to claim 1, wherein the support member is fixed to a position closer to the floor than to the isocenter.

13. The radiation treatment apparatus according to claim 1, wherein the support member is fixed to a position closer to the ceiling than to the isocenter.

14. The radiation treatment apparatus according to claim 1, wherein the movable member has a drive unit that moves by holding a belt provided on an outer peripheral side of the guide.

15. The radiation treatment apparatus according to claim 1, wherein the radiation generating unit has a variable collimator having a window, which can change a shape, for emission of radiation.

16. The radiation treatment apparatus according to claim 1, wherein the imager includes a plurality of radiation sources for acquiring the radiation transmission image, the radiation sources emitting radiation crossing at the isocenter, and detectors paired with the radiation sources, the detectors detecting the radiation that has been emitted from the radiation sources and has passed through the isocenter.

17. The radiation treatment apparatus according to claim 1, further comprising a variable collimator that alters a cross-sectional shape of the radiation emitted from the radiation generating unit, and a control unit that alters the shape of a window of the variable collimator to emit the radiation on the basis of the information acquired by the imager.

18. The radiation treatment apparatus according to claim 1, wherein the imager is an X-ray CT scanner.

19. The radiation treatment apparatus according to claim 1, further comprising a microwave source which supplies microwaves to the radiation generating unit via a waveguide, the microwave source being positioned apart from the movable member and the guide.

20. The radiation treatment apparatus according to claim 1, further comprising a movable table that positions an object of radiation within a range including the isocenter.

21. The radiation treatment apparatus according to claim 20, wherein the movable table has a slide board on which the object of radiation is placed, and a drive mechanism that moves the slide board along three orthogonal axes.

22. The radiation treatment apparatus according to claim 1, wherein the imager comprises two sets of radiation sources and detectors.

23. A radiation treatment apparatus comprising:
a radiation generating unit that emits radiation;
a movable member that rotatably supports the radiation generating unit on two rotational axes crossing each other;
a guide that moves the movable member carrying the radiation generating unit along an orbit with a predetermined radius about an isocenter such that the emitted radiation crosses at one point;
a support member that rotates the guide about a turning axis extended through the isocenter and arranged in parallel with a plane defined by the orbit; and
a microwave source which supplies microwaves to the radiation generating unit via a waveguide, the microwave source being positioned apart from the movable member and the guide.

* * * * *